United States Patent [19]

Rose

[11] Patent Number: 6,080,383

[45] Date of Patent: Jun. 27, 2000

[54] METHOD AND COMPOSITION FOR THE TREATMENT OF CANCER BY THE ENZYMATIC CONVERSION OF SOLUBLE RADIOACTIVE TOXIC AGENTS INTO RADIOACTIVE TOXIC PRECIPITATES IN THE CANCER

[76] Inventor: Samuel Rose, 5562 Marshall St., Oakland, Calif. 94608

[21] Appl. No.: 08/782,219

[22] Filed: Jan. 13, 1997

[51] Int. Cl.[7] ............................ A61K 51/00; A61M 36/14
[52] U.S. Cl. ........................ 424/1.69; 424/1.11; 424/1.57; 424/9.1; 514/2
[58] Field of Search .................................. 424/1.11, 1.37, 424/1.49, 1.57, 1.65, 1.69, 1.73, 1.81, 1.85, 1.87, 9.1, 9.2, 9.3, 9.4, 9.5, 9.6, 178.1; 530/300, 866, 391.1, 391.7, 391.9, 388.8, 402, 408, 409; 435/7.23; 536/6.4; 514/2

[56] References Cited

U.S. PATENT DOCUMENTS

| | | | |
|---|---|---|---|
| 3,964,467 | 6/1976 | Rose | 128/1 |
| 4,064,006 | 12/1977 | Rose | 195/1.8 |
| 4,189,470 | 2/1980 | Rose | 424/85 |
| 4,861,581 | 8/1989 | Epstein et al. | 424/1.11 |
| 5,087,616 | 2/1992 | Myers et al. | 514/21 |

FOREIGN PATENT DOCUMENTS 0109861  5/1984  European Pat. Off. .

*Primary Examiner*—Jose' G. Dees
*Assistant Examiner*—Dameron Jones
*Attorney, Agent, or Firm*—John Q. McQuillan

[57] ABSTRACT

A method for the treatment of cancer is disclosed which is capable of directing supra-lethal doses of radiation, called Hot-Spots, virtually exclusively to the cancer. The present invention involves a multi-step therapy process and includes a class of novel chemical agents. In accordance with the present invention, it was discovered that soluble precipitable materials can be made to accumulate as non-digestible precipitates in targeted cells as a result of enzyme action within the targeted cells. Accumulation is achieved by administering to the living host a soluble binary reagent made by attaching a targeting agent to a novel chemical agent which is a soluble precipitable material. The binary reagent binds to antigenic receptors on targeted cells which endocytose the binary reagent and transport it into the lysosomes where enzymes detach the soluble precipitable material from the targeting agent, causing it to precipitate, accumulate, and be retained in the cells. Increasing amounts of precipitate can be made to accumulate in cells by continuing the administration of the binary reagent. The accumulated precipitate is relocated to the extra-cellular fluid by selectively killing a fraction of cancer cells. Now relocated in the extra-cellular fluid of the cancer, the precipitate is used as a "platform" from which to generate Hot-Spots. A bispecific reagent with a non-mammalian enzyme moiety is made to bind to the precipitate. A soluble radioactive material is administered which is converted by the enzyme moiety of the bound bispecific reagent into a new form which is retained adjacent to the precipitate for an extended period of time, thereby generating Hot-Spots which non-selectively kill all cells adjacent to the precipitate in the extra-cellular fluid of the cancer.

86 Claims, 30 Drawing Sheets

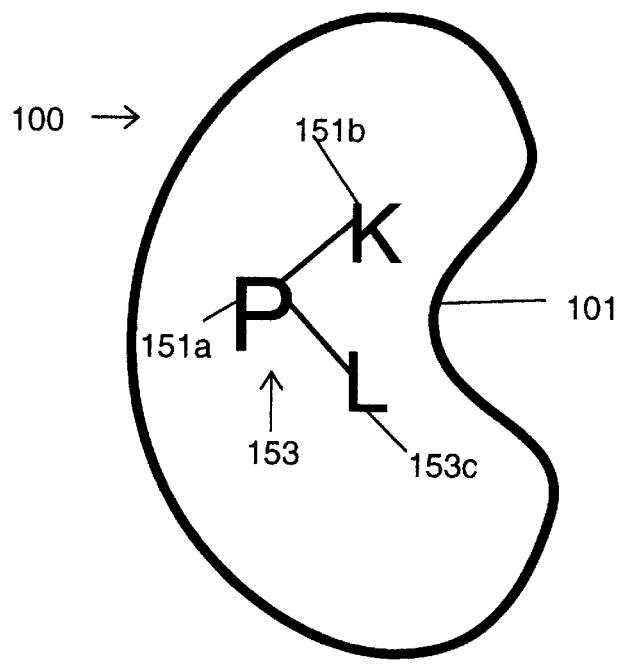
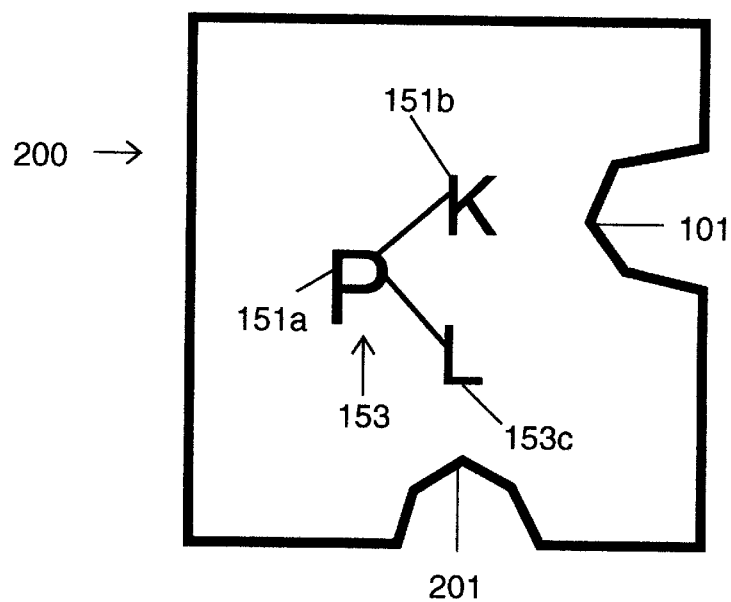
FIG. 7

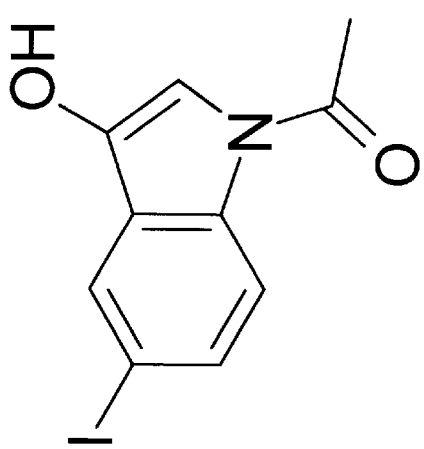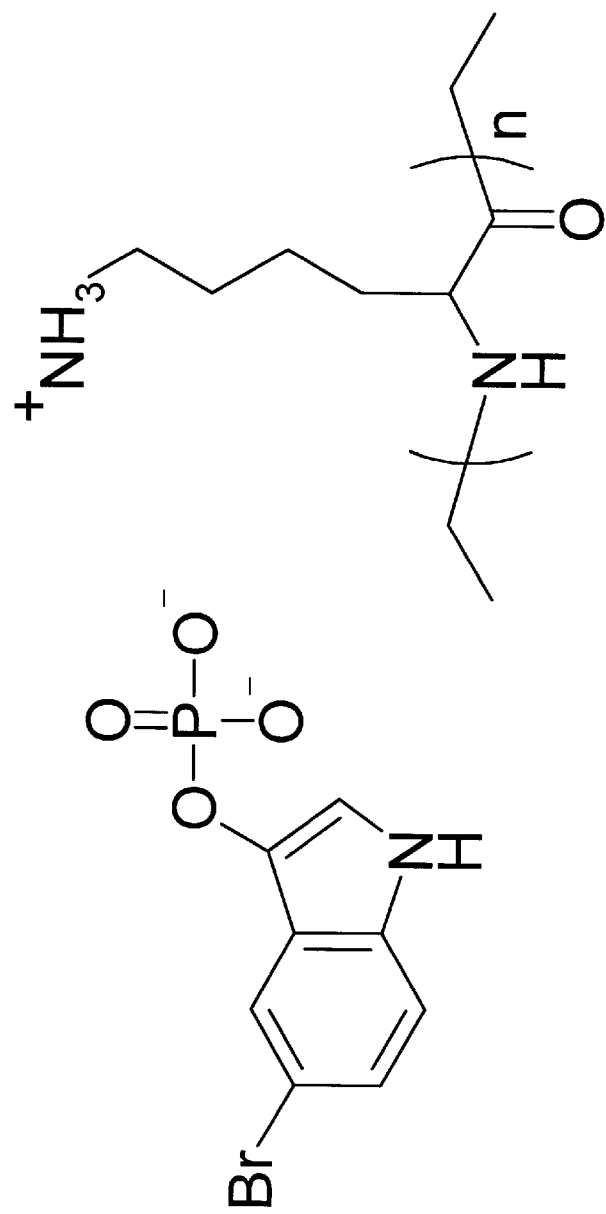
FIG. 21
FIG. 22

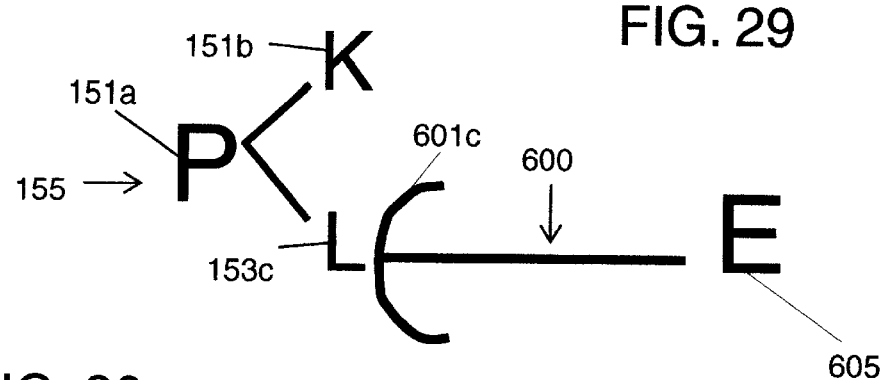
FIG. 29
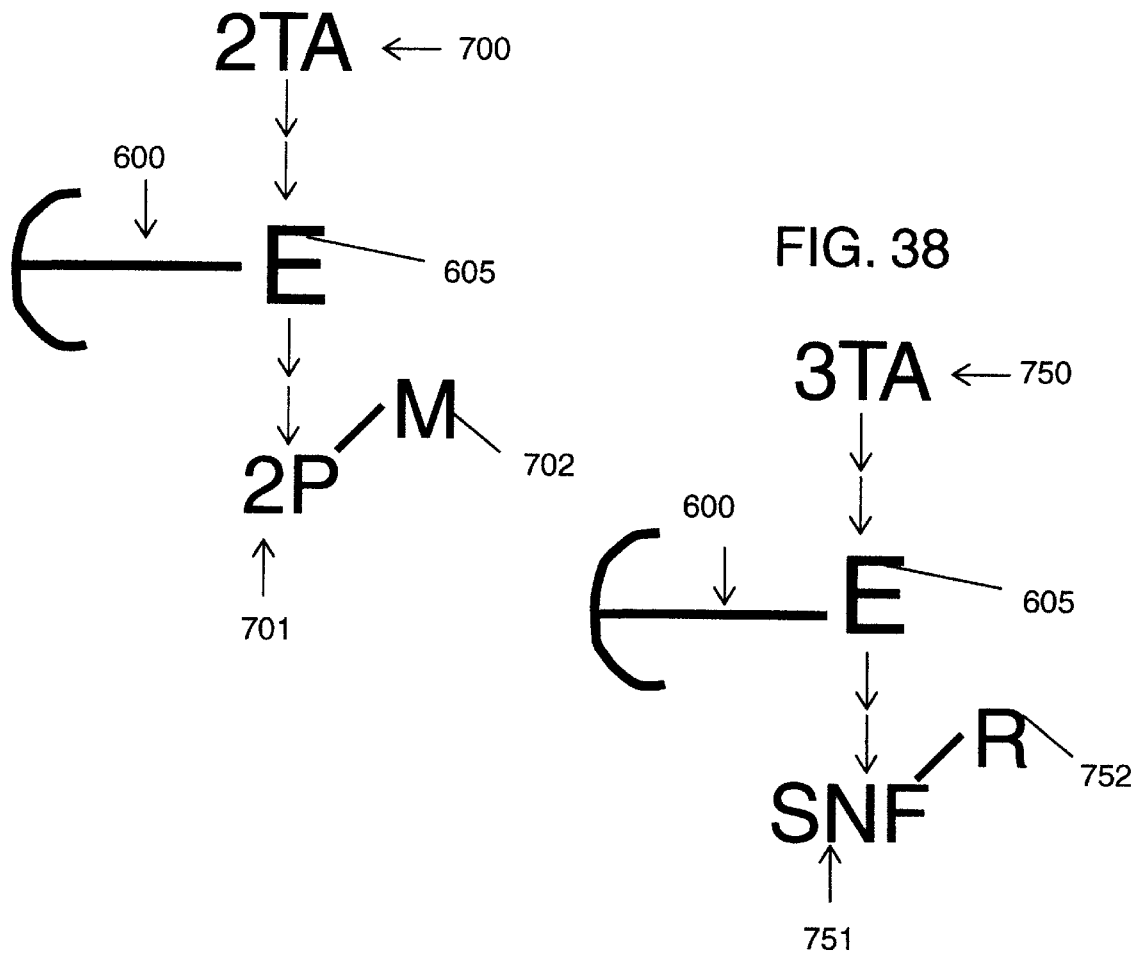
FIG. 30
FIG. 38

METHOD AND COMPOSITION FOR THE TREATMENT OF CANCER BY THE ENZYMATIC CONVERSION OF SOLUBLE RADIOACTIVE TOXIC AGENTS INTO RADIOACTIVE TOXIC PRECIPITATES IN THE CANCER

The invention relates to a method in the general field of cancer treatment, wherein a particular therapeutic effect is sought to be achieved with respect to particular cells or organisms, in humans or animals, through the use, either directly or indirectly, of targeting agents which are introduced into the living host, where the agents exhibit some kind of imperfect specificity for the cells or organisms sought to be treated and carry a soluble material which precipitates in the target cells, the accumulated precipitate being used as a platform from which to launch an aggressive attack on the cancer. In particular, the invention relates to a method of the treatment of cancer.

BACKGROUND OF THE INVENTION

1. Field of the Invention

A considerable portion of world-wide research efforts in the treatment of cancer is currently devoted to killing cancer cells by means of various cell killing agents. Despite the fact that numerous drugs, radioactive compounds, and the like have been shown to be capable of killing cancer cells, these agents fail to treat cancer successfully because of their inability to circumvent three universally present obstacles: (1) the agents do not kill all the cancer cells because they do not exhibit cytotoxic specificity for all the cancer cells, (2) the agents also kill normal cells because they do not exhibit cytotoxic specificity exclusively for cancer cells, and (3) the agents are not potent enough to kill resistant cancer cells or to overcome the ability of cancer cells to adapt and become resistant to the cell killing agents. An appreciation of these three obstacles is necessary to understand why current treatments fail and to understand the rational and methodology of the proposed invention.

Fifty years of intense research has shown that there is a wide heterogeneity in every characteristic that has been measured in cancer cells. These characteristics include cell size, buoyancy, anaerobic metabolism, enzyme composition, growth rate, gene errors, differential gene expression, chromosome number, and chromosome errors. The heterogeneity is also expressed by the presence of some cancer cells that are super-sensitive and others that are super-resistant to being killed or treated by any therapeutic agent. Within the same tumor population a fraction of cells will be sensitive to a given therapeutic agent and will be killed when that agent is administered, a fraction of cells will be resistant to the agent and will not be killed, and a fraction will adapt and become increasingly more resistant to subsequent therapeutic regimens. The resistant cells will continue to divide and spread to distant locations in the body to form metastatic tumors.

The wide heterogeneity in sensitivity to any particular therapeutic agent leads to the high probability that the systemic application of any therapeutic agent will cause partial remission of the tumor by killing the super-sensitive cancer cells, but will not be able to achieve a complete cure because it cannot kill the super-resistant cancer cells. Previous attempts at cancer therapy have generally ignored the negative therapeutic consequences of these divergent cells. There has been an intuitive and optimistic belief than an approach achieving partial remission in its early phase will give a complete cure after it has been fine-tuned. This optimism contradicts the biological principle, supported by a large amount of data, that every large population of cells or organisms is heterogeneous, and that cancer cells, which have a genetic instability, exhibit a particularly high degree of heterogeneity. Therefore, it is not surprising that the past history of cancer therapy approaches has been a monotonous sequence of short periods of hope, because killing some cancer cells leads to a remission, followed by prolonged periods of disappointment, because some cancer cells survive, seed, and continue to grow in the living host and subsequent treatments are less effective at killing the cancer cells of these metastatic tumors. It is likely that the latest field of oncogenes and other gene manipulations, as applied to cancer therapy, will also follow the same pattern. This prediction is based on the fact that there is a heterogeneity of gene errors and gene expression in the cancer cell population, and with time, more and more cells, with more and varied genetic and chromosome errors accumulate in the cancer cell population. No simple genetic correction, even if it could be applied successfully to all the cancer cells growing in the body, is likely to repair every cell.

2. Prior Art

The first serious deficiency of current cancer therapeutic approaches is that they do not take into account, and are unable to deal with, the heterogeneity of the cancer cell population. The inability of current approaches to circumvent this heterogeneity is illustrated by the failure of immuno-therapeutic approaches that rely on antigenic receptors on the surface of cancer cells to deliver therapeutic agents.

All current attempts at cancer therapy (apart from the treatment of thyroid cancer with radio-iodide) depend on killing each and every individual cancer cell by their direct individual interaction with the candidate therapeutic agents or applied environmental condition. In order to describe the need for this direct interaction, these strategies can be loosely called "sniper killing," i.e. each cell to be killed must be targeted directly. Sniper killing agents include cytotoxic drugs, binary reagents made by attaching cancer targeting agents to cytotoxic drugs, augmented immune response, hormonal therapy, genetically engineered products (like interferon), manipulations of oncogenes, or products coded by these genes.

In order for these sniper killing strategies to be successful in treating cancer, it would be necessary for the cancer cells to have an exploitable characteristic which is present on all cancer cells, for that characteristic to be absent from all (or at least most) normal cells, and for that characteristic to not adaptively change and become non-exploitable.

It is known that cancer cells exhibit on their surface numerous receptors, including antigenic receptors, to which selected molecules such as specific antibodies, hormones, and peptides can bind. Antibodies, hormones, and peptides can be used as targeting agents for the cancer cells that express those particular antigenic receptors. Ideally, all cancer cells would express the receptor, and the number of non-cancerous cells which express the receptor would be very small. In the ideal model, binary reagents (an example of a sniper strategy) which are composed of targeting agents and cytotoxic agents would be preferentially directed to the cancer cells. However, in practice, binary reagents do not result in the delivery of the cytotoxic agent to all cancer cells in the tumor population because some cancer cells do not exhibit the particular antigenic receptor. The binary reagent will not attach to these antigenic receptor deficient cancer cells, and therefore these cells will be unaffected by the treatment and will be left to proliferate in the host. High-dose sniper killing, even when employed at dose levels which kill many normal cells, fail to kill all cancer cells because some cancer cells are antigenic receptor deficient, some cancer cells are super-resistant even before the treatment begins, and some cancer cells adapt to the therapeutic agent, survive, and become resistant to future treatments. All these sniper strategies have failed, and are doomed to fail in the future, because they cannot deal with the fact that some normal cells also express the characteristic which is the target for the sniper killing, and because they cannot deal with the universally present heterogeneity and adaptive ability of cancer cells.

The recent development of highly pure and highly immuno-specific monoclonal antibodies, hormones, and peptides which can act as specific targeting agents for particular antigenic receptors has greatly increased the ability to direct cell killing agents specifically to cancer cells and thereby minimize any adverse effects on non-cancerous cells. Paradoxically, this current direction of isolating and producing such highly specific targeting agents (for the purpose of minimizing the possibility that such antibodies, and the cytotoxic agents carried thereby, might attach to non-cancerous cells) is, in one sense, counter-productive, since the number of cancer cells within the tumor population which will exhibit an affinity for such highly specific targeting agents will be reduced.

Notwithstanding the above-mentioned advances in the development of highly specific targeting agents to deliver the cell killing agents specifically to targeted cells, and the demonstrated cell killing ability of the particular delivered agents, therapeutic success through the use of binary reagents composed of targeting agents and toxic agents has not been achieved, and should not have been expected. Unfortunately, in practice these therapies have been far less successful than they were hoped to be.

The second serious deficiency of binary reagents to carry cytotoxic agents to target cancer cells is that the so called "cancer targeting agents" of which the binary reagents are made, also target a significant number of normal cells. These targeted normal cells are also killed by the administration of binary reagents, cause unacceptable destruction of normal tissues, serious illness of the patient, and limit the aggressiveness of the attack which can be launched against the cancer.

The third serious deficiency of binary reagents to carry cytotoxic agents to target cancer cells, particularly cytotoxic radioactive isotopes, is that they cause significant systemic toxicity because the targeting agent carrying the cytotoxic agent is a large molecule which causes them to have a long residence time in the blood circulation, and causes them to be taken up non-specifically by normal cells.

The fourth serious deficiency of binary reagents to carry cytotoxic agents to cancer cells is that even those cancer cells which the targeting agents attaches to, outright killing of the cancer cell is often not accomplished. In large part this is due to the inherent limitations of the treatment method, i.e., the absolute quantity of cytotoxic agent which can be coupled to the targeting agent is smaller than that required to actually kill the cancer cell (the small quantity of cytotoxic agent which can be attached is limited to avoid destroying the targeting ability of the targeting agent and to avoid adversely altering the distribution of the binary reagent in the host). While the amount of cytotoxic agent which can be brought to bear on cancer cells through the use of binary reagents may be sufficient to damage some of the cells, the damage often is only temporary or, indeed, simply results in the emergence of mutant cells which are still cancerous and have become resistant to the effects of the cytotoxic agent.

The fifth serious deficiency of the binary reagents to carry cytotoxic agents is that it is impossible to make a valid choice of the most appropriate targeting agent to make the binary reagent for each cancer in each patient. Furthermore, it is not possible to predict the outcome of the therapy prior to administering the binary reagent at the necessary cytotoxic dose level.

Despite the three obstacles and the deficiencies described above, the treatment of thyroid cancer with radio-iodide is successful in a high proportion of cases. This high rate of success is not due to a fundamental difference between cancer cells of the thyroid and cancer cells which have arisen from other tissues. The successful treatment of thyroid cancer is due to the fact that normal and malignant thyroid cells have a unique biological function which allows them to store iodine. Thus, when patients with thyroid cancer are treated with radio-iodide, a fraction of the cancer cells take up sufficient quantities of isotope and store the isotope long enough to generate micro-regions of intense radiation in which all the cells in each micro-region are killed. These intense radiation fields, called Hot-Spots, are generated exclusively in the normal and malignant thyroid tissue. The radiation field in the Hot-Spots extends beyond the cells taking up the isotope and kills hundreds of neighboring cells thereby creating overlapping micro-regions of supra-lethal radiation (overlapping Hot-Spots) exclusively in the thyroid tissue. Inside these Hot-Spots, the radiation is so intense that all the cancer cells in the tumor are killed, including the cells that do not take up the radio-isotope.

Two types of strategies have been employed to amplify and localize the effect of cytotoxic agents on targeted cells in order to circumvent the five deficiencies described and in order to simulate the operating conditions that make the treatment of thyroid cancer so successful. The first strategy attempts to accumulate the cytotoxic agents inside targeted cells and the second strategy attempts to form and accumulate cytotoxic agents outside targeted cells in the extra-cellular fluid of the tumor.

The first strategy to amplify and localize the effect of cytotoxic agents on targeted cells is to accumulate cytoxic agents inside cells. In many normal and disease states, it is desirable to target therapeutic and/or tracer chemicals to specific cell types. Two problems exist in such targeting. The first problem is how to cause the targeting to be specific for certain cell types. The second problem is how to accumulate and retain the therapeutic and/or tracer chemical in the region of the targeted cells for as long as possible in order to maximize the effect on the targeted cells, and at the same time minimize the effect on non-targeted cells by preventing the therapeutic and/or tracer chemical from leaving the region of the targeted cells, diffusing away, and reaching the regions of non-targeted cells.

Progress has been made on the first problem by accumulating the therapeutic and/or tracer agent inside targeted cells. This has been achieved by constructing a binary reagent by covalently attaching the therapeutic or tracer chemical to proteins, such as antibodies, hormones, or peptides which act as targeting agents (Ghose T. and Blair A. H. 1987, CRC Critical Reviews of Therapeutic Drug Carrier Systems, 3, 262–359; Blakely et al. 1988, Progress in Allergy, 45, 50–9). The protein targeting agent moiety of the binary reagent binds to endocytosing antigenic receptors on certain cell types, called target cells, and delivers the therapeutic or tracer chemical agent to the desired target cells. The binding of the targeting agent to the antigenic receptor on the target cells induces the target cells to undergo receptor mediated endocytosis which causes the cells to "swallow" the receptor and bound binary reagent, and to transport the receptor and binary reagent to lysosome vacuoles. The lysosome vacuoles have an acidic environment and contain a high concentration of numerous proteolytic, glycanolytic, nuclease, and lipolytic enzymes. Once inside the lysosomes, the receptors are released from the binary reagents and recycle back to the cell surface to bind more binary reagents and to thus continue repeating the receptor mediated endocytosis process. In this manner, each receptor can recycle 5 to 10 times per hour. Inside the lysosomes, the targeting agent moiety of the binary reagent is digested, and the therapeutic or tracer chemical is released as a free, soluble molecule. In this free state the chemical exerts its tracer or pharmacological therapeutic action.

Cytotoxic drugs, toxins, dyes, antidotes to toxic drugs, and molecules carrying radio-isotopes have been delivered to cells by this means (Ali et al. 1990, Cancer R. Suppl. 50, 783–788; Wu et al. 1985, Hepatology 1985, 5, 709–713; Wu et al. 1983, Proc. Nalt Acad. Sci., 80, 3078–3080; Firestone Raymond 1994, Bioconjugate, 5, 105–113; C. Rushfeldt and Brad Smedsrod 1993, Cancer Research 1993, 53, 658–662; Pittman et al. 1983, Biochem. J. 212, 791–800; Jansen et al. 1992, Hepatology 18, 146–152; Daniel A. Vallera 1994, Blood, 83, 309–317; A. Mukhopadhyay and S. K. Basu 1990, Biotechnology and Applied Biochem. 12, 529–536).

Some progress has also been made regarding the second problem of the attached therapeutic and/or tracer chemical leaving the targeted cells . The second problem has been partly solved by trapping the released chemical in the lysosomes of the targeted cell. For example, one approach to the problem of intra-cellular trapping that has been described uses a common disaccharide, sucrose, as a marker of fluid endocytosis. Since mammalian cells lack the necessary glycosidase, the sucrose is not digested, and since sucrose is unable to rapidly cross the cell membrane, the sucrose is partially trapped in the cell. Thus, the amount of sucrose which is trapped can be used as an approximate measure of sucrose uptake.

Taking advantage of these properties of sucrose, a technique was developed for determining the sites of degradation of plasma proteins, by using the proteins as targeting agents which are covalently attached to radio-sucrose to make a binary reagent The binary reagent is introduced into targeted cells by receptor mediated endocytosis to measure the rate of degradation of the targeting agent protein. After the administration and receptor mediated endocytosis of the binary reagent, the protein targeting agent moiety of the binary reagent is enzymatically digested, causing the release of the soluble radio-sucrose molecules as a free molecules. Since sucrose is not degraded and remains partially trapped within the cell, the amount which has accumulated in the cell can be used as an approximate measure of the amount degradation of the protein targeting agent by the targeted cells (Pittman and Steinberg 1978, Biochem. Biophys. Res. Commun. 81, 1251–259; Pittman et al. 1979, J. Bio. Chem.; 254, 6876–6879; Pittman et al. 1979, Proc. Natl. Acad. Sci. USA 76, 5345–5349).

More recently, it has been shown that soluble cellobiose can be used in a similar manner to sucrose. Cellobiose can be linked by a non-metabolizable bond to the therapeutic or tracer chemical, so that the soluble cellobiose and the attached therapeutic or tracer chemical, once free from its attachment to the targeting agent, accumulates in the targeted cells (Pittman et al. 1983, Biochem. J. 212, 791–800; Pittman, 1984, U.S. Pat. No. 4,466,951). The cellobiose method has certain advantages over the use of sucrose.

Nevertheless, both the soluble sucrose and cellobiose have the disadvantage in that the accumulated carbohydrate, with or without an attached therapeutic chemical, slowly leaves the cell. Therefore, cells cannot continue to accumulate increasing amounts of carbohydrate. There is the added disadvantage that the accumulated carbohydrate can diffuse away from the targeted cell and reach cells which were not targeted.

The second strategy to amplify and localize the effect of cytotoxic agents on targeted cells is to form the cytotoxic agents outside targeted cells in the extra-cellular fluid. The formation of cytotoxic agents outside targeted cells in the extra-cellular fluid of the targeted regions has been achieved by the enzymatic conversion of a pro-drug into an active drug by a method called Antibody Dependent Enzyme Pro-Drug Therapy (ADEPT). The enzyme which makes the conversion is one moiety of a bispecific reagent, the other moiety being an antibody with a binding affinity to the non-endocytosing receptors on surface of targeted cancer cells. Since the enzyme moiety is bound to the surface of the targeted cells, the conversion from pro-drug to the active drug takes place in the extracellular fluid.

The active drug diffuses into the immediate micro-region to have its pharmacological cytotoxic effect on the non-target cancer cells in the micro-region. For example, alkaline phosphatase converts the pro-drugs mitomycin phosphate into an active mitomycin C derivative and etoposide phosphate into an active etoposide (Senter et al, 1989, Cancer Research, 49, 5789–5792), beta-lactamase converts a cephalosporin derivative of 4-de-succetylvinblastine-3-carboxhydrazide into an active cytotoxic drug (Meyer et al, 1993, Cancer research, 53, 3956–3963), and activates cephalo- doxorubcin (Rodrigues et al, 1995, Cancer Research, 55, 63–70), DT diaphorase followed by a non-enzymatic reaction with a thioester activates the monofunctional alkylating agent CB 1954 into an active agent which can cause ctotoxicity by cross-linking DNA (Knox et al, 1993, Cancer and Metastasis Reviews, 12, 195–212); carboxypeptidase G2 can convert a nitrogen mustard pro-drug into an active drug (Springer and Niculescu-Duvaz, 1995, Anticancer Drug Des. 10, 361–372); nitroreductase can activate CB1954 (Knox et al, 1995, Biochem. Pharmacol., 49, 1641–1647); and dinitrobenzamide (Anlezark et al, 1995, Biochem. Pharmacol., 50, 609–618); to form cytotoxic derivatives, and alpha-galactosidase can activate prodrugs of anthaacycline (Azoulay et al, 1995, Anticancer Drug Des., 10, 441–450).

The three step ADEPT approach fails to successfully treat cancer for the following reasons: (a) the bispecific reagent is bound to the non-endocytosing target cancer cells and also to some normal cells because the targeting agent moiety does not exhibit exclusive cytotoxic specificity for cancer cells which reduces the tumor specificity of the non-mammalian enzyme location and pro drug conversion, (b) the antigenic receptors of the target cells are in a constant state of flux which prevents the bispecific reagent from remaining bound for a sufficient period of time to allow all bispecific reagent not bound specifically to the target cell receptors to be eliminated from the body prior to administering the pro-drug; (c) the soluble active drug which is made by the enzyme diffuses away from its site of production to have a cytotoxic action on healthy normal cells; (d)

the cells on which the bispecific reagent is bound, and where the active drug is formed, are the first cells to be killed because they receive the highest concentration of the active drug. When these cells are killed, the enzyme will no longer be in a position to convert the pro-drug into an active drug and, therefore, the production of active drug is self limiting; and (e) the shape and volume of the micro-region in which there is a sufficiently high concentration of the active drug to kill cells is variable and ill-defined because the diffusion parameters of the soluble active drug are dependent on the particular status of the blood capillaries and extra-cellular structures in the cancer, the parameters of the diffusion varying from one location of the tumor to another.

The two strategies described above fail to generate Hot-Spots because the number of cytotoxic chemical or radio-isotope agents which are delivered is small, the number being directly proportional to the relatively small number of antigenic receptors on the surface of the target cells. In addition, the agents or isotopes do not remain in the correct location for long enough to achieve an aggressive attack on the cancer, and furthermore, they cause systemic toxicity because the agents circulate in the blood for a long period of time. Finally these strategies also fail to locate the attack specifically to the tumor, because the location where the agent or isotopes are delivered or where the active drug is made is dependent on only a single cancer associated characteristic on the cancer cell surface, and every single characteristic found on cancer cells is also found on some normal cells.

The present invention mimics for non-thyroid cancers, the Hot-Spot killing which makes the treatment of thyroid cancer successful; however, since no other malignant tissue has the same natural iodide involving process as the thyroid, the mimicking requires the construction of a special, multi-step, sequential process to achieve "Hot-Spots" in non-thyroid cancers. The basic process of the present invention consists of sequential steps which act independently and together with naturally occurring characteristics of the cancer and normal cell populations to generate overlapping Hot-Spots virtally exclusively in the tumor without causing significant systemic toxicity. Cancer cells within these Hot-Spots are eradicated, the eradicated cells include cancer cells that are not targeted, cancer cells that are resistant and even super-resistant, and cancer cells that would otherwise adapt and become resistant to therapy.

SUMMARY OF INVENTION

An object of the present invention is to provide a method for the treatment of cancer that directs supra-lethal doses of radiation in the form of micro-regions of radiation, called Hot-Spots, virtually exclusively to the cancer. All the cells, numbering in the thousands, within each Hot-Spot are killed, therefore, the method of the present invention does not require each individual cancer cell to be targeted in order for each cancer cell to be killed. As a consequence the method of the present invention is not defeated by the heterogeneity of cancer cell receptors and the imperfect nature of current targeting agents. Because the Hot-Spots are located virtually exclusively in the region of the cancer, the present invention does not kill healthy cells and will not cause significant systemic toxicity.

It is another object of the present invention to provide a method for accumulating soluble precipitable materials as non-digestible precipitates in targeted cells as a result of enzyme action within the targeted cells. The accumulation of the precipitate is achieved by the administration of a soluble binary reagent made by attaching a targeting agent to a soluble precipitable material. The binary reagent binds to antigenic receptors on the targeted cells, which causes the cell to endocytose the binary reagent and transport it to the lysosomes in the cell. The lysosome enzymes in the cell detach the soluble precipitable material from the targeting agent and cause the material to precipitate, accumulate, and be retained for an extended period of time in the cell. The amount of precipitate which can be made to accumulate increases with the continued administration of the binary reagent. T he intra-cellular accumulated precipitate is relocated to the extra-cellular fluid by selectively killing cancer cells that are super-sensitive to any one of the toxic and non-toxic anti-cancer agents and the now extra-cellular precipitate is used as a "platform" to generate Hot-Spots. A bispecific reagent with a non-mammalian enzyme moiety is made to bind to the precipitate. After all unbound bispecific reagent is eliminated from the body, an additional therapeutic agent which is a soluble radioactive toxic agent is administered to the living host. The additional therapeutic agent is converted by the bound non-mammalian enzyme into a new form enabling the new form which is retained adjacent to the extra-cellular precipitate for an extended period of time thereby generating an intense radiation field, i.e. a Hot-Spot, to kill non-selectively all cells adjacent to the extra-cellular precipitate and thus having the potential to kill all cancer cells in the body of the living host.

It is a further object of the present invention to provide a method for the immunological treatment of any cell population or organism for therapeutic purposes.

It is an additional object of the present invention to provide a soluble precipitable material which is adapted to form non-digestible precipitates in targeted cells as a result of enzyme action within the targeted cells.

It is a further object of the present invention to provide a bispecific reagent adapted to have a non-mammalian enzyme moiety and a targeting agent moiety, the bispecific reagent being capable of binding to the precipitate.

It is still a further object of the present invention to provide a soluble radioactive toxic agent adapted to be converted by the non-mammalian enzyme moiety of the bispecific reagent into a new form which is retained adjacent to the extra-cellular precipitate for an extended period of time thereby generating an intense radiation field, i.e. a Hot-Spot, to kill non-selectively all cells adjacent to the extra-cellular precipitate.

BRIEF DESCRIPTION OF THE DRAWINGS

FIG. 7 shows the formation of precipitate in the first target cancer cells and the first target normal cells.

FIG. 21 shows the method of radio-iodinating indoxyl compounds where 1-acetyl-5 iodo-3-hydroxyindole is exchanged with radioactive iodine.

FIG. 22 shows salt of polylysine and indolphosphoric acid.

FIG. 29 shows the bispecific reagent binding to the neo-antigenic third epitope of the first extra-cellular precipitate.

FIG. 30 shows the second therapeutic agent being converted by the non-mammalian enzyme of the bispecific reagent into the second extra-cellular precipitate.

FIG. 38 shows the third therapeutic agent being converted by the non-mammalian enzyme of the bispecific reagent into the new form of the third therapeutic agent, the new form being soluble.

DESCRIPTION OF THE PREFERRED EMBODIMENTS

The present invention is a method for treating a heterogeneous population of cancer cells in a living host by at least a first therapeutic agent and an additional therapeutic agent. The living host being composed of normal cells growing in a normal extra-cellular matrix, the normal extra-cellular matrix having at least collagen and fibronectin, the heterogeneous population of cancer cells growing in a cancer-altered extra-cellular matrix having at least cancer-altered antigenic epitopes 99 (FIG. 1), the heterogeneous population of cancer cells endogenously making and containing products including at least sulphated glycomminoglycans, natural intra-cellular enzymes in the lysosomes, and natural intra-cellular material including DNA, histone, and complexes of DNA-histone, the DNA, histone and complexes of DNA-histone 400 having antigenic epitopes 401 (Epstein et al 1995, Cancer Research 55, 2673–2680; Akaogi et al., 1996, Proc. Natl. Acad. Sci., 93, 8384–8389). The heterogeneous population of cancer cells include at least three sub-populations of cancer cells.

Figure 1:
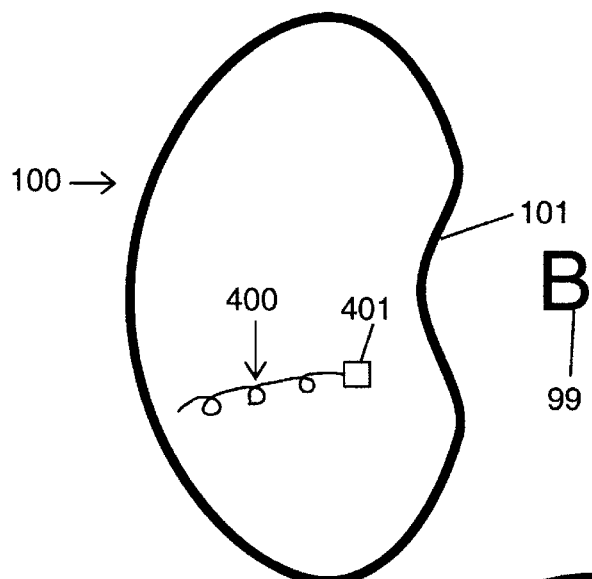
FIG. 1 shows the first target cancer cells.
Figure 2:
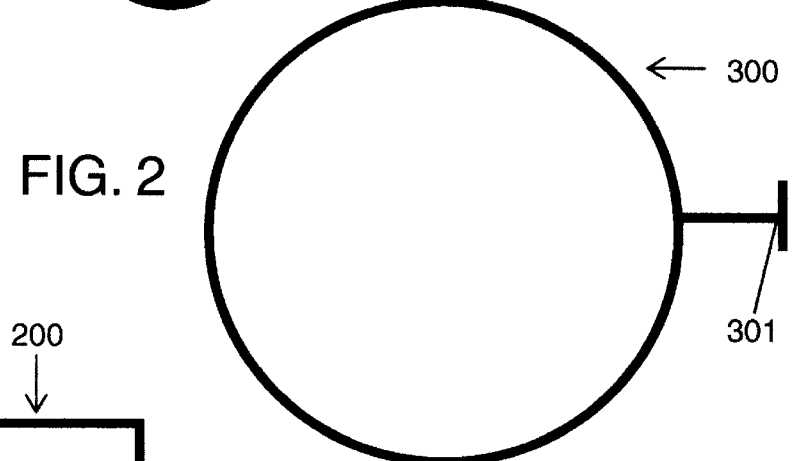
FIG. 2 shows the second target cancer cells.

As shown in FIG. 1 the first sub-population of cancer cells being the first target cancer cells 100 each having a first antigenic receptor 101 which is substantially specific to a cancer cell and which is capable of binding a first targeting agent, the first antigenic receptor 101 being capable of endocytosis when the first targeting agent binds to the first antigenic receptor. The first target cancer cells 100 also having a high sensitivity to being killed by the natural system of the living host and a high sensitivity to being killed by the first therapeutic agent The first target cancer cells 100 endogenously making and containing products including at least sulphated glycosaminoglycans, natural intra-cellular enzymes in the lysosomes, and natural intra-cellular material including DNA, histone, and complexes of DNA-histone, the DNA, histone and complexes of DNA-histone 400 having antigenic epitopes 401. The second subpopulation of cancer cells, as shown in FIG. 2, being the second target cancer cells 300 each having a third antigenic receptor 301 which is substantially specific to a cancer cell and which is capable of binding a third targeting agent, the third antigenic receptor 301 being incapable of endocytosis. The third sub-population of cancer cells being non-target cancer cells which are the remainder of the cancer cells.

Figure 3:
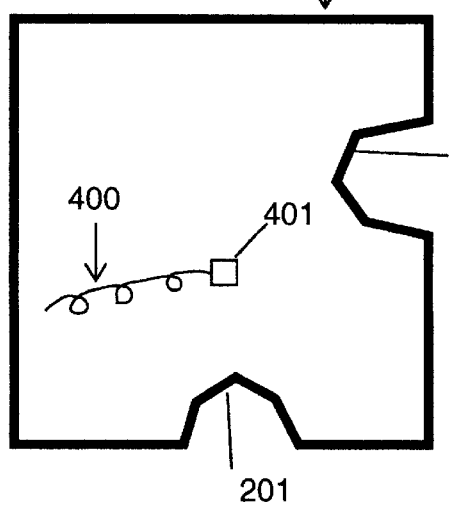
FIG. 3 shows the first target normal cells.

The normal cells of the living host endogenously making and containing products including at least sulphated glycosaminoglycans, natural intra-cellular enzymes in the lysosomes, and natural intra-cellular material including DNA, histone, and complexes of DNA-histone, the DNA, histone, and complexes of DNA-histone having antigenic epitopes. The normal cells including at least two subpopulations of normal cells. As shown in FIG. 3, a first sub-population of normal cells being the first target normal cells 200 which also have the first antigenic receptor 101 and further having a high sensitivity to being killed by the natural system of the living host and a high sensitivity to being killed by the first therapeutic agent. The first target normal cells also having a second antigenic receptor 201 which is substantially specific to normal cells and which is capable of binding a second targeting agent, the second antigenic receptor being capable of endocytosis when the second targeting agent binds to the second antigenic receptor. The first target normal cells making and containing products including at least sulphated glycosaminoglycans, natural intra-cellular enzymes in the lysosomes, and natural intra-cellular material including DNA, histone, and complexes of DNA-histone, the DNA, histone, and complexes of DNA-histone 400 having antigenic epitopes 401. The second sub-population of normal cells being non-target normal cells which are the remainder of the normal cells.

Figure 4:
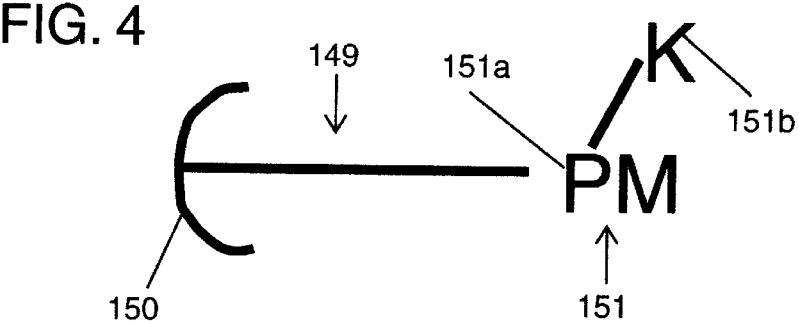
FIG. 4 shows the binary reagent.

The method of the invention comprising a plurality of steps including at least introducing into the living host a binary reagent. FIG. 4 shows the binary reagent 149 which is introduced to the living host, the binary reagent having two moieties, the first moiety being the first targeting agent 150 which has the substantial affinity for the first antigenic receptors, the second moiety of the binary reagent 149 being a soluble precipitable material 151 having a first antigenic epitope 151a and a second antigenic epitope 151b is attached to the first targeting agent 150.

Figure 5:
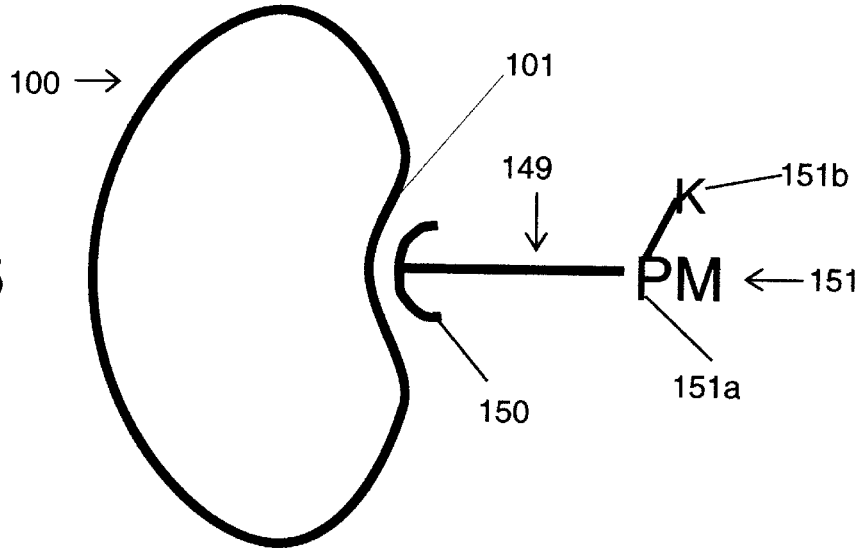
FIG. 5 shows the binary reagent binding to the first target cancer cells.
Figure 6:
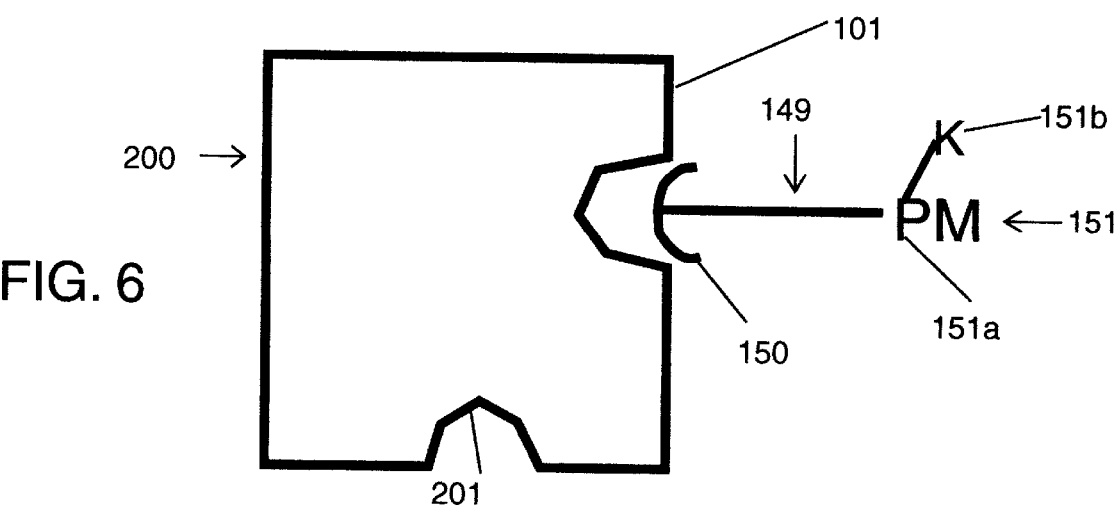
FIG. 6 shows the binary reagent binding to the first target normal cells.

As shown in FIG. 5 the first targeting agent 150 of the binary reagent 149 attaches to the first antigenic receptor 101 of the first target cancer cells 100, thereby permitting the binary reagent 149 to be endocytosed into the lysosomes of the first target cancer cells. FIG. 6 shows the attachment of the first targeting agent 150 of the binary reagent 149 to the first antigenic receptors 101 of the first target normal cells 200, thereby permitting the binary reagent 149 to be endocytosed into the lysosomes of the first target normal cells.

The endocytosing and the natural intra-cellular enzymes in the lysosomes of the cells, as illustrated in FIG. 7, causes the soluble precipitable material 151 to detach from the first targeting agent and enables the detached soluble precipitable material to form a precipitate 153 which has an antigenic epitope. The antigenic epitope on the precipitate 153 being the same antigenic epitope as the soluble precipitable material and being the first antigenic epitope 151a. The precipitate having the second antigenic epitope 151b, and further having a neo-antigenic third epitope 153c, the precipitate 153 accumulating in the lysosomes within the first target cancer cells 100 and within the first target normal cells 200.

Figure 8:
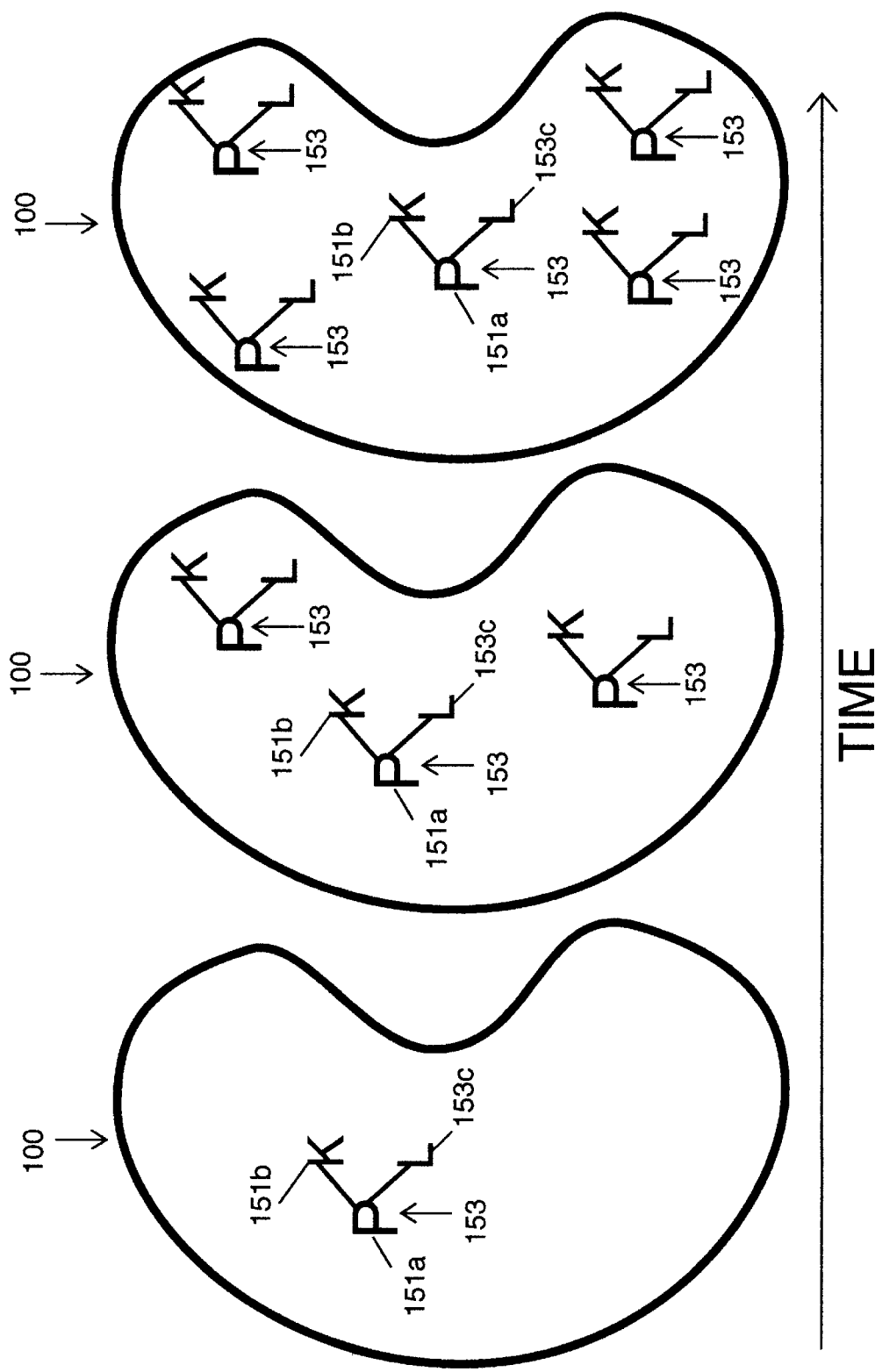
FIG. 8 shows the accumulation of precipitate forming in the first target cancer cells.

The method of the present invention further comprises the step of continuing the introducing of the binary reagent into the living host to increase the amount of the accumulation of the precipitate. FIG. 8 shows the accumulation of the precipitate 153 in the first target cancer cells 100 to form a plurality of antigenic epitopes which is proportional to the amount of accumulation. Accumulation of the precipitate is achieved by continuing the introducing of the binary reagent 149 into the living host and allowing more soluble precipitable material 151 to precipitate within the cells, the continued formation of precipitate 153 causing an accumulation of precipitate in the first target cancer cell 100 to occur. The precipitate 153 having a first antigenic epitope 151a, a second antigenic epitope 151b, and a neoantigenic third epitope 153c, and the accumulation of precipitate 153 thereby becoming a plurality of epitopes 151a, 151b, 153c.

The introducing of the binary reagent, the permitting of the cell to undergo endocytosis, and the continuing of the introducing of the binary reagent results in the formation of a precipitate inside the target cells and accumulation of the precipitate inside the first target cancer cells and the first target normal cells.

The accumulation step is achieved by exploiting receptor mediated endocytosis, the natural on-going "swallowing" process of cells, the precipitate itself being stable and non-digestible by mammalian enzymes. Unlike soluble chemicals, the precipitate cannot leave the cells. For these reasons, the process of precipitate accumulation is a cumulative time dependent process. It is possible, by the continued administration of the binary reagent, to accumulate any desired amount of precipitate. For example, in 100 hours, 1000 times as many molecules of precipitate can be accumulated in the cell as there are receptors on the cell surface at any time.

Intra-cellular formation and accumulation of the precipitate relies on the action of endogenous lysosomal enzymes and/or the acidic pH in the lysosomes to form the precipitate by detaching the precipitable material from the targeting agent and converting the detached precipitable material into a precipitate. Precipitation does not occur in any appreciable amounts in the extra-cellular body fluid because this fluid does not contain active lysosomal enzymes. Any lysosomal enzyme which "accidentally" enters the extra-cellular fluid is largely inactivated by naturally circulating protein antagonists and by the neutral pH found in the extra-cellular fluid.

The currently available targeting agents which are used in the present invention to make the binary reagent cannot target every cancer cell because the cancer cells are heterogeneous with respect to the receptors to which the targeting agents specifically attach. In addition to targeting only a fraction of the cancer cells, the binary reagent also targets some normal cells. As discussed earlier, these targeting agent imperfections are the critical reasons why current immuno-therapies using binary reagents fail. The proposed Hot-Spot approach circumvents these imperfections. Unlike current therapies which require every cancer cell to interact directly with the candidate therapeutic agent to be killed, in the process of the present invention, thousands of cancer cells are killed around each cancer cell that is targeted. Therefore, there is no need for each cancer cell to be targeted individually for the therapy to succeed.

Two classes of precipitable materials can be delivered and made to accumulate in the form of a precipitate in the lysosomes of targeted cells. The first class of precipitable materials are inherently soluble in aqueous medium and can be readily attached to the protein or peptide targeting agent in aqueous medium by conventional means to make a soluble binary reagent The attachment is a non-random controlled process and is effected by ionic and Van Der Waal forces, or by covalent bonding via functional groups in the peptide such as: SH, NH2, and CO2H and by substitution into the aromatic portion of tyrosine, tryptophan, and histidine. Structural analysis of the binary reagent is made by mass spectroscopy, and the affinity of the targeting agent moiety of the binary reagent is measured to determine if it has been altered during the chemical manipulations required for the attachment of the precipitable material to the targeting agent. Aqueous soluble precipitable materials require the lysosomal enzymes and/or the acidic environment in the lysosomes both to detach the soluble precipitable material from its attachment to the cancer targeting agent and to convert the detached soluble precipitable material into a precipitate which then accumulates in the lysosomes of the targeted cells.

One example of the first class of soluble precipitable materials is made by converting chemical X to a soluble X-Y which is a soluble material compatible with a reaction medium for the protein or peptide targeting agent and can be attached in aqueous medium to the targeting agent to make a soluble binary reagent. The soluble binary reagent remains soluble because the attachment of the X-Y to the targeting agent does not disturb the linkage of X to Y. After the targeting agent of the soluble binary reagent binds to the targeted cell receptor, it activates the cell to undergo receptor mediated endocytosis which transports the soluble binary reagent to the lysosome of the cell. In the acidic, enzyme rich environment of the lysosome, the X-Y is cleaved from its attachment to the targeting agent by an esterase or peptidase and/or the acidic environment. The X-Y bond is cleaved by a lysosomal enzyme to create a highly reactive soluble intermediate molecule, Xa. The Xa molecule is readily and extremely rapidly oxidized to form a soluble oxidized molecule Xb which spontaneously and covalently self-condenses or dimerizes to create a new molecule which is insoluble and immediately precipitates. Because a new molecule is formed by the dimerization, the core structure of the precipitate has a neoantigenic epitope which is not present on the X-Y, Xa, or Xb.

Figure 9:
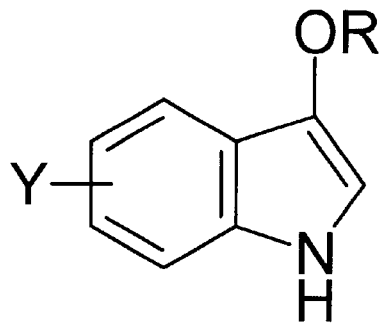
FIG. 9 shows the general structure of indole esters substituted in the benzene ring.
Figure 10:
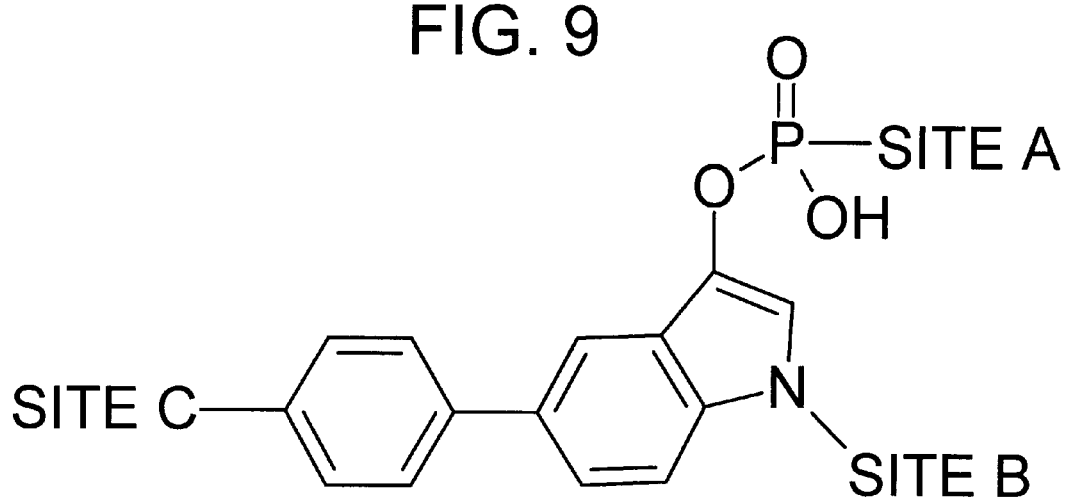
FIG. 10 shows the three sites of attachment of the targeting agent to indoxyl phosphate.
Figure 11:
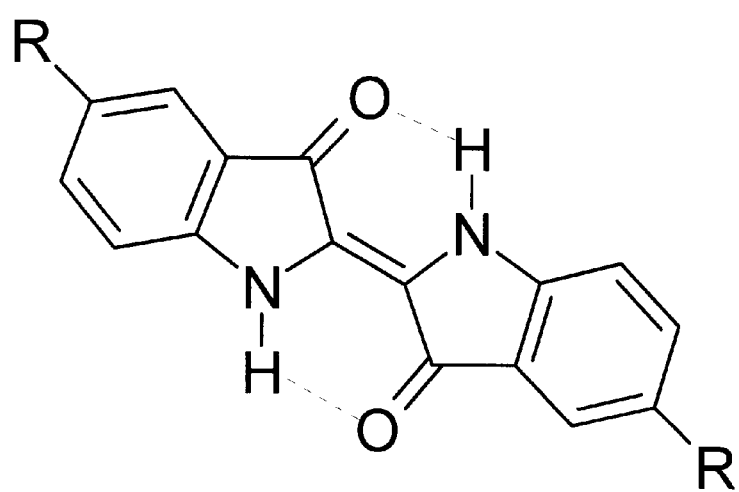
FIG. 11 shows the dimerization of two indoxyl molecules to form indigo.
Figure 12:
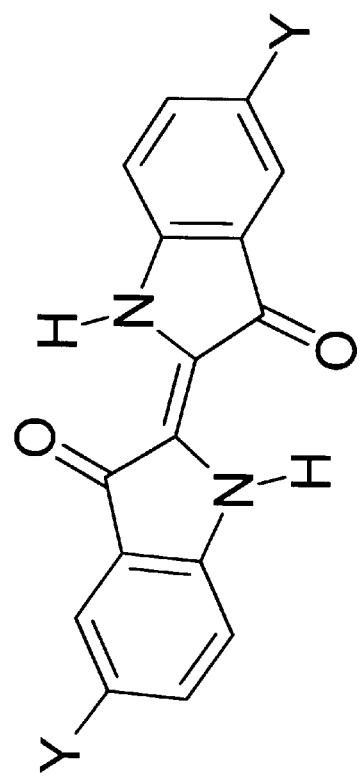
FIG. 12 shows the substituted indigos.

A specific example of this procedure is the application of an indoxyl, the general structure of indoxyl esters substituted in the benzene ring is shown in FIG. 9, where R can be one of meany chemicals including phosphate, sulphate, or various carbohydrates and where Y can be aryl, halogen, and alkyl. Indoxylphosphate, as examples of X-Y, which is freely soluble, can be attached in an aqueous medium to the protein or peptide targeting agent in three ways: (1) by non-covalent Van Der Waal forces, (2) by non-covalent ionic forces, or (3) by covalent bonds at 3 sites. The three sites for covalent bonding on the indoxylphosphate are shown in FIG. 10. In each of these methods of attachment, the indoxylphosphate (X-Y) is cleaved from the targeting agent, and the phosphate of the indoxylphosphate is cleaved by lysosomal phosphatase enzymes to liberate indoxyl (Xa) which is a highly reactive intermediate indoxyl. The indoxyl (Xa) is readily and extremely rapidly oxidized to form (Xb), and once in the oxidized form the (Xb) spontaneously self-condenses or dimerizes, as shown in FIG. 11 to form a new molecule which is insoluble and precipitates spontaneously as an indigo dye as illustrated in FIG. 12 where Y can be aryl, halogen, hydoxyl, and alkyl. The insoluble indigo dye, being a molecule different from the indoxyl compounds and the indoxyl intermediates from which the indigo dye was formed, has an antigenic epitope not found on the indoxyl compounds or the indoxyl intermediates. This antigenic epitope is a neo-antgenic third epitope.

The oxidation and dimerization of indoxyl proceeds at a slower rate at pH 4.5 of the lysosome vacuoles in which the dimerization takes place compared to the rate at a neutral or alkaline pH. This slower rate could allow some of the soluble indoxyl molecules and their intermediates to exit the cell prior to dimerizing and precipitating inside the cell, the exited molecules being free to dimerize and precipitate in the extra-cellular fluid. Various modifications can be made to the indoxylphosphate so that the rate of soluble indoxyl molecules exiting the cell is greatly reduced, and more time would be available for the dimerization and precipitation to take place, thus reducing the amount of free indoxyl and the intermediates from exiting the cell.

A first chemical , for example cellobiose, can be attached to the benzene ring of the indoxylphosphate by reductive amination, involving an amino group on the benzene ring and the reducing end (aldehyde) of the cellobiose. The result is an alkyl amino group, similar to that formed when polylysine is lactosylated by reductive amination. The resultant bond is incapable of being cleaved by mammalian enzymes, and because the first chemical has been selected to be a chemical which remains partially trapped within cells, the first chemical reduces the rate of exit of the soluble indoxyl molecules. The attachment of the first chemical to the benzene ring of the indoxylphosphate will not interfere with the release of the indoxylphosphate from its protein attachment, or the ability of the lysosome enzyme to cleave the phosphate bond, or the ability of the indoxyl to be oxidized, to dimerize, and to precipitate.

Further modifications can be made to the indoxylphosphate so that the precipitate formed from the indoxylphosphate has certain desired characteristics. For example, a second chemical with an antigenic epitope, such as penicillin, can be covalently attached to the indoxyl (X-Y), so that the indigo precipitate will have a second antigenic epitope in addition to the neo-antigenic third epitopes which developed as a result of dimerization.

Figure 13:
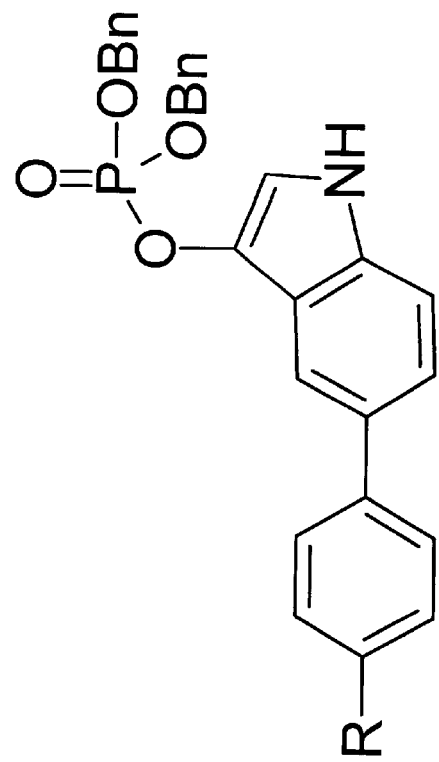
FIG. 13 shows molecule Xc, indoxylphosphate dibenzylester.
Figure 14:
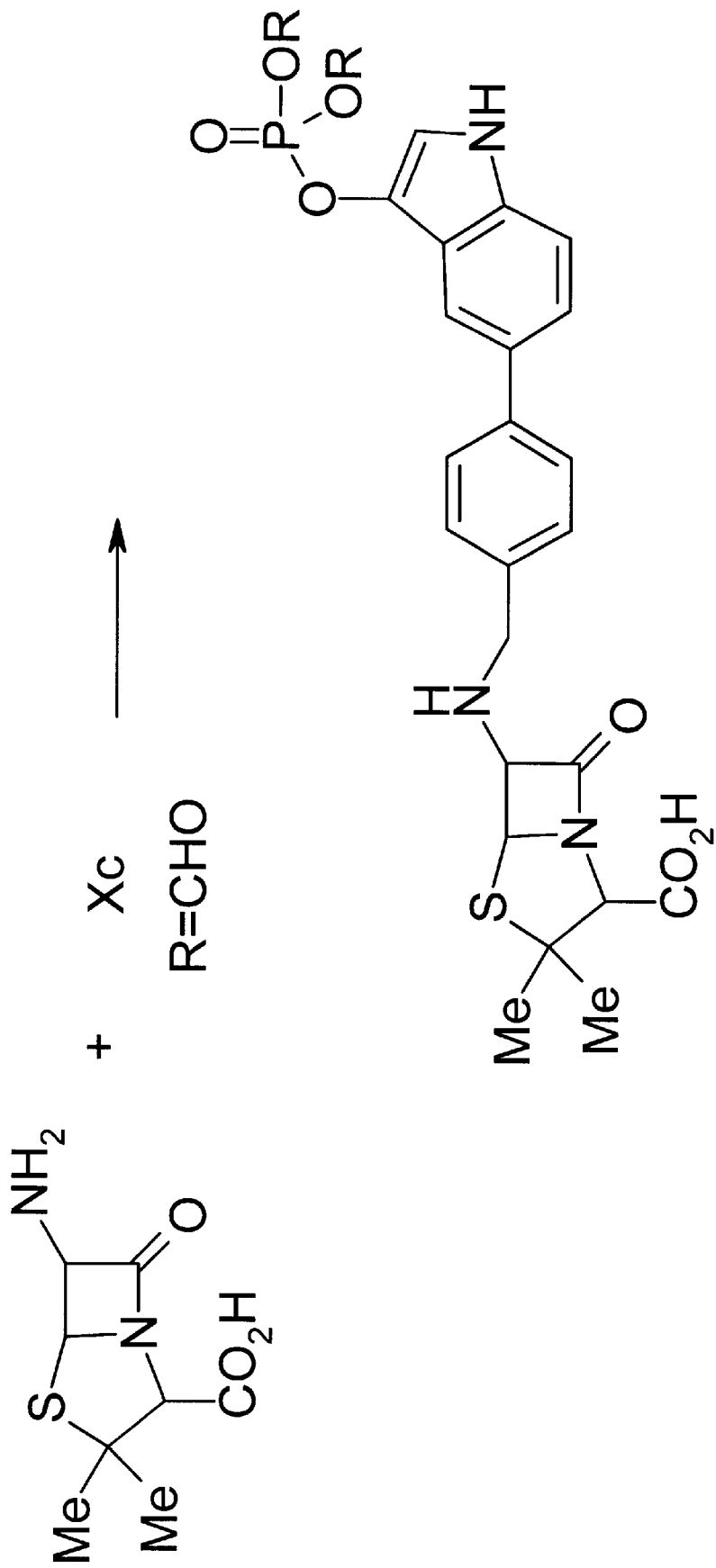
FIG. 14 shows the attachment of penicillin to the benzene ring.
Figure 15:
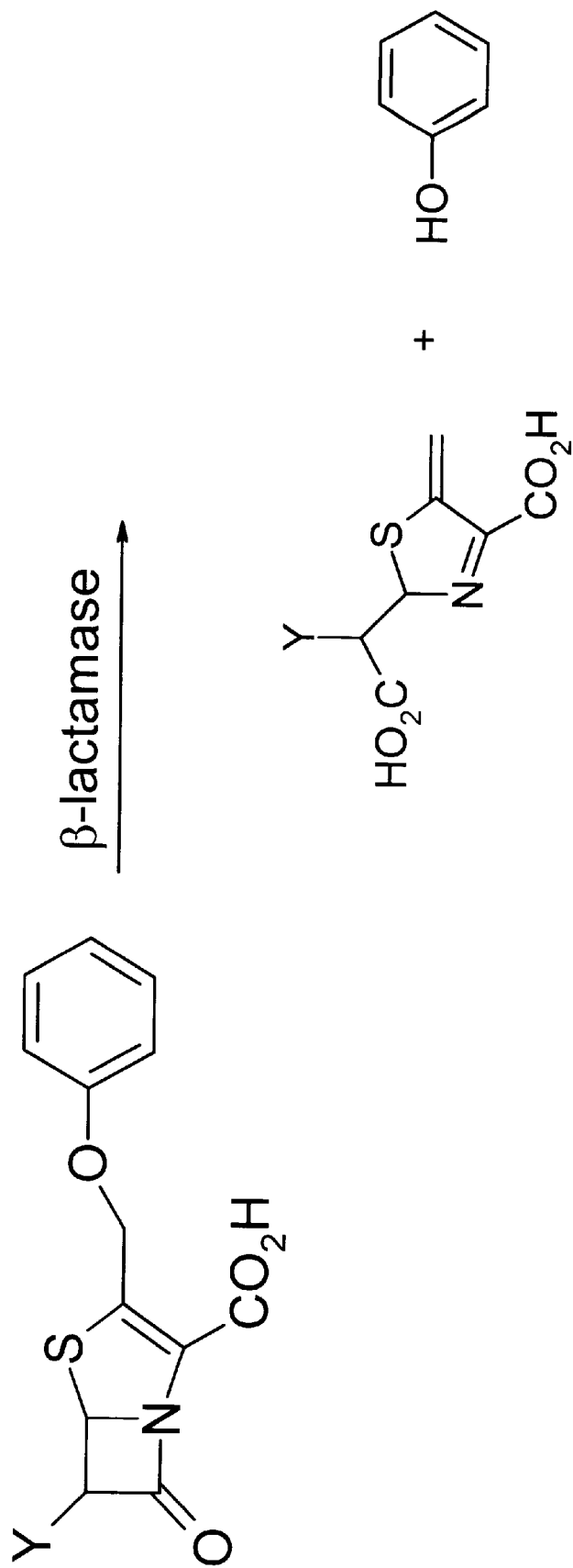
FIG. 15 shows the attachment of penicillin to the benzene ring where the bond between the benzene ring and the penicillin is unaffected by mammalian enzymes.
Figure 16:
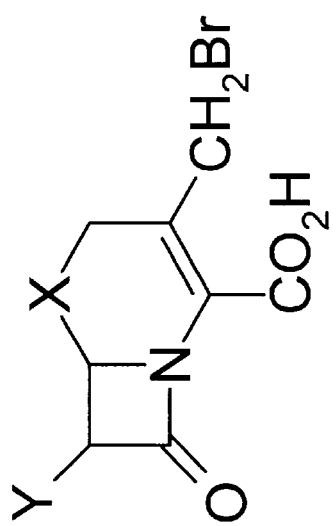
FIG. 16 shows cephalosporin.

The penicillin-indoxyl compound can be prepared by a number of methods. In the first method, the 6-aminopenicillanic acid (6-APA) moiety is attached to a substituted indoxylphosphate dibenzylester, of the type Xc as shown in FIG. 13. Various modes of attachment of the 6-aminopenicillanic acid can be used, but the preferred mode is reductive amination which leads to a non-hydrolyzable covalent bond illustrated in FIG. 14 where R is CHO. Beta lactamase acts on the penicillin to open up the lactam ring which prevents antibodies and peptides having an affinity to bind to penicillin from binding to the precipitate. In the second method, as shown in FIG. 15, the penicillin is attached to the benzene ring in a way which is unaffected by mammalian enzymes, but is cleaved by beta-lactamase which prevents antibodies and peptides having an affinity to bind to penicillin from binding to the precipitate. Many other types of molecules, particularly any amino compound, can be attached to Xc, through the hydroxy, amino, and carboxyl groups. The attachment of the second chemical having a second antigenic epitope can be achieved without interfering with any of the steps required for final precipitation to occur. The attachment of the second chemical will not interfere with the release of the indoxylphosphate from its protein attachment, will not interfere with the ability of the phosphatase enzyme to cleave the phosphate bond, and will not interfere with the ability of the indoxyl to precipitate. Exactly the same reactions can be applied to cephalosporin as shown in FIG. 16. The second antigenic epitope on the indigo precipitate provides a number of substantial advantages which are described later.

Figure 18:
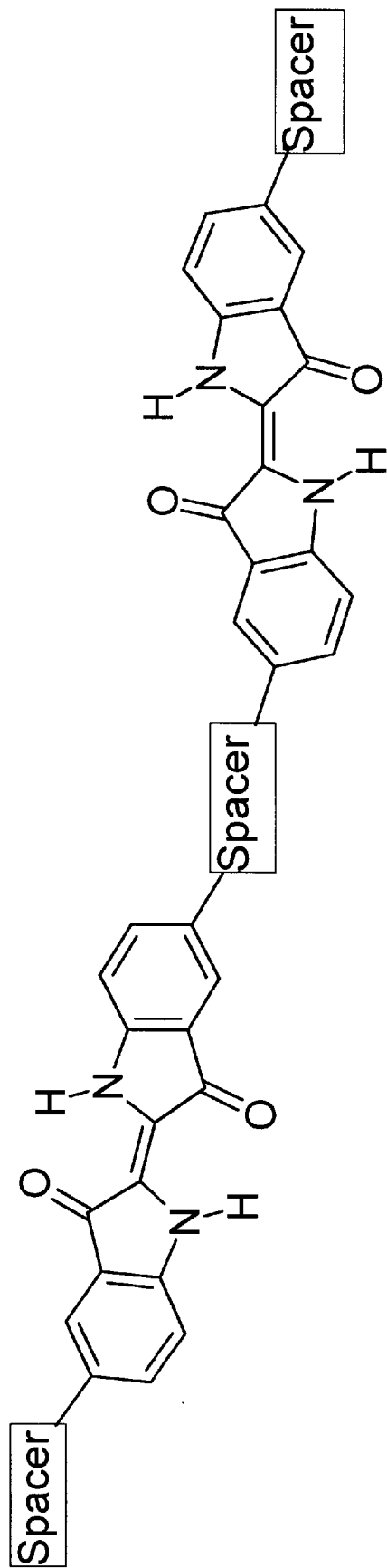
FIG. 18 shows a linear polymer formed by dimerization of 2 bi-indoxyl compounds attached at their benzene ring via a spacer.
Figure 17:
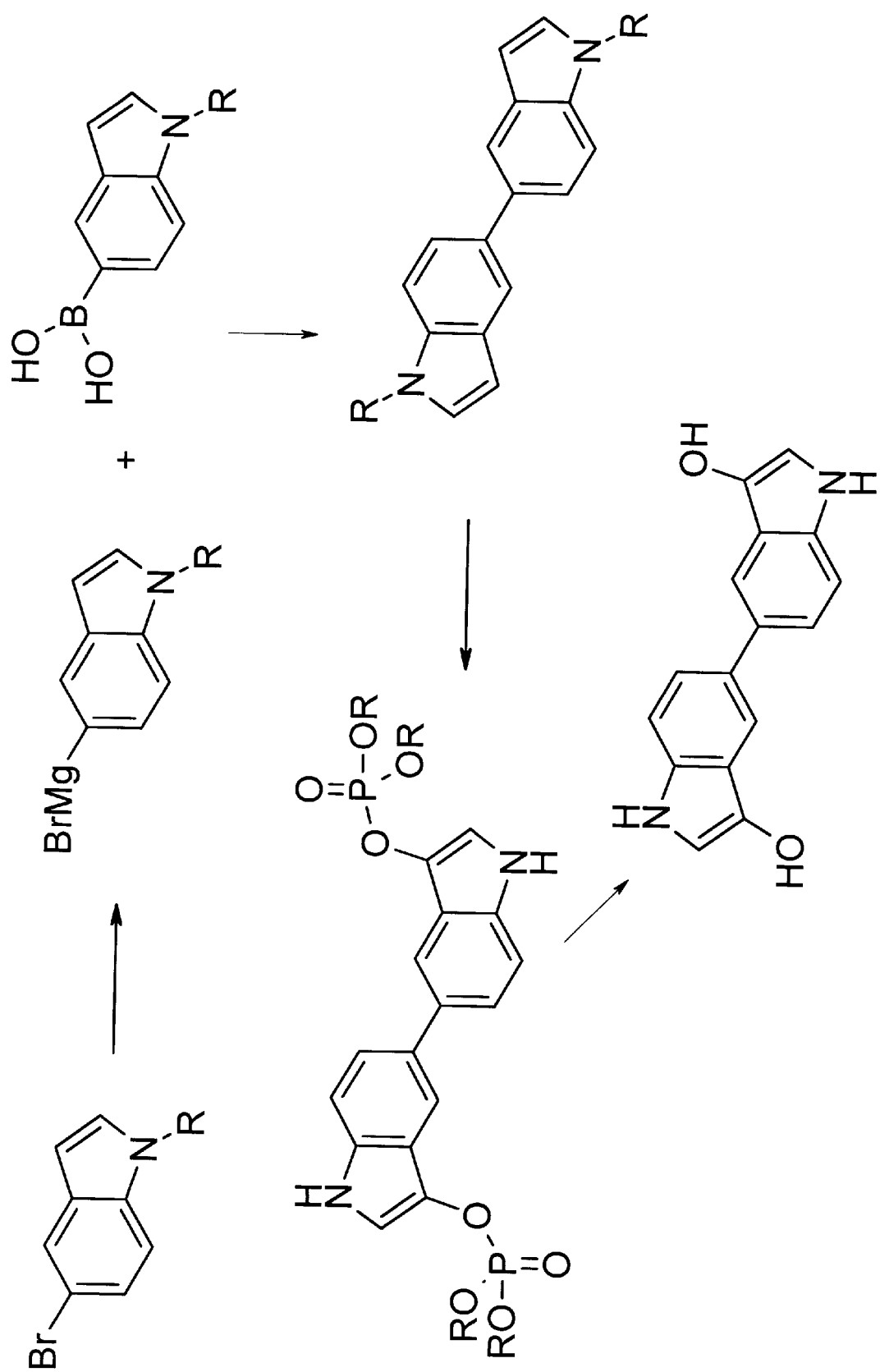
FIG. 17 shows the attachment of 2 indoxyl phosphate via the benzene ring, note that both ends have phosphate groups which can be cleaved.
Figure 19:
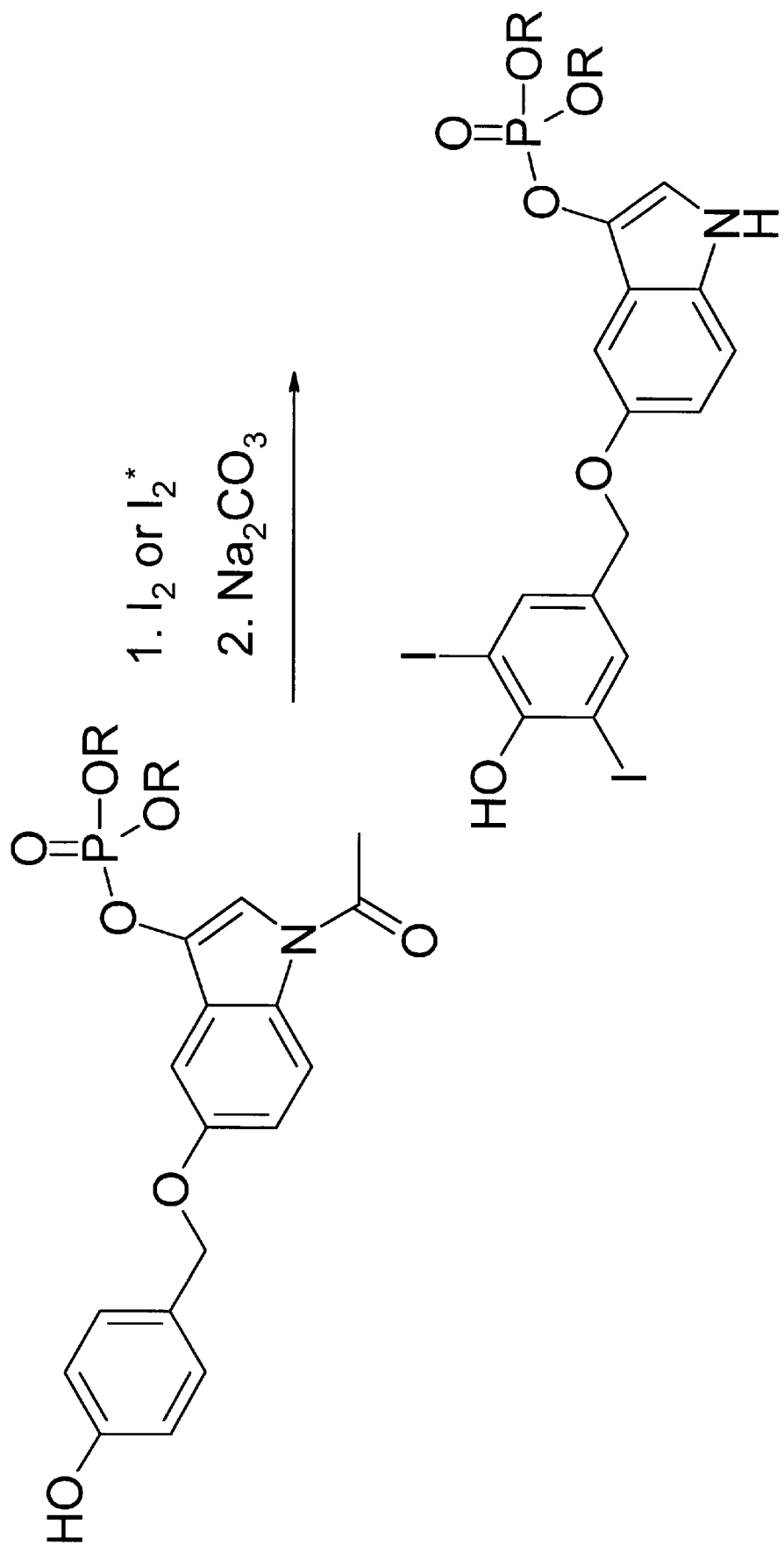
FIG. 19 shows the method of radio-iodinating indoxyl compounds to make iodinated (parahydroxy-benzyl ether of 5-hydroxy indoxyl phosphate).
Figure 20:
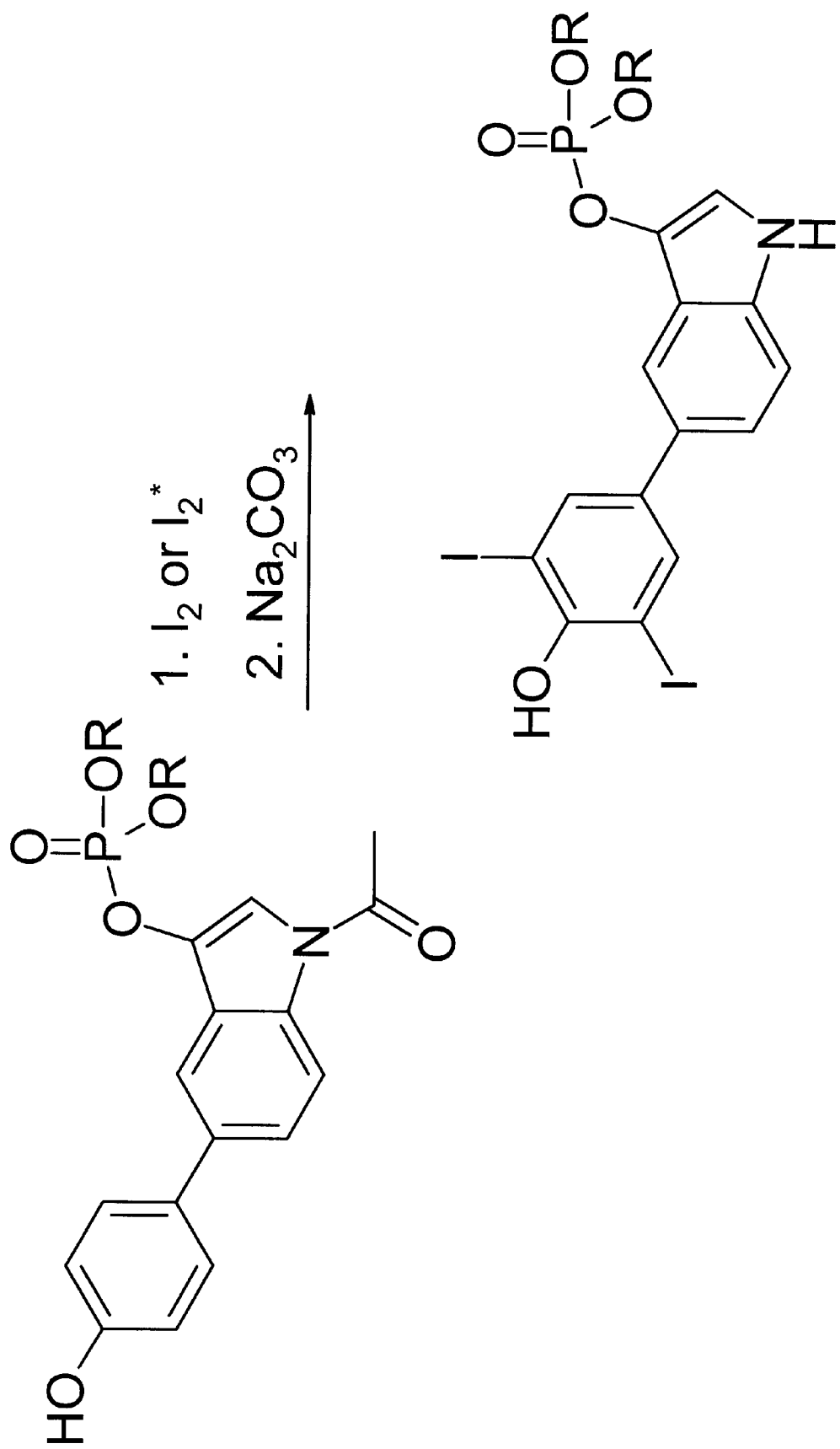
FIG. 20 shows the method of radio-iodinating indoxyl compounds to make iodinated (parahydroxy-phenyl) substituted at the 5 position.

As shown in FIG. 17, a further modification is made by covalently attaching two indoxylphosphate molecules together at a position on the benzene ring to make a bi-indoxylphosphate. Note that both ends have phosphate groups which can be cleaved. Cleavage of the two phosphate bonds of the bi-indoxylphosphate will create a bi-indoxyl molecule which will dimerize with two other bi-indoxyl molecules, and so on, to create a self-assembling linear polymer. The attachment of the two indoxylphosphates can be either direct or indirect via a digestible or non-digestible spacer molecule as illustrated in FIG. 18. The spacer molecule itself can have antigenic epitopes and can be one of several kinds of molecules such as a poly (ethylene oxide) polymer with hetero-bifunctional reactive groups at its terminals (Yokoyama et al, 1992, Bioconjug. Chem. 3, 275–276), a non-degradable copolymer [N-(2-hydroxypropyl) methacrylamide] which is non-immunogenic and has a versatile chemistry which allows for a range of side chains and pendant chemicals such as lactose, mannose, and radio-labeled tyrosinamide. Such molecules have antigenic epitopes and can be introduced to add an additional antigenic epitope to the spacer (Maeda et al, 1992, Bioconug, Chem. 3, 351–362; Seymour, 1992, Critical Reviews in Therapeutic Drug Carrier Systems, 9, 135–187; Primm et al, 1993, J. Drug Target. 1, 125–131) and a hydrophobic hexamethylene spacer group (Ouchi et al, 1992, Drug Des. Discov. 9, 93–105). The formation of the precipitate in the form of an insoluble linear polymer has substantial advantages in reducing the ability of the precipitate to diffuse or move with the convective flow of fluids. In addition, the various antigenic epitopes on the linear polymer can be spaced in an ordered fashion to reduce steric hindrance of antibodies or peptides which can bind to any of the antigenic epitopes (the antigenic epitopes including the first antigenic epitope on the precipitate, the second antigenic epitope on the precipitate, the neo-antigenic third epitope of the indigo precipitate, the antigenic epitopes on the psacer molecule, and the antigenic epitopes on chemicals attached to the spacer molecule).

Additional indoles can be made by attaching chemicals to them at various positions. For example, (a) glycosides can be attached at position 3 to form indole gylcosides, the glycoside can be one of cellobiose which cannot be cleaved by mammalian enzymes and which can be cleaved by a non-mammalian enzyme, (b) all substituents at position 4, 5, 6, and 7, including hydroxyl groups, (c) phenyl at position 5, and all its derivatives, (d) benzyloxy at position 5 and all its derivatives, and (e) 5,5- bi-indoxyls, with or without spacers.

The indoxyl can also be radio-labeled with radioiodine or other radioisotopes. Radio-iodination of the indoxyl compounds can be achieved in three ways: (i) FIG. 19 shows para-hydroxy Benzyl Ether of 5-Hydroxy-indoxyl phosphate is radio-iodinated, (ii) FIG. 20 shows indoxyl with a para-hydroxyphenyl substituted at the 5 position is radio-iodinated, and (iii) FIG. 21 shows the starting material, 1-acetyl-5-iodo-3-hydroxyindole, which is treated with radioactive iodine in 3M HCL. After warming for about 30 minutes, the iodoindole is re-isolated, now containing radioactive iodine. To prepare the tritium labeled compound, the corresponding indole is treated with tritiated water under acid conditions in teterahydrofuran. The indole is re-isolated, in which the aromatic hydrogens have been replaced in part by tritium.

There are four methods of attaching the soluble indoxylphosphate to the protein or peptide targeting agent: covalent bonding, covalent acid labile bonding, non-covalent Van Der Waal forces, and ionic bonding.

Covalent bonding of indoxylphosphate to protein targeting agent is one method of attaching the soluble indoxylphosphate to the protein or peptide targeting agent. In the prior art, it is known that a large number of soluble drugs, antidotes, toxins, dyes, carbohydrates, and other chemicals, have been covalently attached by numerous methods to targeting proteins (Pittman et al. 1983, Biochem. J. 212, 791–800; Mukhopadhyay and Basu 1990, Biotechnology and Appl. Biochem. 12, 529–536; Ali et al. 1990, Cancer Research Suppl. 50, 83–788: Zhong et al., 1992, Biochimica. et Biophysica Acta, 1106, 311–316; O'Hare et al. 1993, J. Drug Target 1, 217–219). The attachment of the targeting agent to the soluble chemical is relatively stable in the extra-cellular fluid so that the attached chemical is mainly released in the lysosome of targeted cells. The attachment of the chemicals to the targeting agent can be achieved without interfering with the binding ability of the targeting agent, or with the function of the chemical after it is detached. In fact, the function of the detached chemical can be maintained even though an amino-acid or peptide "tail" remains attached to the chemical after the main part of the protein has been digested (Novak-Hofer et al, 1995, Cancer Research, 55, 46–50; Duncan and Welch, 1993, J. Nuclear Med. 34, 1728–1738).

In accordance with the invention, the first targeting agent, being the first moiety of the binary reagent can be covalently attached to the soluble indoxylphosphate which is the second moiety of the binary reagent to make the binary reagent. The attachment can be made either at the benzene or pyrrole ring of the indoxylphosphate by a lysosomal enzyme and/or acidic sensitive link. When a critical amount of the targeting protein has been digested by the lysosome enzymes, or when the link between the targeting agent and the indoxylphosphate has been digested, and after the phosphate of the indoxylphosphate has been cleaved by acid phosphatase, free indoxyl molecules will be formed which will readily oxidize. Once in the oxidized form, the indoxyl will spontaneously dimerize to form the highly insoluble indigo dye which will, rapidly and spontaneously precipitate without the need for further enzyme action. Indoxylphosphate can be covalently attached to protein targeting agents in the following ways.

1. The first method of attachment is at site (a) and it can be achieved by to the 3-indoxyl phosphate (0.1 m. mol) in tetrahydrafum (10 ml) is added excess thionyl chloride (10 m. mol) and the solution is warmed to 40 degrees Celsius and kept at that temperature for thirty minutes. It is then evaporated in a rotary evaporator, tetrahydrofuran is added, and then the evaporation repeated. The residue is dissolved in tetrahydrofuran (2 ml) and added to the protein (25 mg.) dissolved in 10 ml of water buffered at pH 7. The mixture is stirred at room temperature for 30 minutes, then lyophilized to cleave the 3-indoxyl phosphate covalently bound to the protein. This material is suitable for addition to the cells.

2. The second method of attachment is at site (a) using a different process from the first method. To the 3-indoxyl phosphate (0.1 m. mol) in water (3 ml) is added the water soluble dimide, 1-(3-dimethylaminopropyl)-3-ethylcarbodimide hydrochloride (0.11 m. mol) in water (2 ml). The solution is stirred at room temperature for 5 minutes and then added to a solution of the protein (25 mg) in 5 ml of water. The resulting solution is warmed to 35 degrees Celsius, kept at that temperature for 10 minutes, then cooled to 20 degrees Celsius. Reverse-phase chromatography, eluting with water-acetonitrile- 1% trifluoracetic acid, gives the pure, covalently bound 3-indolyl-phosphate-protein. Coupling also can be effected by using a linker between the 3-indolyl-phosphate and the protein. This alternative is illustrated in the third method.

3. The third method of attachment is also at site (a). Following the protocol of the first method, the 3-indoxyl phosphate (0.1 m. mol) is converted to the corresponding phosphoryl chloride, which is obtained as the final solution (see first method) in tetrahydrofuran (5 ml). This solution is added to 3-aminopropionic acid (0.1 m. mol) dissolved in water (5 ml), and the mixture is warmed to 50 degrees Celsius for 30 minutes. Evaporation and chromatography on silica, normal phase, gives the B-(3 indolylphosphoryl) aminopropionic acid. This propionic acid is dissolved in water (5 ml), treated with 1-(3-dimethylaminopropyl)-3-ethylcarbodiimide in water (3 ml) in 10 ml of water. Coupling is allowed to proceed for one hour. The solution is then lyophilized and the residue is purified by reverse phase chromatography. The product isolated is the 3-indolyl phosphate linked to the amino group of 3-aminopropionic acid, in turn linked via its carboxylic acid group to the free amino acid groups of the protein.

4. The fourth method of attachment at site (c). In this example, the phosphate group is present as the dibenzyl ester and the substituent on the benzene ring is carboxy. This molecule is treated in Example 2 to form an amide bond with the protein. The phosphate benzyl esters are then converted to phosphate by hydrogenolytic conditions.

An alternative method is covalent, acid labile bonding of indoxylphosphate to the protein targeting agent Various protein targeting agents have been attached to drugs such as 5-Iodo 2-deoxyuridine phosphate (Biessen et al. 1994, J. of Hepatology 21, 806–815) and acyclovir monophosphate (Fiume et al. 1989, Naturwissenschaften, 76, 74–76) via a phosphamide link which is acid labile. The drug phosphates were released in the acidic, enzyme rich environment of the lysosome of cells.

In accordance with the invention, indoxylphosphate attachment to the targeting agent by a phosphamide linkage between indoxylphosphate and lactosylated polylysine or protein is effected using 3-aminopropionic acid as in example C. First the beta-(3-indolylphosphoryl) aminopropionic acid is formed and this is coupled to the lactosylated polylysine, polylysine, or protein as described.

Initial cleavage can be at the indoxyl phosphate bond to directly form the indoxyl which spontaneously precipitates. Initial cleavage can be between the phosphate and amino group which liberates indoxyl phosphate which must then be cleaved to indoxyl. Initial cleavage can be at the protein bond liberates beta-(3-indolylphosphoryl)aminopropionic acid which will then undergo further cleavage to indoxyl or indoxylphosphate.

Direct covalent coupling of antibodies to the soluble precipitable material has some potential disadvantages. For example, the chemical manipulations necessary to make the coupling can (a) reduce or even destroy the specific binding ability of the targeting agent, (b) alter the distribution of the binary reagent in the body, or (c) alter the attached precipitable material which could prevent final precipitation from occurring. In addition, precipitation of the precipitable material will also not occur if the covalent bond between the carrier targeting agent and the precipitable material is not cleaved or if an amino-acid or peptide "tail" remains after partial digestion of the targeting agent For these reasons, the precipitable material has also been attached to the targeting agent by non-covalent Van Der Waal and ionic forces; however, non-covalent bonding has the disadvantage of not being as stable as the covalent linkage. As a consequence of this less stable linkage, the attached precipitable material can disassociate from the targeting agent in the extra-cellular fluid and precipitate prior to (and instead of) precipitating after it has been transported to the lysosomes by receptor mediated endocytosis.

The attachment of the targeting agent can also be achieved by non-covalent antibody or peptide binding to indoxylphosphate by Van Der Waal forces. It is known that a large number of soluble molecules have been bound to their matching antibodies to form soluble binary reagents. This method can be used to form the soluble first binary reagent comprised of indoxylphosphate or other soluble precipitable materials and their matching targeting agent However, in order for the first binary reagent to both target the first target cancer cells and carry the indoxylphosphate, the first binary reagent must be made using a bispecific reagent having two different binding domains. One domain of the bispecific reagent must be able to bind to the endocytosing receptor on the first target cancer cells. The other domain of the bispecific reagent must be able to bind to the indoxylphosphate or other soluble precipitable material. The bispecific reagent can be made by published biological methods (Kohler and Milstein, 1975, Nature, 256, 495–497; Milstein and Cuello, 1983, Nature, 305, 537–540; Webb et al, 1985, Cancer Treatment Reports, 69, 663–672; Suresh et al. 1986, Proc. of the Nat. Acad. Science USA., 83, 7989–7993; Tiebout et al. 1987, J. of Immun. 139, 3402–3405; Urnovitz et al. 1988, J. of Immun. 140, 558–563); chemical methods (Nisonoff and Rivers, 1961, Arch. of Bioch. and Biophys., 93, 460–462; Karpovsky et al. 1984, J. of Expt. Med; 160, 1686–1701; Brennan et al., 1985 Liu et al., 1985, Proc. of the Natl. Acadm. Science USA., 82, 8648–8652; Lansdorp et al., 1986, European J. of Immunol. 16, 679–683; Glennie et al. 1987, J. of Immun., 139, 2367–2375); and genetic engineering methods (Morrison et al., 1984, Proc. of the Natl. Acad. of Sciences USA., 81, 6851–6855; Boulianne et al., 1984, Nature, 312, 643–646 1984).

When the binary reagent binds to the receptor on the cancer cells, it induces receptor mediated endocytosis which transports the binary reagent to the lysosomes. The soluble indoxylphosphate is cleaved and freed from its binding to the targeting agent moiety of the binary reagent by the acidic environment of the lysosomes, aided by an esterase or peptidase which partially or completely digests the protein portions of the binary reagent. The phosphate bond is cleaved by the acid phosphatase in the lysosomes. The cleavage of the phosphate liberates an indoxyl which spontaneously dimerizes and forms a new molecule which is insoluble and precipitates as an indigo dye having a neoantigenic third epitope not present on the indoxylphosphate or the intermediate molecules which are created prior to forming the insoluble indigo.

The fourth method of attachment is via ionic binding protein targeting agent to indoxylphosphoric acid. Since polylysine is basic, it can be attached to chemicals, like indoxylphosphoric acid, to make a salt. This method has been used to attach DNA, antisense DNA, and other nucleotides to polylysine as a step towards targeting these nucleotide reagents to specific cells.

In accordance with the present invention, the ionic method was used to deliver indoxylphosphoric as a salt of lactosylated polylysine to liver cancer cells by making a simple poly-llysine 5-bromoindoxl phosphate conjugate. Poly-L-lysine HBr salt with a molecular weight of 5000–15000 (average molecular weight 8000 by LALLS, 9600 by viscosity), was run through an anion exchange column (Dowex 2-x, 50–100 mesh, OH form generated from Cl form) to remove the toxic bromide anion. After the combined ninhydrin positive fractions were mixed with a solution of indoxylphosphoric acid in EtOAc and MeOH, a precipitate was formed immediately, which was insoluble in water and other organic solvents. FIG. 22 shows the chemical structure of the salt of polylysine and indoxylphosphoric acid.

No water soluble product was obtained when the ratio of indoxyl phosphate to poly-L-lysine was changed gradually from 5 mol %: 100 mol % (based on lysine residue) to 50 mol%: 100 mol %. While an increasing solubility of bromoindoxyl was observed in the presence of NaCl, a large amount of NaCl was necessary to dissolve bromo-indoxyl in the solution (10 mg of bromo-indoxyl in 10 ml of 0.5 M NaCl) and thus this method was impractical.

Figure 23:
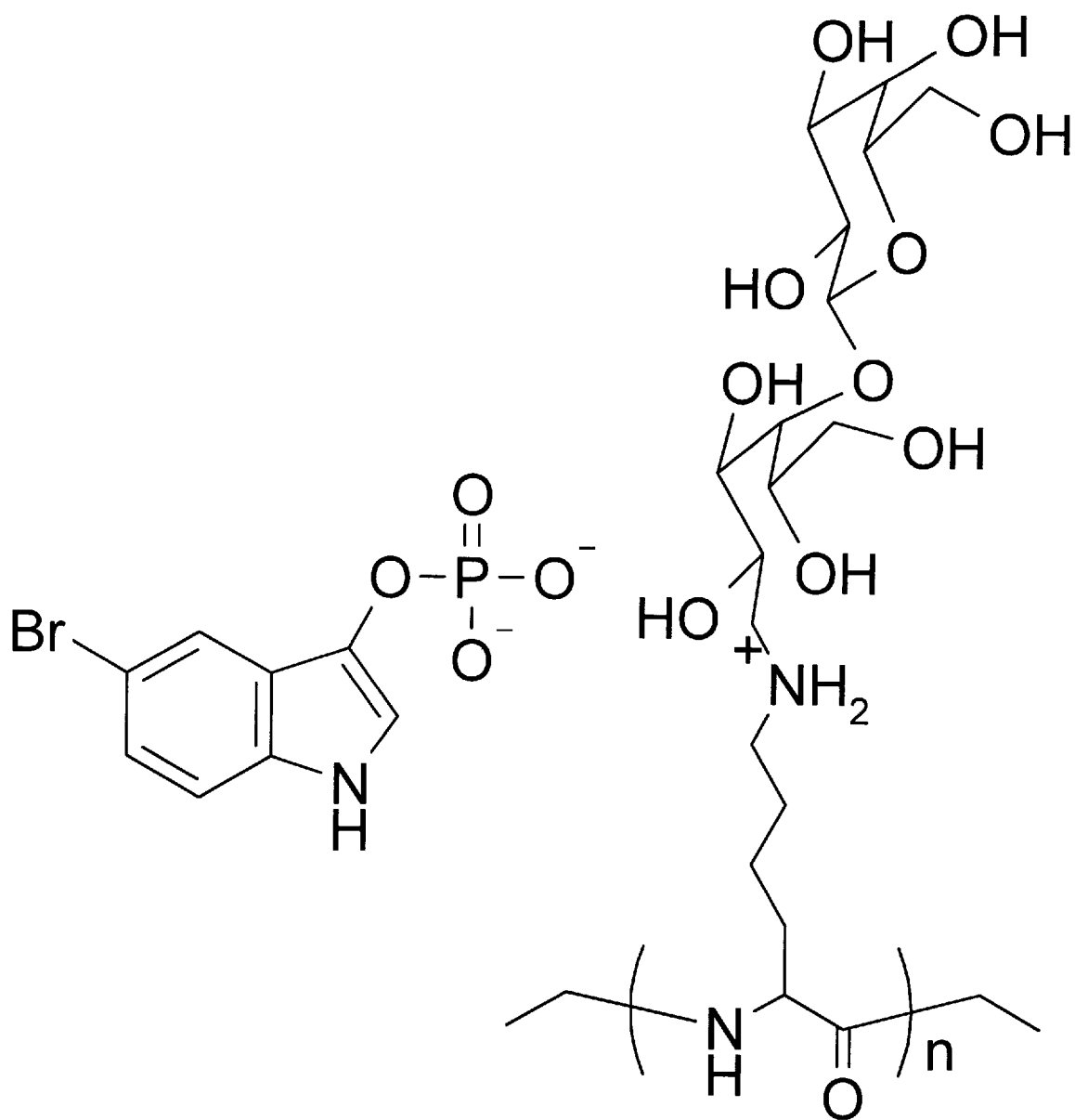
FIG. 23 shows salt of indoxylphosphoric acid and lactosylated polylysine.

Lactose residues on the poly-L-lysine molecule increase the solubility of its conjugates. It was applicable to our system. As shown in FIG. 23 poly-L-lysine was lactosylated with sodium cyanoborohydfide at pH 5.0 to form the acetate of lactosylated-polylysine. A solution of free lactosylated polylysine in water was mixed with phosphoric acid in EtOAc and MeOH solution and the final product was a water soluble white solid. A higher molecular weight poly-L-lysine, with a molecular weight of 15000–30000 (average molecular weight 18000 by LALIS, 19200 by Viscosity) was treated under the same procedure. The final product was still soluble in water, but the solubility was less than that of the product made with the polylysine of lower MW.

The hepatoma cell line, HepG2, which is known to have the specific asialoglycoprotein receptor was grown in tissue culture medium. Because it was found that fetal calf serum contained phosphatase enzyme which reacted with the lactosylated polylysine-indoxylphosphate to cause indigo to precipitate in the medium, the cells were grown in the absence of fetal calf serum. Experiments showed that under these conditions, and in the absence of the HepG2 cells, precipitation did not occur. The HepG2 cells were cultured in duplicate cultures for 5 days in plastic ware (Falcon) at 37 degrees centigrade under 5% carbon dioxide and 95% air in medium, containing 5 milli-molar concentration of the lactosylated polylysine-indoxylphosphate. At the end of the culture period, the cells were washed 3 times in balanced salt solution and harvested. The cells were incubated with 0.1 normal sodium hydroxide for 30 minutes at room temperature, then dissolved in liquid scintillation fluid, and finally centrifuged in 2 ml. centrifuge tubes. The indigo blue precipitate was seen as a small pellet made up of small particles approximately 0.1 micron in diameter.

The lactosylated polylysine acts as a specific ligand for the asialoglycoprotein receptor of normal and malignant liver cells. Therefore, for this ligand-cell system, there is no need for a targeting agent to be attached to the lactosylated polylysine. However, in the more general case, a targeting agent would be covalently attached to the polylysine component of the salt to make a binary reagent (Lu et al. 1994, J. of Nuclear Med. 35, 269–275). It is thought that this latter method can allow for the attachment of a large number of drugs to the polylysine without interfering with the binding ability of the protein targeting agent The method of carrying the soluble precipitable material to the lysosomes of targeted cells by non-covalent binding, via a bispecific antibody reagent or ionic binding has some advantages over covalent bonding. Bispecific antibodies are structurally bivalent but functionally univalent for each antigen binding site. The univalent attachment of the antibody to the cell receptor, compared to the attachment of bivalent antibodies, minimizes antigenic modualtion (Glennie et al., 1988, J. of Immunol., 141, 3662–3670). One manifestation of modulation being a loss of binding sites (Gordon and Stevenson, 1981, J. of Immunol., 42, 13–17: Cobbold and Waldmann, 1984, Nature, 308,460–462). Non-covalent bonding also does not chemically alter the indoxylphosphate and does not interfere with the binding ability of either of the two binding sites of the bispecific antibody. Non-covalent binding allows the indoxylphosphate to be easily detached from the antibody or peptide to which it was bound. The detachment process cannot leave an amino-acid or peptide "tail" on the detached indoxylphosphate which might otherwise interfere with the subsequent ability of the phosphatase enzyme to cleave the phosphate bond to form the indoxyl and to precipitate. However, non-covalent bonding has the disadvantage that the bonding is not as stable as covalent bonding and can disassociate in the body fluids prior to its transport to the targeted cells and prior to its receptor mediated endocytic ttrnsport into the lysosomes of the targeted cell.

Other soluble chemicals can be attached to the targeting agent. When these other chemicals are detached and free, they can polymerize oxidatively, thermally, or photochemically to form an insoluble chemical which precipitates. For example strategically substituted porphyrins can be photochemically polymerized; 5,6-dihydroxyindole oxidatively polymerizes to form insoluble melanin and phenothiazines can be converted to insoluble methylene blue-like molecules.

Figure 24:
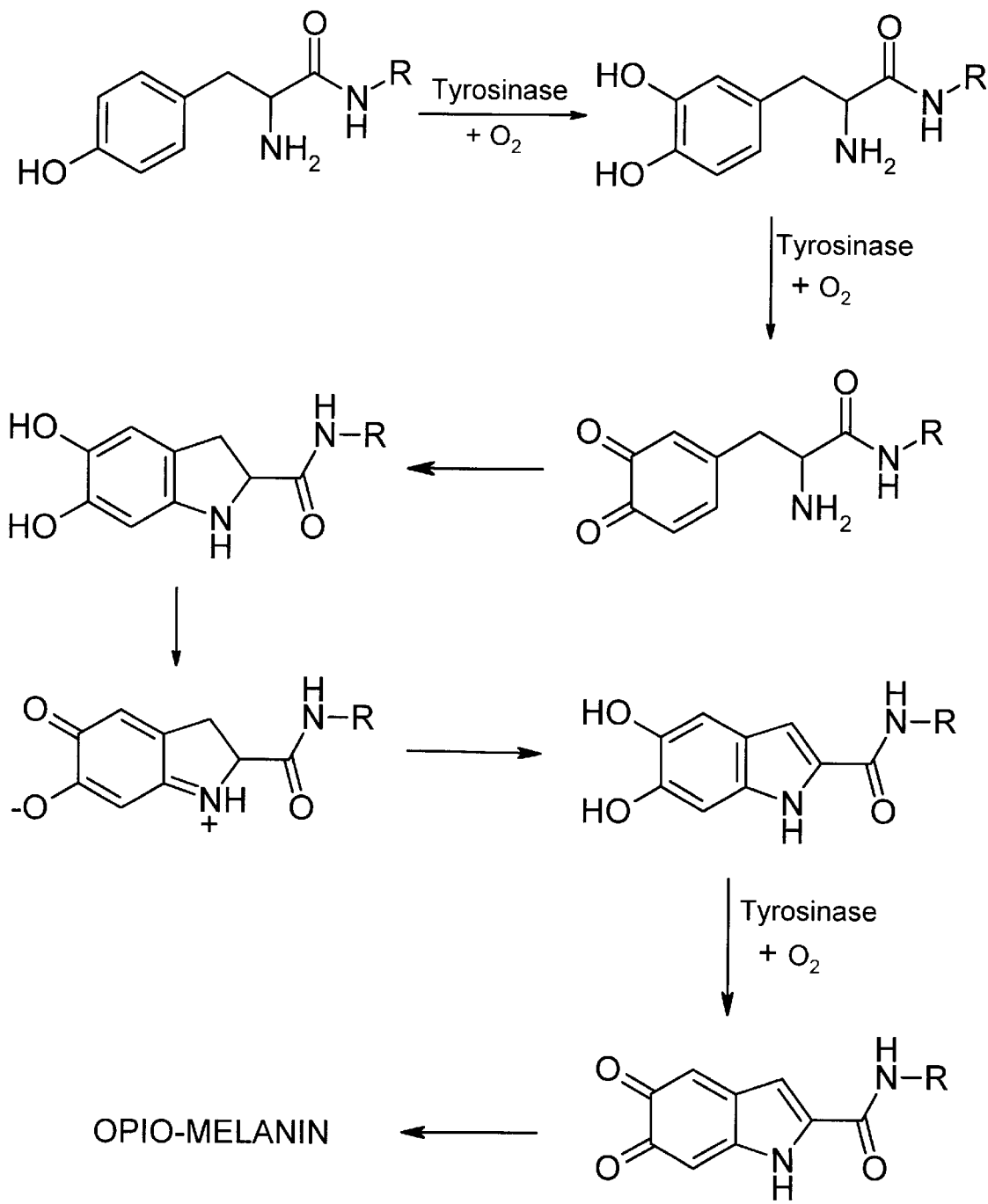
FIG. 24 shows the steps leading to the synthesis opiomelanin.
Figure 25:
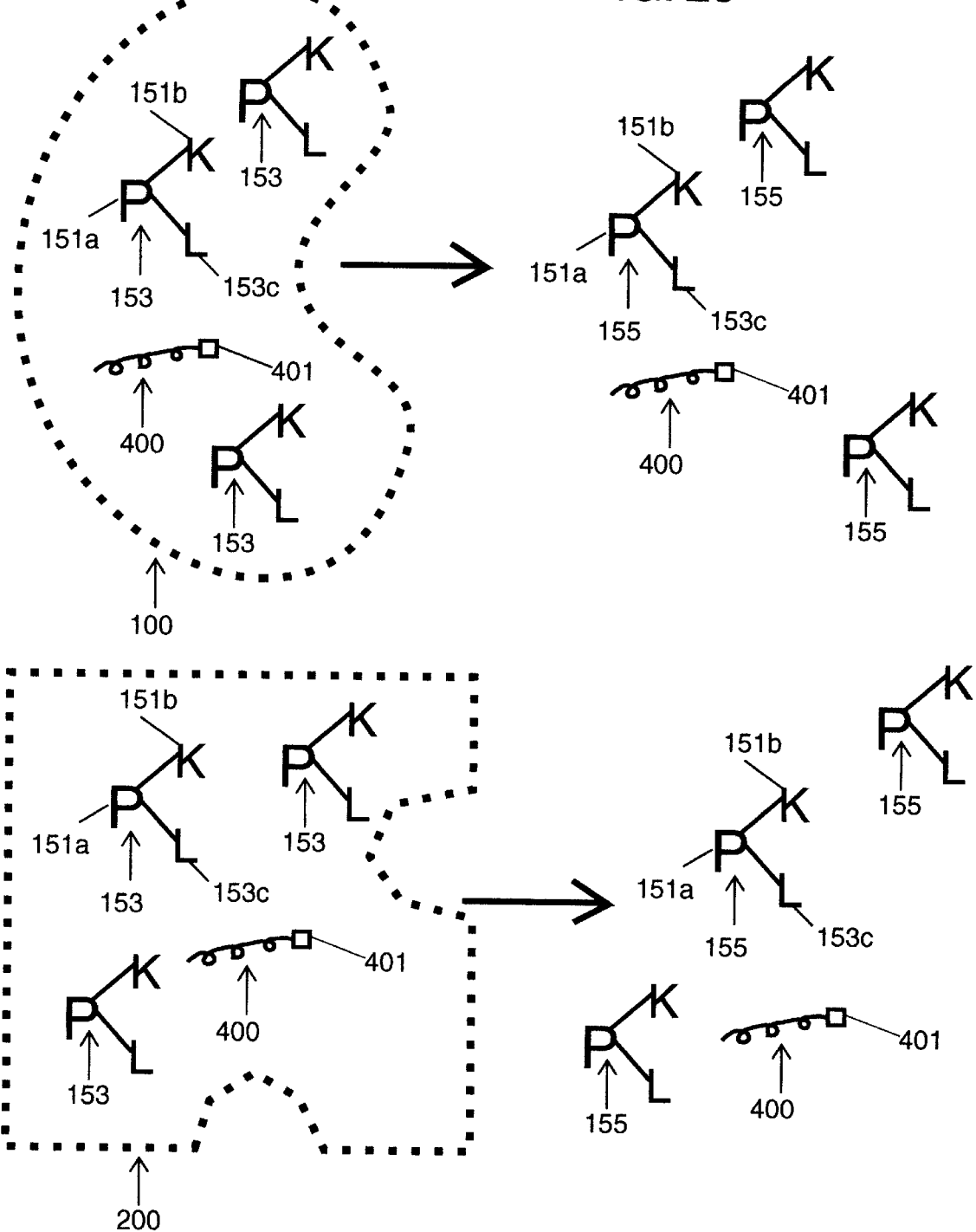
FIG. 25 shows the first therapeutic agent killing the first target cancer cells and first target normal cells relocating the accumulation of precipitate and the natural intra-material to extra-cellular fluid.

A further method of making a soluble precipitable material includes a method in which a domain of a soluble peptide or amino-acid moiety of a soluble peptide is converted into an insoluble material, the peptide remaining soluble because of the solubilizing effect of the unchanged peptide moiety. However, if the unchanged peptide moiety is digested, the converted material being insoluble will precipitate. FIG. 24 is an illustration of a specific example of such a system. The Mason-Rapier pathway for the formation of opio-melanins by the tyeosinase-catalyzed oxidation of opiod peptides, where R represents the peptide chain, where the use of opioid peptides which can be converted by mushroom tyrosinase into melanin-like compounds, retaining the peptide moiety to make opio-melanins which are soluble owing to the presence of the linked amino-acids (Rosei et al 1991, Biochem. Biophys. Res. Commun. 179, 147152). The soluble enkephalin-generated melanins can be covalently attached to the targeting agent in aqueous medium and when the targeting agent is digested and/or the opio-peptide is cleaved by carboxypeptidase A, an insoluble melanin like material is released and precipitates. Enkephalins as well as other opioid peptides including alpha-endorphins, kyotorphin and esorphins, if oxidized in the presence of DOPA and tyrosinase, are readily incorporated into DPOA-melanin. The resulting mixed melanins, opio-melanin plus DOPA-melanin, in contrast to the first example are insoluble and can be solubilized in hydrophilic solvents (Rosei et al 1994, Biochemica et Biophysica Acta, 1199, 123–129), and attached to the targeting agent in this medium. After the targeting agent and enkephalins are digested, the mixed melanins are released as an insoluble material which will precipitate. An advantage of these materials is that they can be made as fusion proteins by genetic engineering which avoids the necessity of attaching the targeting agent to the precipitable material.

Another alternative method of accumulating a precipitate in targeted cells is when the soluble precipitable material comprises two soluble chemicals being a third and fourth soluble chemical, each chemical being attached to a targeting agent, the targeting agent being the same for each of the soluble chemicals, the two soluble chemicals, being detached from the targeting agent by at least one of the lysosome enzymes, react with each other to form a precipitate within the targeted cells. An example of two such soluble precipitable chemicals is the precipitation which occurs when two oppositely charged synthetic linear water-soluble polyelectrolytes, poly-N-ethyl-4-vinyl-pyridine as the polycation reacts with polymethacrylate as the polyanion (Dzantiev et al, 1994, Immunology Letters, 41, 205–211). Another example is the attachment of both an easily oxidized substance, such as polyphenol and a peroxide, to the same targeting agent so that both functions are blocked. Digestion of the targeting agent then liberates both functions which react with each other and form insoluble substances.

Accumulation of a precipitate in targeted cancer cells can also be achieved by introducing into the targeted cell a binary reagent where the soluble precipitable material, being detached from the targeting agent, reacts with a product produced endogenously by the targeted cancer cells to produce an insoluble, relatively non-digestible complex. Tilorone, acridine orange, and other substituted dicationic compounds induce the accumulation in lysosomes of the complex formed by the reaction between tilorone, acridine orange and other substituted dicationic compounds and the endogenously produced glycosaminoglycans by forming insoluble complexes which are relatively non-digestible by glycosidases and which precipitate in the lysosomes (Lullmann-Rauch R. et. al 1995, Biochem. Pharmacol. 49, 1223–12333; Fischer J, 1995, Biochem. J. 312, 215–222). In a similar way, amiodarone complexes to phospholipids and causes the accumulation of the relatively non-digestible and insoluble amiodarone-phospholipid complex. A linear correlation exists between the cellular amiodarone levels and phospholipid accumulation suggesting a stoichiometric relationship and D-alpha-tocopherol (vitamin E) reduces the accumulation of the amiodarone induced accumulation of the phospholipid (Honegger U. E. et al, 1995, Biochem. Pharmacol. 49, 1741–1745; Palmeri S et al, 1995, Life Sci., 57, 1963–1971).

The second class of soluble prrcipitable materials are composed of a soluble moiety attached to an insoluble moiety. It is known that the covalent and non-covalent attachment of small insoluble molecules to proteins, polymers, or conjugates of proteins and polymers can solubilize the otherwise insoluble chemicals. The solubilizing process is illustrated by the following examples. Specific plasma proteins are known to solubilize and carry a variety of relatively insoluble molecules such as steroids, vitamins and other substances in the blood and to release them at the target site. For example, free carotenoids are insoluble in aqueous medium, but non-covalent complexes of carotenoids with protein are soluble and stable over a the pH range 5.0 to 8.5 (Zagalsky P. 1995, Carotenoids Volume 1A, Isolation and Analysis, Birkhauser Verlag Basel P. 287–230). Covalent conjugates of albumin with poly (alkylene oxide) solubilize the otherwise insoluble riboflavin ester benzaflavin (Topchieva et al. 1993, Biotechnology Appl. Biochem. 17, 337–348).

The second class of soluble precipitable material has a soluble moiety attached to an insoluble moiety, and being soluble in aqueous medium this class of soluble precipitable material can be attached to a protein targeting agent by conventional methods to make a soluble binary reagent. The second class of soluble precipitable materials can be made by two methods. In the first method, the aqueous insoluble moiety is attached to the soluble moiety in an organic solvent in which both the aqueous soluble moiety and aqueous insoluble moiety are soluble and stable, the complex material being aqueous soluble and being the soluble precipitable material. In the second method, the aqueous insoluble moiety is first treated while it is an insoluble substance, or in an organic solvent while in solution to remove the insolubilizing groups, to become an aqueous soluble material. The organic solvent is replaced with an aqueous medium and the now soluble material is attached to the soluble moiety to make a soluble material which is treated chemically or enzymatically to replace the insolubilizing groups without markedly reducing the aqueous solubility of the treated material, which is now the soluble precipitable material and can be attached to the targeting agent to make a soluble binary reagent. The formation of a precipitate from the second class of soluble precipitable material requires an enzyme in the lysosomes and/or the acid environment in the lysosomes of the target cells to detach the soluble non-toxic precipitable material from its attachment to the targeting agent. The detached soluble precipitable material is acted on by an enzyme in the lysosomes and/or the acid environment of the targeted cells to detach the soluble moiety of the soluble precipitable material from its attachment to the insoluble moiety thereby causing the insoluble moiety to precipitate. The detachment of the insoluble moiety can be achieved by three methods. In the first method an enzyme in the lysosomes digests the soluble moiety of the soluble precipitable material thereby dissipating the solubilizing effect of the soluble moiety, the remaining material being an insoluble material spontaneously precipitates. In the second method an enzyme in the lysosomes cleaves the soluble moiety thereby eliminating the solubilizing effect of the soluble moiety, the remaining material being insoluble spontaneously precipitates. In the third method the soluble moiety of the soluble precipitable material is attached to a peptide moiety with a substantial affinity for the insoluble moiety and when the peptide moiety of the soluble moiety is partially digested by enzymes in the lysosomes of target cells, the binding affinity of the peptide moiety of the soluble moiety is dissipated thereby detaching the soluble moiety and eliminating the solubilizing effect of the soluble moiety, the remaining material being insoluble spontaneously precipitates.

The choice of the insoluble, small, non-digestible molecule could have a broad range and include porphyrins, alkaloids, polynuclear compounds, insoluble carbohydrates, and natural and synthetic polymers.

A specific example of the second method of dealing with an insoluble precipitable material is the application of chitin, (as an example of X+Y). Chitin is a highly insoluble molecule even when it has a low degree of polymerization (DP). Chitin can be solubilized by enzymatically or chemical deacetylation (removing Y) to form chitosan (X). Chitosan, a copolymer derived from the abundant natural polymer chitin, is composed of 2-amino-deoxy-D-glucose and 2-acetamide-2-deoxy-D-glucose units. Chitosan is soluble in water and can be depolymerized by nitrous acid (G. Graham Allan and Mark Peyron 1995, Carbohydrate Research, 277, 257–272) and by the action of chitinase (Usui T. et al. 1987, Biochim. Biophys. Acta, 923, 302–305) to generate oligomers of any required size. The soluble chitosan (X) with a degree of polymerization of 10–14 can be attached by conventional means in aqueous medium to a polymer of polyproline (P) of sufficient molecular size. The complex material (X+P) can be derivatized with acetic anhydride, without derivatizing or affecting the solubilizing effect of the acetic anhydride-resistant polyproline (P). The acetic anhydride re-acetylates the complex (adds Y to the chitosan component of the complex material) to form a chitin which remains soluble because of its attachment to the unchanged hydrophilic polyproline. The chitin material (X+Y) will remain soluble even though the chitosan (X) component of the material has been converted to chitin (X+Y) because of the solubilizing effect of the unchanged hydrophilic polyproline (P). The soluble precipitable material attached to the polyproline (X+Y+P) can now be attached to the targeting agent by conventional means in an aqueous medium to form a soluble binary reagent. The soluble binary reagent is transported by receptor mediated endocytosis to the lysosomes of the targeted cells. After the attached solubilizing polymer and targeting agent have been sufficiently digested by lysosomal enzymes, or after the bond between the chitin and the attached solubilizing polymer and targeting agent has been cleaved, their solubilizing effect will be dissipated, and the chitin portion of the binary complex, with or without an amino-acid or peptide "tail" left after the incomplete digestion of the targeting agent, will return to its insoluble state, and being insoluble and non-digestible, the chitin precipitates without the need for further enzyme action. Modifications of the chitin can be made to achieve certain characteristics. For example, chitin, can be made more aqueous soluble and more easily digested by mammalian and non-mammalian enzymes by a lower degree of chitosan acetylation.

Another specific example of an insoluble precipitable material is cellulose which is a linear polymer of anhydroglucose units linked by beta-1-4-glycosidic bonds. Insoluble microcrystalline cellulose can be converted into cello-oligomers of different sizes or different degrees of polymerization or DP (Kleman et al. 1994, Biochem 3021 463–469). Non-catalytic cellulose binding proteins (CBD) of MW 10,000 to 15,000 have been isolated and characterized. The gene coding for this peptide has been isolated and inserted into the genome of several cell types so that large quantities can be harvested. The CBD binds, virtually irreversibly, by Van Der Waal forces to high DP (degree of polymerization) cellulose and with a lower affinity to cellulose as small as 5 DP (Tomme P et al 1994, Protein Engineering, 7,117–123; Ferreira L. M. et al., 1993, Biochem. J. 204,349–355).

Celluloses with a DP of 7-10 are highly insoluble in water but are soluble in DMSO. CBD can bind to cellulose of DP 7- 10 in DMSO. A complex of a solubilizing polymer covalently attached to the CBD will also bind to a small DP cellulose in DMSO to create a soluble complex (cellulose+CBD+solubilizing polymer). After creating this complex in DMSO, the DMSO can be replaced with an aqueous medium, and the now soluble complex can be covalently attached in an aqueous medium to the protein targeting agent, by conventional methods, to form a soluble binary reagent. The soluble binary reagent can be administered to the living host and will bind to the receptors on targeted cells. After receptor mediated endocytosis and lysosomal enzyme processing, the CBD is partially or completely digested which will release the small insoluble molecule of cellulose which will immediately precipitate and again has the ability to bind to the CBD peptide. Any cellulose or chitin which forms a precipitate in the extra-cellular fluid without having been endocytosed inside cells can be digested by the administration of the appropriate cellulase or chitinase enzyme. The digestion of the cellulose or chitin is analogous to the digestion of fibrin by the administration of tissue plasminogen activating factor.

Another specific example of an insoluble precipitable material is the thermo-reversible polymer of poly (N-isopropylacrylamide) which has been synthesized with carboxyl functional end groups. The polymer is soluble below a critical temperature, and at this temperature, it can be attached in aqueous medium to the targeting agent by conventional methods, to produce an aqueous soluble binary reagent (Chen and Hoffman 1994,5, 371–382). A small increase in temperature causes the polymer to become insoluble, but the binary reagent will remain soluble by the solubilizing effect of the targeting agent with or without the aid of an attached solubilizing polymer such as polyethylene glycol. The soluble binary reagent can be delivered to the lysosomes of targeted cells where the solubilizing effect of the targeting agent and solubilizing polymer will be dissipated and the thermo-reversible polymer will precipitate.

The exemplary examples outlined above are directed towards achieving the accumulation and trapping of a relatively non-digestible precipitate in the lysosomes of targeted cells. In all these cases the primary requirements are that the carrier targeting agent to which the precipitable material is attached be recognized by, and will bind to the targeted receptors like the native protein, and there is adequate accumulation and retention of the precipitate in the targeted cell, with virtually zero redistribution of the precipitate to non-targeted cells.

As shown in FIG. 25, according to the method of the present invention, following the accumulation of precipitate inside the first target cancer cells and inside the first target normal cells, is the step of administering to the living host the first therapeutic agent which causes a cell-killing process capable of killing the first target cancer cells 100 and the first target normal cells 200 and thereby causing the accumulation of the precipitate 153 having the plurality of antigenic epitopes to be relocated into the extra-cellular fluid adjacent to the first target cancer cells and to the first target normal cells, the relocated precipitate now becoming a first extra-cellular precipitate 155 and having the first antigenic epitope 151*a*, the second antigenic epitope 151*b*, and the neo-antigenic third epitope 153*c*, the relocated accumulation of precipitate 155 thereby having the plurality of antigenic epitopes, the cell killing process further causing the natural intra-cellular material 400 having antigenic epitopes 401 to be relocated into the extra-cellular fluid adjacent to the first target cancer cells and the first target normal cells.

In accordance with the present invention, selective killing of a fraction of cancer cells is achieved by exploiting the heterogeneity of the tumor cell population. The universal and wide heterogeneity which is found in tumor cell populations is well known. It is expressed in every parameter which has been measured in cells, including a heterogeneity in their sensitivity or resistance to being killed by an untoward environment. This untoward environment includes all current agents which are used in an attempt to kill cancer cells, as well as the environment created by the natural system of the living host. As a result of this heterogeneity, it is likely that there will always be some cancer cells which are super-resistant to being killed prior to the administration of any of the current therapeutic agents. Cancer cells that survive the first administration of a therapeutic agent become resistant to later administrations of therapeutic agents by a process of cell adaptation. Because these super-resistant cells are a major obstacle to current therapeutic approaches, a significant amount of research has been devoted to them.

However, heterogeneity of the cancer cells expresses itself, not only by the presence of super-resistant cells, but also by the presence of cells which are super-sensitive to being killed. These cancer cells have so many gene errors that they are killed by low doses of the current therapeutic agents or by other cell killing processes. Normal cells do not have these gene errors so that few normal cells (if any) are super-sensitive. Therefore, few normal cells are killed by the very low doses of agents which kill super-sensitive cancer cells.

Current research and therapy regimens ignores the presence of these super-sensitive cancer cells because these cells are of no scientific interest or practical value in the context of current therapies. In contrast, the approach of the present invention exploits the presence of super-sensitive cancer cells and kills them selectively by administering the first therapeutic agent which causes a cell killing process. The first therapeutic agent may include the administration of low doses of anti-cancer agents which are currently available, and preferably which cause lysis of cell membranes.

Theory and data support the view that the low dose selective killing of these super-sensitive cells can be readily achievable. In fact, the frequent presence of dead cells in histological preparations of cancer tissue suggests that some tumor cells are so super-sensitive that they have been killed by various natural host factors which operate at the physiological low levels which prevail in the tumor-bearing subject. It is even possible that in some tumors, the natural host killing is so frequent that no external agent need be administered to achieve the necessary selective killing of the super-sensitive fraction. The presence of super-sensitive cancer cells, reflecting as it does the universal heterogeneity and genetic instability of cancer cell populations, may be the most common, the most specific, and with respect to the method of the invention, the most exploitable characteristic of any cancer. The low dose selective killing of these super-sensitive cancer cells can be considered to be analogous to, or an enhancement of, the natural, continuous, and selective killing of some cancer cells by the defense system of the body.

Death of cells eliminates the normal permeability restrictions to molecules that are characteristic of intact cells and enables molecules like trypan blue and antibodies to gain access to intra-cellular material. For example, labeled anti-myosin antibody can bind to cardiac myosin when the cardiac cells have been killed (Khaw et al., 1987, J. Nuclear Med., 28, 1671–1678), and anti-histone- DNA antibody can bind to histone-DNA complex when cancer (or other) cells are killed (Epstein et al. 1988, Cancer Research, 48, 5842–5848).

The first therapeutic agent is a cell killing process capable of selectively killing cells which have the characteristic being substantially specific to cancer cells and being shared by the first target cancer cells and the first target normal cells. The characteristic being a high sensitivity to, and being killed by, the natural system of the living host, and/or having a high sensitivity to, and being killed by, the first therapeutic agent. The cell killing relocates the intra-cellular precipitate to the extra-cellular fluid to form the first extra-cellular precipitate.

The cell killing process including at least one of the administration any one of numerous anti-cancer cytotoxic drugs or cellular agents at a low dosage so that only cells with the characteristic of having a high sensitivity to being killed by the first therapeutic agent would be killed. The cell killing process also includes non-toxic agents, such as hormones or antihormones, or a procedure, such as orchidectomy, which leads to an alteration in the hormonal status of the living host and causes a cell killing process called apoptosis which is directed against cells of a particular cell lineage which are sensitive to the hormonal status of the living host. For example, orchidectomy and/or the administration of anti-androgens causes the apoptotic killing of a large number of normal prostate cells and a variable number of prostatic cancer cells. Regardless of which cell killing process is employed, the cell killing process is capable of selectively killing at least cells with the characteristic of having a high sensitivity to being killed by the first therapeutic agent.

As discussed earlier, the on-going natural killing of cancer cells by the natural immune system of the body may be sufficient to create sufficient Hot-Spots. The number of Hot-Spots can be enhanced by the application of such very low levels of the cell killing process that few, if any, normal cells will be killed and systemic toxicity can be avoided. The method of the present invention exploits the wide heterogeneity of the cancer cell population, one manifestation of this heterogeneity enables preferential killing of cancer cells that have a high sensitivity to one of the anti-cancer agents, the cells being super-sensitive to being killed, the preferential killing causes preferential relocation to the extra-cellular fluid of the accumulated precipitate from these sensitive cancer cells. Selective killing of a large number of cancer cells is not possible at the present time; however, selective killing of a very small super-sensitive fraction is feasible and can be achieved as described above.

The killing of the super-sensitive first target cancer cells, preferably by lysis, and the first target normal cells causes the intra-cellular accumulated first precipitate to be relocated into the extra-cellular fluid so that the first precipitate is outside the cells and is thus exposed and accessible to reagents delivered later in the therapeutic process to generate Hot-Spots.

Figure 26:
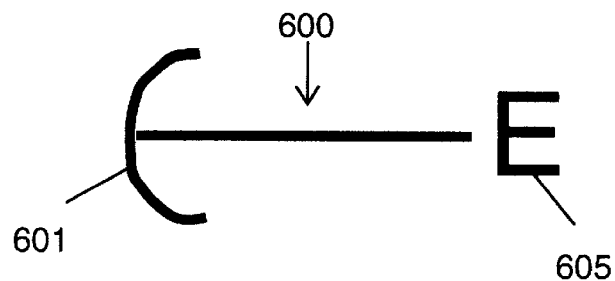
FIG. 26 shows the bispecific reagent, having a non-mammalian enzyme moiety and a targeting agent moiety capable of binding to the first extra-cellular precipitate.
Figure 27:
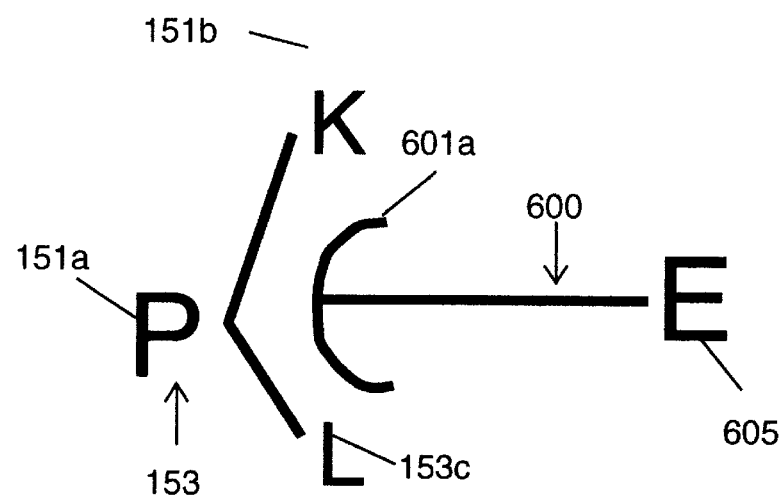
FIG. 27 shows the bispecific reagent binding to the first antigenic epitope of the first extra-cellular precipitate.

The present invention includes the step of delivering into the living host a bispecific reagent. FIG. 26 shows the bispecific reagent 600 having two moieties, the first moiety of the bispecific reagent being a non-mammalian enzyme moiety 605, the bispecific reagent further including a second moiety which is a targeting agent moiety 601 having substantial affinity for at least one of the antigenic epitopes on the first extra-cellular precipitate. FIG. 27 shows an example of the bispecific reagent 600 having two moieties, the first moiety of the bispecific reagent being a non-mammalian enzyme moiety 605, the second moiety being a targeting agent moiety 601a having an affinity for the first antigenic epitope of the extra-cellular precipitate, bound to the first antigenic epitope 151a of the extra-cellular precipitate 155.

Figure 28:
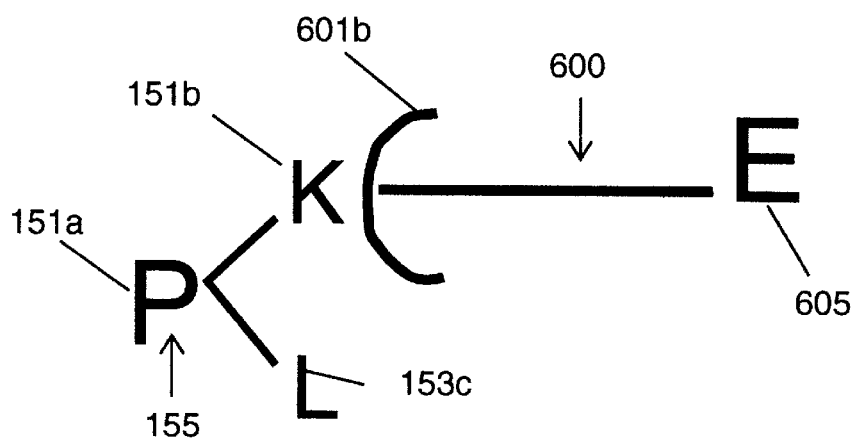
FIG. 28 shows the bispecific reagent binding to the second antigenic epitope of the first extra-cellular precipitate.

FIG. 28 shows an example of the bispecific reagent 600 having two moieties, the first moiety of the bispecific reagent being a non-mammalian enzyme moiety 605, the second moiety being a targeting agent moiety 601b having an affinity for the second antigenic epitope of the extra-cellular precipitate, bound to the second antigenic epitope 151b of the extra-cellular precipitate 155. FIG. 29 shows an example of the bispecific reagent 600 having two moieties, the first moiety of the bispecific reagent being a non-mammalian enzyme moiety 605, the second moiety being a targeting agent moiety 153c having an affinity for the neo-antigenic third epitope of the extra-cellular precipitate, bound to the neo-antigenic third epitope 153c of the extra-cellular precipitate 155 Following the delivery of the bispecific reagent 600, the bispecific reagent is received and bound at the plurality of the antigenic epitopes 151a, 151b, 153c of the first extra-cellular precipitate 155.

As shown in FIG. 27, binding the bispecific reagent to the first antigenic epitope of the first extra-cellular precipitate has the advantage that the first antigenic epitope being a natural portion of the soluble precipitable material simplifies the synthesis of the soluble precipitable material but has the disadvantage that the first antigenic epitope may be difficult or impossible to cleave by the administration of an enzyme. Such cleaving is valuable if a substantial amount of precipitate forms in the extra-cellular fluid in response to the administration of the binary reagent and the presence of some intra-cellular enzymes in the extra-cellular fluid. A further disadvantage of binding the bispecific reagent to the first antigenic epitope is that the first antigenic epitope is also present on the accumulated precipitate inside cells and the first extra-cellular precipitate which requires that the administration of the bispecific reagent be made after all binary reagent has been cleared from the extra-cellular fluid.

As shown in FIG. 28, binding the bispecific reagent to the second antigenic epitope of the first extra-cellular precipitate has the advantage that the second antigenic epitope being a portion of the second chemical which was attached to the soluble precipitable material and is a portion of the intra-cellular accumulated precipitate and a portion of the first extra-cellular precipitate, can be selected to be capable of being readily cleaved by the administration of a non-mammalian enzyme. The use of the second antigenic epitope also has the requirement that the bispecific reagent be administered only after all binary reagent has been cleared from the extra-cellular fluid.

As shown in FIG. 29, binding the bispecific reagent to the neo-antigenic third epitope of the first extra-cellular precipitate has the advantage that the binary reagent and the bispecific reagent and the enzyme which can cleave the neo-antigenic third epitope can be administered during the same period of time, but has the disadvantage that the neo-antigenic third epitope may be difficult or impossible to cleave.

Following the delivery to the living host of the bispecific reagent, some of the bispecific reagent will be in body fluids or bound non-specifically to non-target cells or to extra-cellular structures. It is known that, with time, circulating antibodies and antibodies bound non-specifically, are naturally eliminated from the body of the living host more quickly than antibodies that are bound to specific targets (Henkel et al., 1985, Clinical Immunology and Immunopathology, 35, 146–155: Goldberg et al., 1988, Archives Of Pathology Laboratory Medicine, 112, 580–587). Therefore, the elimination of the bispecific reagent from the living host can be achieved simply by allowing a lapse of time; the elimination of the bispecific reagent can be hastened, as has been described for the second step of the ADEPT process (Sharma et al, 1994, Cancer Supplement, 73, 1114–1120), by the administration of a galactosylated antibody specific for the non-mammalian enzyme moiety of the bispecific reagent . The galactosylated antibody can inactivate the enzyme and/or facilitate the clearance of the enzyme moiety-galactosylated antibody complexes via the galactose specific receptors in the liver.

The elimination, from the living host, of all the bispecific reagent not specifically bound to the first extra-cellular precipitate prior to the administration of the additional therapeutic agent is necessary to prevent the additional therapeutic agent from being converted into the new form in locations other than in the tumor. After all unbound bispecific reagent has been eliminated from the living host the additional therapeutic agent is additionally administered to the living host, circulating freely in the body fluids and being converted by the non-mammalian enzyme moiety of the bispecific reagent.

The location of the first extra-cellular precipitate requires cells to have accumulated precipitate via the administration of the targeted binary reagent and for cells to have been killed via the administration of the first therapeutic agent Since the bispecific reagent is bound to at least one of the antigenic epitopes of the first extra-cellular precipitate, the location where the non-mammalian enzyme moiety of the bispecific reagent converts the radioactive toxic additional therapeutic agent into the radioactive toxic new form which is capable of remaining adjacent to the first extra-cellular precipitate for an extended period of time thereby killing non-selectively all cells adjacent to the first extra-cellular precipitate, is specific to the tumor.

In accordance with the method of the present invention, after all unbound bispecific reagent has been eliminated from the living host, the additional therapeutic agent, which is a soluble radioactive toxic agent is additionally administered to the living host, the additional therapeutic agent to be converted by the non-mammalian enzyme moiety of the bound bispecific reagent into a radioactive toxic new form capable of remaining adjacent to the first extra-cellular precipitate for an extended period of time to kill non-selectively all cells adjacent to the first extra-cellular precipitate. Since the first extra-cellular precipitate is retained in the extra-cellular fluid for an extended period of time and since the bispecific reagent is bound thereto, the continued administration of the additional therapeutic agent enables the non-mammalian enzyme moiety to convert a substantial amount of the additional therapeutic agent into the radioactive toxic new form. The radioactive toxic new form remaining adjacent to the first extra-cellular precipitate for an extended period of time thereby creating an intense field of radiation—called a Hot-Spot—which kills non-selectively all cells adjacent to the first extra-cellular precipitate.

Since the enzymatic conversion of the additional therapeutic agent takes place exclusively in the extra-cellular fluid, there is no need for the additional therapeutic agent to gain entrance into the intra-cellular compartment of the body. Entrance of the additional therapeutic agent into cells throughout the living host increases the volume of distribution of the additional therapeutic agent (the intra-cellular compartment has a volume at least 2–3 times that of the extra-cellular fluid) and increases the duration of time that the additional therapeutic agent circulate s in the living host, both these factors increase the systemic toxicity caused by the additional therapeutic agent. For these reasons it is of significant advantage for the additional therapeutic agent to be cell impermeant by being a molecule larger than 1000 daltons and/or being anionic. Alternatively the additional therapeutic agent can be made cell impermeant by attaching one of a number of cell impermeant molecules at least including peptides or polymers having a molecular size greater than 1,000 daltons and anionic chemicals including thiols.

In accordance with the present invention, there are at least three different methods of retaining the new form of the additional therapeutic agent in the tumor region. Each method of the invention involves the step of delivering into the living host the bispecific reagent and additionally administering to the living host the additional therapeutic agent to be converted by the non-mammalian enzyme moiety of the bound bispecific reagent into a new form to be retained for an extended period of time adjacent to the first extracellular precipitate by at least three different methods.

As shown in FIG. 30, in the first method of retaining the new form of the additional therapeutic agent in the tumor region, the soluble radioactive toxic additional therapeutic agent, being the second therapeutic agent 700 is converted by the non-mammalian enzyme moiety 605 of the bispecific reagent 600 into a new form 701 which is insoluble and which spontaneously forms a radioactive toxic precipitate being the second extra-cellular precipitate 701 and having a neo-antigenic epitope 702 not found on the second therapeutic agent 700, the neo-antigenic epitope 702 enabling the second extra-cellular precipitate 701 to be "tethered" via a previously administered bispecific reagent bound to stable structures in the tumor tissue (as described later). The tethering retaining the second extra-cellular precipitate for an extended period of time adjacent to the first extra-cellular precipitate where the radioactive toxic second extra-cellular precipitate generates intense fields of radiation, called Hot-Spots, which kill non-selectively all cells adjacent to the first extra-cellular precipitate.

The second therapeutic agent to be used in the first method can be a soluble radioactive toxic precipitable agent made by converting chemical X to a soluble XY. The bond attaching X to Y is cleaved by the non-mammalian enzyme moiety of the bispecific reagent to create the highly reactive intermediate molecule Xa. The Xa molecule is readily and extremely rapidly oxidized to form Xb. In the oxidized form, Xb spontaneously and covalently self-condenses or dimerizes to create a new molecule which is insoluble and immediately and spontaneously forms a radioactive toxic second precipitate. Because a new molecule is formed by the dimerization, the core structure of the second precipitate has a neo-antigenic epitope which is not present on the original XY, Xa, Xb or anywhere else in the body.

Figure 31:
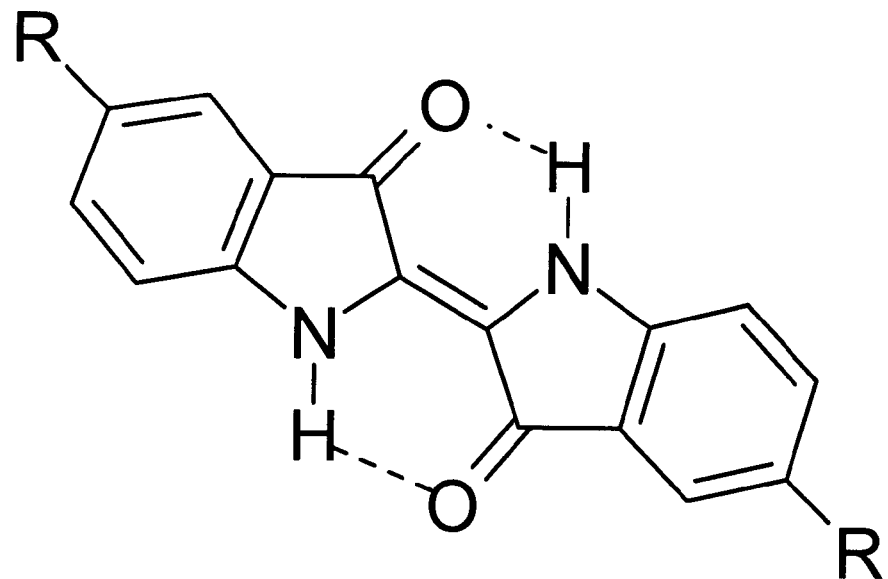
FIG. 31 shows the dimerization of the second therapeutic agent.
Figure 32:
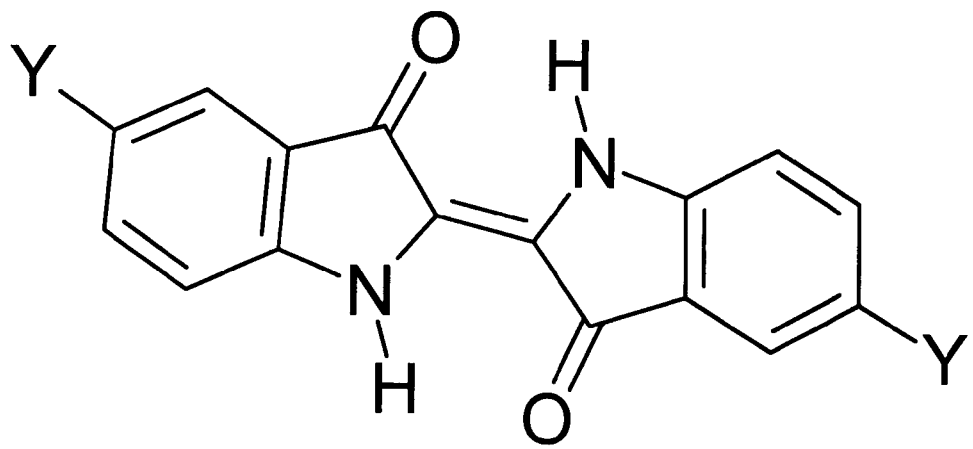
FIG. 32 shows the second extra-cellular precipitate being a radioactive toxic indigo dye.

A specific example of a second therapeutic agent to be used in the first method is the application of a radioactive indoxyl-lactam as examples of XY, which is soluble and can be administered to the living host as a free molecule. The lactam (Y) of the indoxyl-lactam (XY) is cleaved by beta-lactamase enzyme (being the enzyme moiety of the bound bispecific reagent) to liberate a highly reactive intermediate indoxyl (Xa). As shown in FIG. 31 the indoxyl (Xa) is readily and extremely rapidly oxidized, and once in the oxidized form it spontaneously self-condenses or dimerizes to form a new molecule which is insoluble and precipitates spontaneously as a radioactive toxic second extra-cellular precipitate being a radioactive toxic indigo dye as illustrated in FIG. 32 where Y can be aryl, halogen, hydoxyl, and alkyl. The new molecule is different from the indoxyl-lactam and the intermediate indoxyl molecules and thereby having a neo-antigenic epitope not present on the indoxyl-lactam or the indoxyl intermediate.

Figure 33:
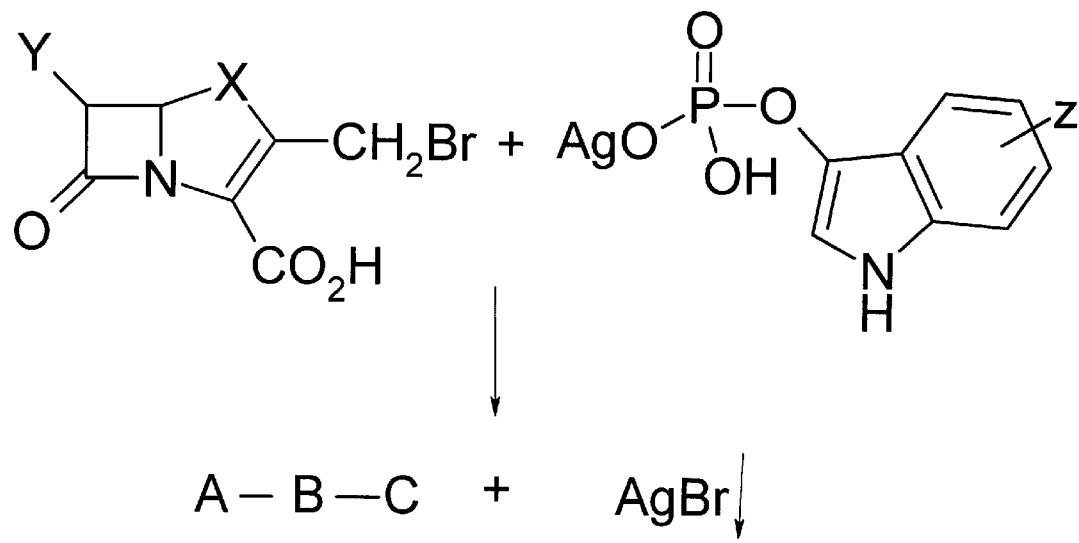
FIG. 33 shows the method of attaching penicillin to indoxyl phosphate at position 3 via phosphate group.
Figure 34:
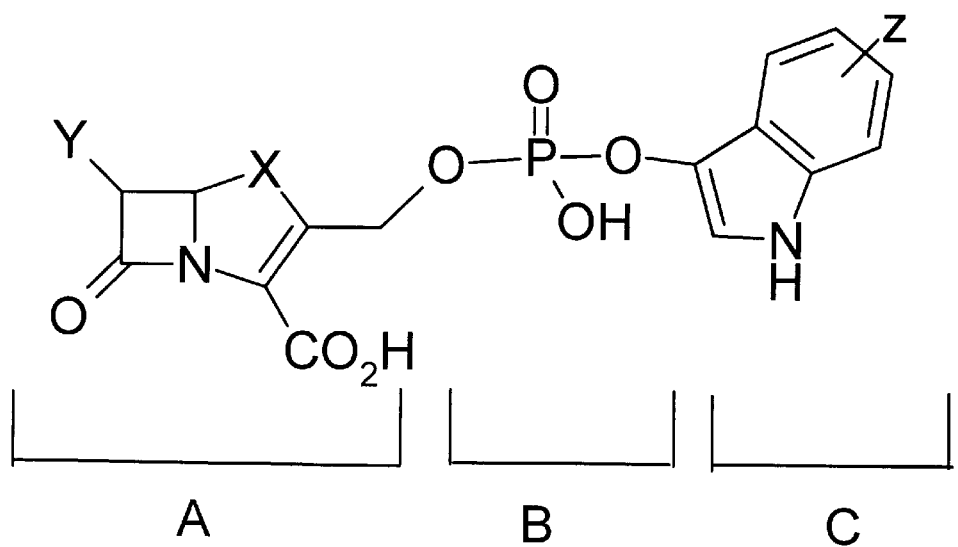
FIG. 34 shows penicillin attached to indoxyl phosphate at position 3 via phosphate group.
Figure 35:
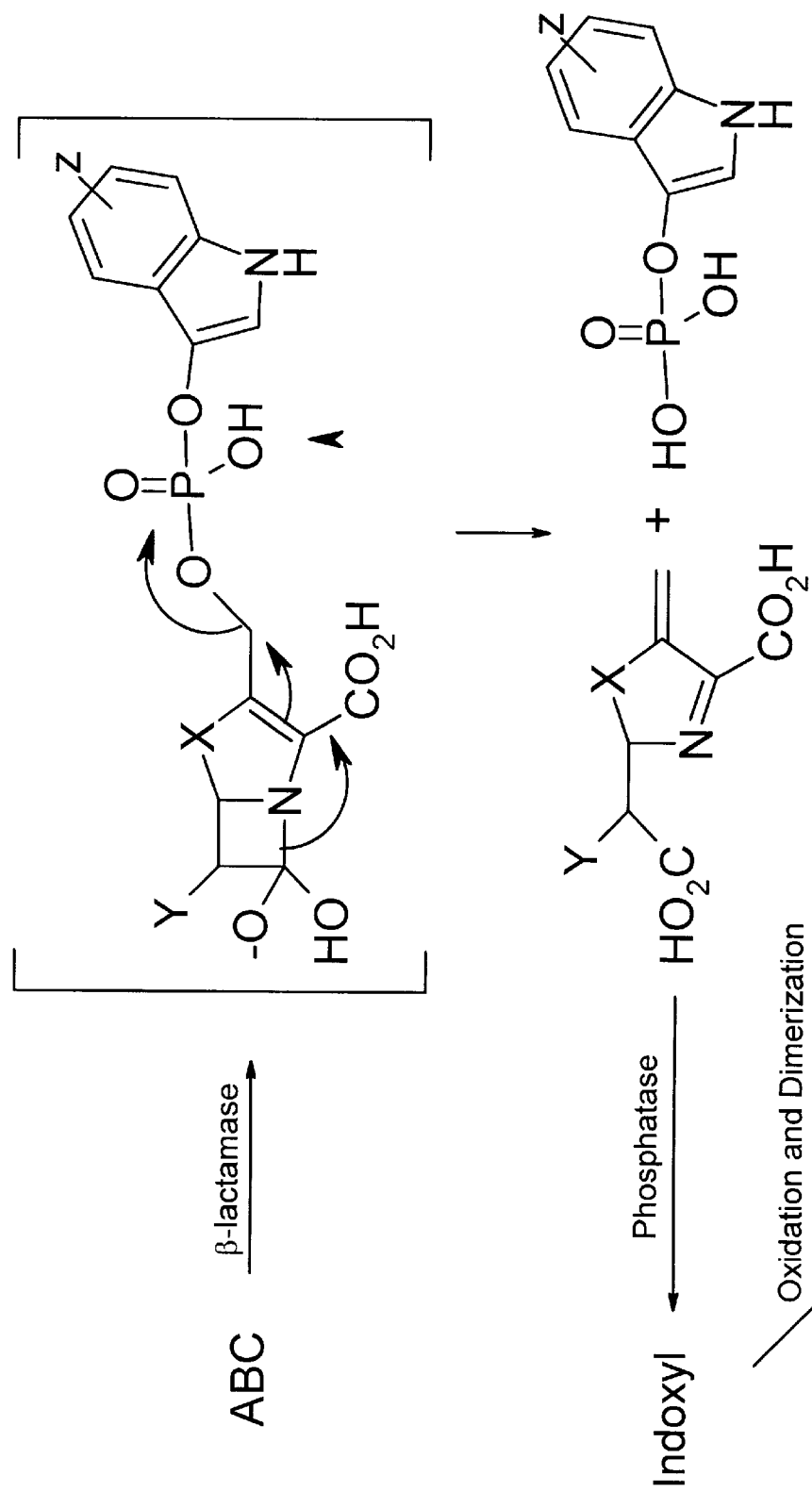
FIG. 35 shows the liberation of indoxyl phosphate from A-B-C and its precipitation by phosphatase.
Figure 36:
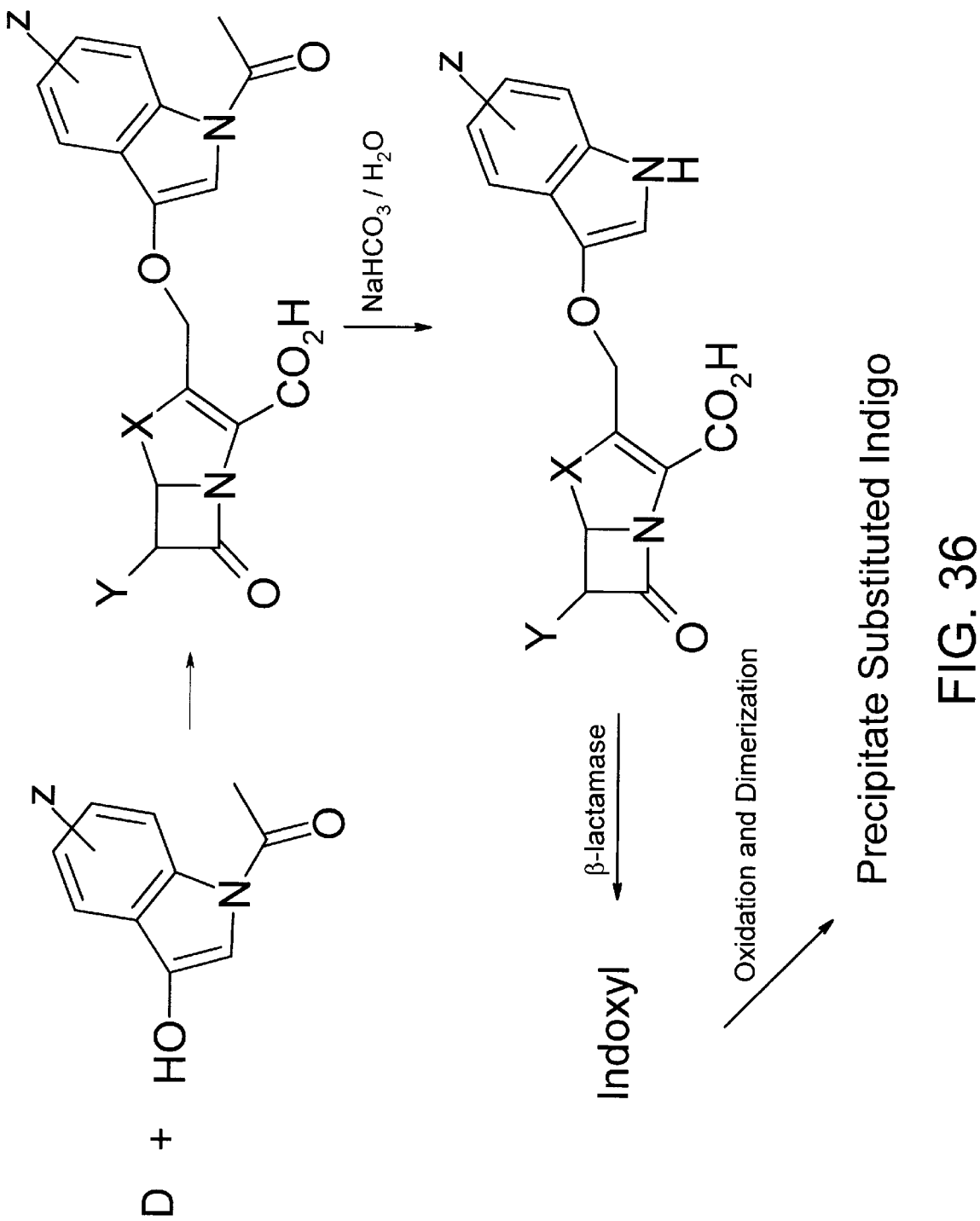
FIG. 36 shows the attachment of penicillin directly to indoxyl which is then treated; beta lactamase liberates indoxyl which forms a precipitate.

FIG. 33 and FIG. 34 where Y is a typical penicillin at the 6 position, where X is oxygen, sulfur, or carbon, where Z is an appropriate substitute in the indoxyl which allows attachment to targeting agent, alternatively attachment to the targeting agent may be effected through Y, where B is the phosphate (as will be shown similar events may occur with or without the phosphate group), and where C is the substituted indoxyl portion that, when liberated, dimerizes and precipitates. As shown in these diagrams, the lactam can be attached to position 3 of the indoxylphosphate via the phosphate group, in which case it is detached by beta-lactamase to form indoxylphosphate. As shown in FIG. 35 the phosphate group of the remaining indoxyiphosphate is cleaved by phosphatase naturally present in body fluids to produce indoxyl which passes through the steps previously described to precipitate. FIG. 36 illustrates how the lactam can also be attached directly to the indoxyl at position 3, in which case precipitation occurs by the direct action of beta-lactamase.

The oxidation and dimerization of indoxyl proceeds at as lower rate in the acidic pH which is often present in the extra-cellular fluid of the tumor tissue, compared to the rate of oxidation and dimerization in the relatively neutral pH found in the extra-cellular fluid of normal tissues. The slower rate of oxidation and dimerization may allow some of the soluble indoxyl molecules and intermediates to diffuse away from the bound non-mammalian enzyme moiety prior to the indoxyl oxidizing, dimerizing and precipitating. A controlled diffusion away from the bound enzyme would have the ad vantage of distributing the radioactive toxic second precipitate more evenly throughout the tumor tissue, thus increasing the size of the Hot-Spots and reducing the problem of tumor heterogeneity. On the other hand, if the diffusion away from the bound enzyme was extreme, it could allow the soluble indoxyl molecules to diffuse into the blood or lymphatic capillaries where it could dimerize, precipitate, and deliver radioactive precipitates to normal tissue and reduce the radiation dose to the tumor. In order to obtain the advantage of controlled diffusion, and to circumvent the problem of the indoxyl diffusing into the blood, various modifications can be made to the indoxyl -lactam that the rate of diffusion of indoxyl into blood capillaries is greatly reduced. Since charged molecules move much slower through the extra-cellular fluid than neutral molecules (Clauss and Jain, 1990, Cancer Research, 50, 3487–3493) (positively charged molecules tend to interact with negatively charged extra-cellular structures, and negatively charged materials are effectively repelled by the many negatively charged extra-cellular structures), molecules having a charge can be covalently attached to the indoxyl-lactam to reduce the rate of diffusion of the soluble indoxyls and intermediates. This can be achieved by attaching a charged molecule to the benzene ring of the indoxyl by reductive amination, involving an amino group on the benzene ring and the reducing end (aldehyde) of the charged molecule. The result is an alkyl amino group, similar to that formed when polylysine is lactosylated by reductive amination. The resultant bond is incapable of being cleaved by mammalian enzymes, and the charged molecule will control the rate of movement of the released indoxyl to be optimum. The attachment of the charged molecule to the benzene ring of the indoxyl-lactam will not interfere with the ability of the beta-lactamase enzyme to cleave the indoxyl-lactam bond, or the ability of the indoxyl to be oxidized and to dimerize and precipitate.

A further modification can be made by covalently attaching two indoxyl -lactam molecules together at a position on the benzene ring to make a bi-indoxyl-lactam. Cleavage of the two lactam bonds of the bi-indoxyl-lactams by beta lactamase creates a bi-indoxyl molecule which will dimerize with two other bi-indoxyl molecules, and so on, to create a self-assembling linear insoluble polymer. The attachment of the two indoxyl-lactams can be either direct, or indirect via a digestible or non-digestible spacer molecule. The spacer molecule can be one of several kinds such as a poly (ethylene oxide) polymer with hetero-bifunctional reactive groups at its terminals (Yokoyama et al, 1992, Bioconjug. Chem. 3, 275–276), a non-degradable copolymer [N-(2-hydroxypropyl) methacrylamide] which is non-immunogenic, non-toxic, and has a versatile chemistry which allows for a range of side chains and pendant chemicals such as lactose, mannose, and radio-labeled tyrosinamide to be introduced (Maeda et al, 1992, Bioconug, Chem. 3, 351–362; Seymour, 1992, Critical Reviews in Therapeutic Drug Carrier Systems, 9, 135–187; Primm et al, 1993, J. Drug Target. 1, 125–131), or a hydrophobic hexamethylene spacer group (Ouchi et al, 1992, Drug Des. Discov. 9, 93–105). The formation of an insoluble linear polymer has substantial advantages in reducing the ability of the substance to move by diffusion and convection in the extra-cellular fluid of the tumor tissue. Additional indoxyls can be made (a) by attaching chemicals to position 3 and which will precipitate by the action of the non-mammalian enzyme moiety of the bispecific reagent, (b) all substituents at position 4, 5, 6, and 7, including hydroxyl groups; (c) phenyl at position 5, and all its derivatives, (d) benzloxy at position 5 and all its derivatives and (e) 5,5- bi-indoxyls, with or without spacers.

Figure 37:
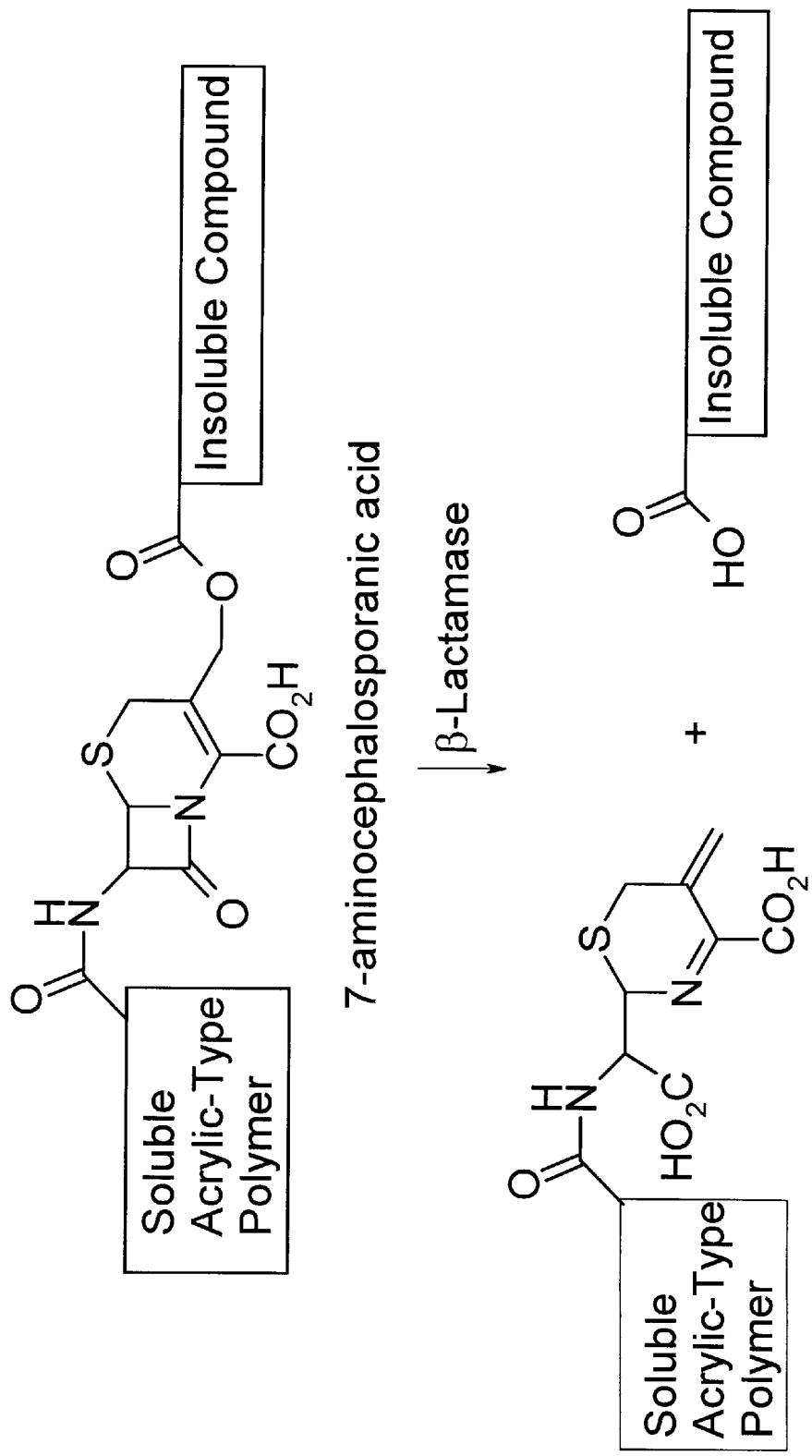
FIG. 37 shows the precipitation of a soluble precipitable material where the soluble moiety is cleaved from the insoluble moiety by beta lactamase causing the insoluble moiety to precipitate spontaneously.

An additional method of converting a soluble second therapeutic agent into an insoluble material which precipitates in the extra-cellular fluid is where the second therapeutic reagent has a soluble moiety and an insoluble moiety, the soluble moiety having a solubilizing effect on the insoluble moiety and being cleaved by the non-mammalian enzyme of the bound bispecific reagent, the solubilizing effect of the soluble moiety being thereby dissipated and the remaining material, being insoluble, spontaneously forming a precipitate. FIG. 37 shows an specific example of this method of precipitation in which beta lactamse cleaves the bond between the soluble and insoluble moiety causing the insoluble moiety to spontaneously precipitate.

As shown in FIG. 38, according to the second method of retaining the new form of the additional therapeutic agent in the tumor region, the soluble radioactive toxic additional therapeutic agent, being the third therapeutic agent 750 is converted by the non-mammalian enzyme moiety 605 of the bispecific reagent 600 into a new form 751 which is soluble and has a neo-antigenic epitope 752, the neo-antigenic epitope 752 not being present on the third therapeutic agent 750. The neoantigenic epitope 752 of the new form of the third therapeutic agent 751 being used, as described later, to "tether" the new form of the third therapeutic agent 751 via a previously administered bispecific reagents which are bound to stable structures in the tumor tissue. The tethering retains the new form of the radioactive toxic third therapeutic agent adjacent to the first extra-cellular precipitate for an extended period of time, the new form of the radioactive toxic third therapeutic agent thereby generating intense fields of radiation, called Hot-Spots, which kill non-selectively all cells adjacent to the first extra-cellular precipitate.

Figure 39:
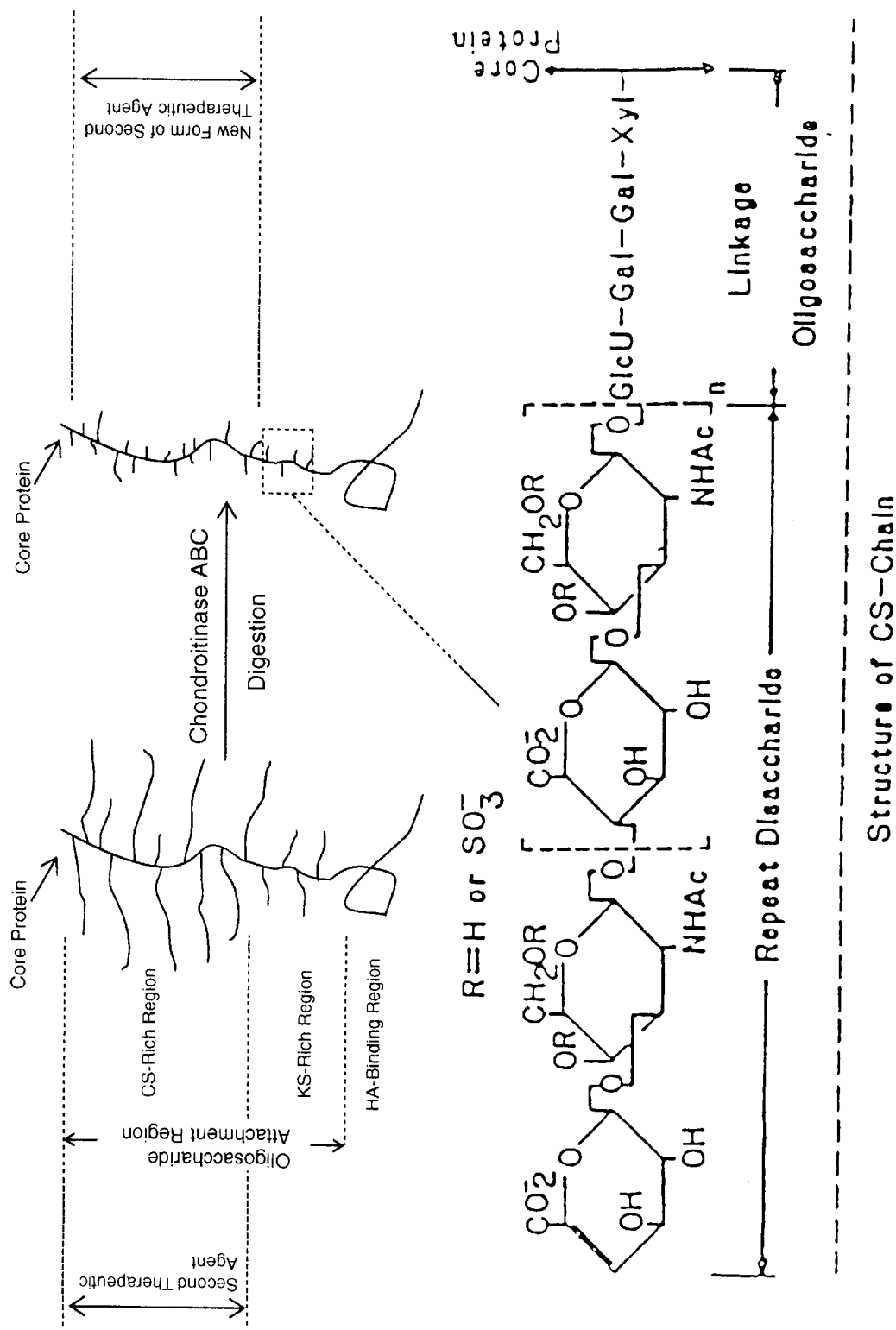
FIG. 39 shows the third therapeutic agent being chondroitin sulphate being converted by chondroitinase into a new form.

A specific example of a non-mammalian enzyme-substrate system to be used for this method is chondroitinase ABC as the non-mammalian enzyme, and radio-labeled chondroitin sulphate attached to a short polypeptide as the third therapeutic agent, as shown in FIG. 39. Chondroitin sulphate is degraded by the chondroitinase ABC enzyme which cleaves the repeat disaccharide portion of the chondroitin sulphate chain and to leave only the linkage oligosaccharide with its terminal glucuronic acid residue attached to the protein core. The chondroitin sulphate is thereby converted by the chondroitinase ABC enzyme into a new form which is soluble and has a neo-antigenic epitope not found on the untreated chondroitin sulphate (Haskall et al, 1972, J. Biol. Chem., 247, 4521–4528; Distler and Jourdian 1973, J. Biol. Chem., 248, 6772–6780). The new form of the third therapeutic agent is soluble and is tethered via its neo-antigenic epitope by the previously administered bispecific reagents bound to stable structures in the tumor tissue for an extended period of time to generate intense fields of radiation, called Hot-Spots, which kill non-selectively all cells adjacent to the first extra-cellular precipitate. The tethering of the new form of the second therapeutic agent is described later.

Figure 40:
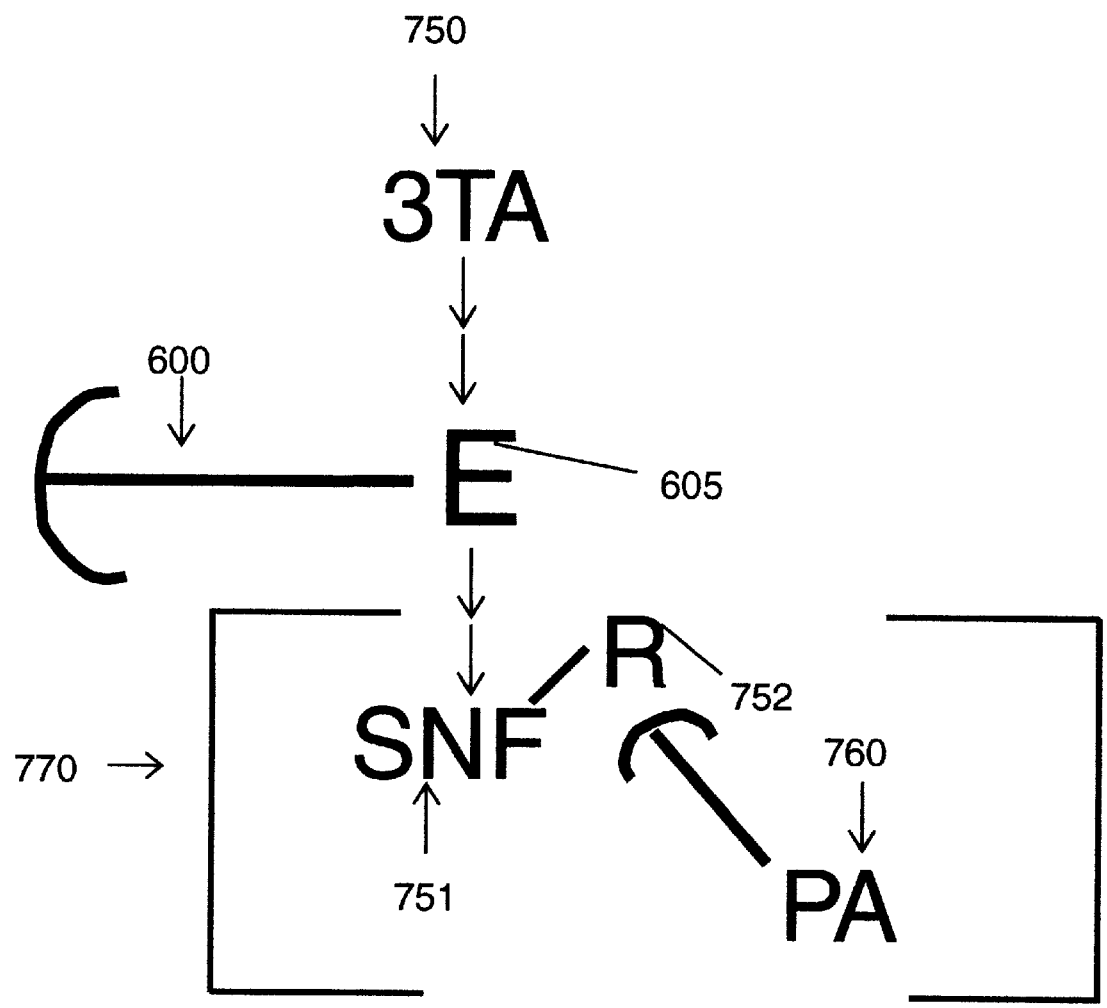
FIG. 40 shows the conversion of the third therapeutic agent into a new form, which is soluble, which is then acted on by a precipitating antibody to form the third extra-cellular precipitate.

As illustrated in FIG. 40, according to the third method of retaining the new form of the additional therapeutic agent in the tumor region, the soluble radioactive toxic additional therapeutic agent, being the third therapeutic agent 750 is converted by the non-mammalian enzyme moiety 605 of the bispecific reagent 600 into a new form 751 which is soluble and has a neo-antigenic epitope 752, the neo-antigenic epitope 752 not being present on the third therapeutic agent 750. Prior to administering the third therapeutic agent 750, a precipitating antibody 760 which has the ability to react with the neo-antigenic epitope 752 of the new form of the third therapeutic agent 751 is administered to the living host. The administered precipitating antibody 760 has the ability to bind to the neo-antigenic epitope 752 of the new form of the third therapeutic agent 751, the binding causing a precipitate to form, the precipitate being the third extra-cellular precipitate 770 which is composed of the administered precipitating antibody 760 complexed to the new form of the third therapeutic agent 751.

The administration of large molecules results in higher concentrations of large molecules to be present in tumor tissue compared to normal tissue (Seymour, 1992, Critical Reviews in Therapeutic Drug Carrier Systems, 91, 135–187). Therefore, the concentration of the administered precipitating antibody, being a large molecule, will be higher in the tumor than in normal tissues. The higher concentration of the precipitating antibody in tumor tissues enables a larger amount of the new form of the third therapeutic agent to bind and complex to the precipitating antibody and thereby form a precipitate which is the third extra-cellular precipitate which is retained in the tumor tissue for an extended time.

A specific example of a non-mammalian enzyme-substrate system to be used in the third method is chondroitinase ABC as the non-mammalian enzyme, and radio-labeled chondroitin sulphate (CS) as the third therapeutic agent. As described in method two, the chondroitinase ABC converts the chondroitin sulphate into a new form, the new form being a soluble material and having a neo-antigenic epitope not found on the chondroitin sulphate (Christner et al, 1980, J. Biol. Chem., 255, 7102–7105). Prior to the administration of the chondroitin sulphate, a precipitating antibody capable of binding to the neo-antigenic epitope of the chondroitin sulphate is administered to the living host. The complex, formed by the administered precipitating antibody binding to the neo-antigenic epitope of the chondroitin sulphate forms a precipitate, the precipitate being the third extra-cellular precipitate remains in the tumor region adjacent to the first extra-cellular precipitate for an extended period of time to kill non-selectively all cells adjacent to the first extra-cellular precipitate.

The intensity of the radiation field that will be generated by each of the three methods that use the non-mammalian enzyme moiety to convert the additional therapeutic agent into a new form capable of generating Hot-Spots is very high. A large number of non-mammalian enzyme moiety molecules, for example beta-lactamase or chondroitinase ABC, will be bound to the first extra-cellular precipitate (the number of enzyme molecules being proportional to the amount of precipitate which had accumulated inside the targeted cells via the administration of the binary reagent; and since is possible to accumulate any required amount of intra-cellular precipitate, the number of bound non-mammalian enzymes can be made large). Calculations show that the number of non-mammalian enzyme moiety molecules which can be deposited can be a thousand times higher than the amount of enzyme accumulated by the conventional ADEpT approach. The more non-mammalian enzyme moieties that are bound, the higher will be the rate at which the additional therapeutic agent is converted into the new form. The higher the rate of conversion, the more intense will be the radiation field adjacent to the non-mammalian enzyme moiety and the lower the level of systemic toxicity in the living host will be.

Inherent in the problem of constructing a successful treatment of cancer is the fact that there is no exploitable characteristic which is unique to cancer tissue in different patients or even in different locations of the one cancer in any one patient Every characteristic of cancer tissue is also shared to some degree with some normal tissue. This includes characteristics of the cancer cells, characteristics of normal cells within the cancer, and characteristics of extra-cellular structures in the cancer. Since no single unique difference exists between cancer and normal tissue, the only way to improve the tumor specificity of Hot-Spot location, is for the location of Hot-Spots to be determined by multiple differences. Even though each difference is imperfect by itself to make the Hot-Spot location entirely specific to the cancer, acting together these differences provide a high degree of specificity.

In the present invention, two primary characteristics determine the location of the Hot-Spots, and both must be present on a single cell, in an all-or-nothing fashion for Hot-Spots to develop around the cell. The two characteristics being that: (1) the cell must have the first antigenic receptor for the first targeting agent of the binary reagent so that the first target cancer cells will accumulate a precipitate by receptor mediated endocytosis; and (2) the cell must have a high sensitivity to being killed by the natural system of the living host and a high sensitivity to being killed by the first therapeutic agent so that the intra-cellular precipitate will be relocated to the extra-cellular fluid of the tumor and to become the first extra-cellular precipitate. Given the present imperfect status of targeting agents, it is likely that the selective killing of the supersensitive fraction of the cancer cells will be the most effective feature which can direct the location of the Hot-Spots specifically to the tumor.

Figure 41:
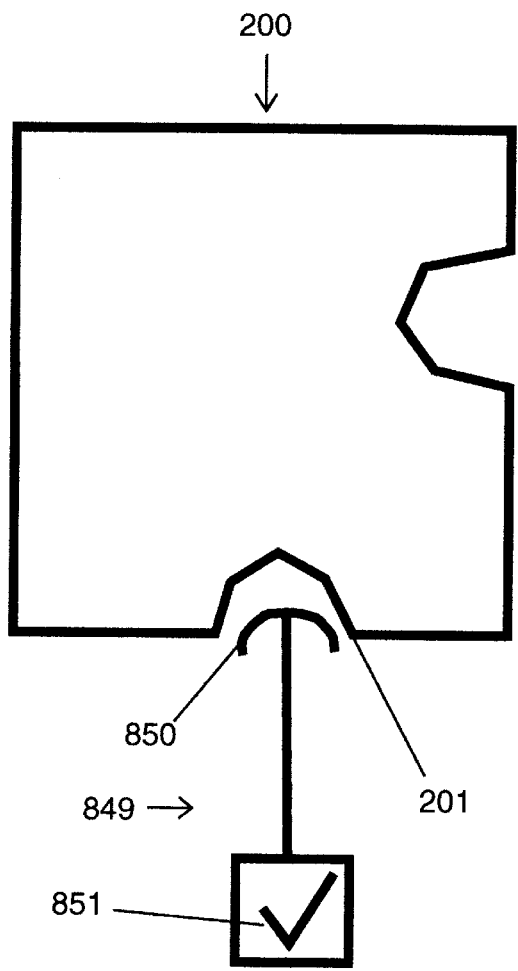
FIG. 41 shows the second binary reagent binding to the first target normal cells to inhibit precipitate from forming in first target normal cells.

Inhibiting the accumulation of the precipitate in normal cells improves tumor specificity, because precipitate accumulation is mandatory for Hot-Spots to be generated. As shown in FIG. 41, inhibition of precipitation in target normal cells can be achieved by administering to the living host a second binary reagent 849 prior to, and during the time of, the administration of the first binary reagent 149. The second binary reagent 849 being composed of the third targeting agent 850 which has a substantially specific affinity for the third antigenic receptor 201 of the target normal cells 200 and which is capable of endocytosis. The second binary reagent 849 further including a material 851 attached to the third targeting agent 850, the material, when detached, adapted to inhibit receptor mediated endocytosis and precipitation from occurring in the first target normal cells 200.

Inhibiting precipitation in cells can be achieved by a great variety of chemicals acting in different ways, and in different steps of the receptor mediated endocytic and lysosomal process. The following materials, each of which can be attached to a targeting agent and detached in lysosomes, have been shown to inhibit receptor mediated endocytosis: vinblastine, monensin and chloroquine (Gueant J. L. et al, 1992 FEBS. Lett. 297, 229–232), staurosporine, a protein kinase inhibitor, (Fallon R. J and Danaher M, 1992, Exp. Cell Res. 203, 420–426), primary amines, such as putrescine or dansylcadaverine, which can be used for sustained periods under physiological conditions without causing toxicity, and by increasing the osmotic tonicity of the lysosome vacuoles (Bradley J. R. et al, 1993, J. Immunology 150, 5544–5555) which can be achieved by methyl esters of amino acids (Goldman R and Kaplan A, 1973, Biochim. Biophys. Acta 318, 205–216), glycyl-L- phenylalanine 2-naphthylamide (Berg T. O. et al, 1994, 300,229–236) as well as certain tripeptides (Jadot M. et al, 1984, Biochem. J. 219, 965–970) which are hydrolyzed to free amino acids that do not readily diffuse back out of the lysosomes due to their polarity, which results in increasing the osmotic tonicity of the lysosomes. In addition, precipitation can also be inhibited by materials which can inhibit the enzyme(s) necessary for detaching the precipitable material from its attachment to the targeting agent or inhibiting the enzyme responsible for converting the detached precipitable material into a precipitate. For example, the bacterial peptide leupeptin inhibits proteolytic enzymes (Dunn W. et al, 1979, J. Biol. Chem. 254,4191–4196) and retards the lysosomal transport and digestion of ligands (Tolleshaug H and Berg T, 1981, Expt. Cell Research, 134, 207–217) which will inhibit precipitate from forming. Other agents can inhibit specific lysosome enzymes which are necessary for converting the detached soluble precipitable material into a precipitate. For example, the pseudote aharide acarbose is a potent inhibitor of alpha-glucosidase (Salehi A. et al, 1995, Diabetes, 44, 830–836) and 1-deoxymannojirimycin, is a mannosidase inhibitor and N-methyl-1-deoxynorjirimycin is a glucosidase inhibitor (Faber E. D. etal, 1994, Pharm. Res., 11, 144–150).

Although the formation of precipitates by the administration of the binary reagent is confined mainly inside targeted cells, some precipitation can also take place in the extra-cellular fluid which would have the effect of decreasing the tumor specificity of relocated first extra-cellular precipitate. The antigenic epitopes of precipitate formed in the extra-cellular fluid can be cleaved by the administration of a free non-mammalian enzyme while the accumulated intra-cellular precipitate is retained in its intra-cellular location, the intra-cellular location protecting the intra-cellular precipitate from the action of the free non-mammalian enzyme. For example, administering beta lactamase could cleave the penicillin which was attached to the soluble precipitable material and which became the second antigenic epitope of the first extra-cellular precipitate, administering cellulase would digest a cellulose precipitate, and administering chitinase would digest a chitin precipitate in analogous fashion to the in vivo digestion of a fibrin blood clot by the administration of tissue plasminogen activating factor or streptokinase.

After the free non-mammalian enzyme action on the unwanted extracellular precipitate has been completed, the free non-mammalian enzyme must be eliminated from the living host so that the enzyme will not be able to act on the first extra-cellular precipitate. The administered free non-mammalian enzyme can be eliminated naturally with time and the elimination can be hastened by the administration of a galactosylated antibody specific to the enzyme which will complex and inhibit the enzyme, and/or cause the antibody-enzyme complex to be quickly taken up by the liver in a similar manner as is used in ADEPT. Alternatively the free non-mammalian enzyme can be inhibited by the administration of a specific inhibitor. Reversible and irreversible inhibitors for enzymes are well known and many are used in clinical medicine. In particular, a large number of inhibitors of penicillinase and beta lactamase are known, for example clavulanic acid is a mechanism based irreversible inhibitor of beta-lactamase (Barrett, A. J., and Salvesen, G., (eds), 1986,. "Proteinase Inhibitors," Elsevier, Amsterdam; Sandler, M., (ed.), 1980, "Enzyme Inhibitors as Drugs," Macmillan, London; Sandler, M., and Smith, H. J., (eds.), 1989, "Design of Enzyme Inhibitors as Drugs," Oxford University Press, Oxford; Smith, H. J. (ed.), 1988, "Introduction to the Principles of Drug Design." 2nd ed., Wright, London).

After the steps of administering the binary reagent, permitting the binary reagent to be endocytosed, continuing the introducing of the binary reagent, and after all the binary reagent in extra-cellular fluids has been eliminated by natural elimination systems, a scan of the entire tumor bearing subject can be carried out (the precipitable material having been previously trace labeled) using an apparatus which can detect radioactivity, and optionally confirmed by biopsy, to determine if cells in non-tumor locations have accumulated precipitate. If the scan and/or biopsy shows that a significant number of normal bone marrow cells have accumulated precipitate, the bone marrow from a number of locations can be removed and examined (for example by a cell sorter) and the normal bone marrow cells that had accumulated precipitate could be eliminated, and the remaining bone marrow now free of cells containing precipitate would be returned to the living host and the therapy continued.

Normal cells die or are killed as part of the natural cell turnover by a process called apoptosis, the death of the cells being followed by the encapsulation of the intra-cellular contents of the dead cells into non-permeable vesicles. These vesicles are very quickly phagocytosed by neighboring parenchymal or professional phagocytes (Kerr et al, 1972, Br J Cancer, 26, 239–257; Arends et al, 1991, Int. J. Expt. Path., 32, 223–254; Patel and Gores, 1995, Hepatology, 21 ,1725–1741), thus preventing their intra-cellular contents, including the intra-cellular precipitate which the cells had accumulated, from being discharged into the extra-cellular fluid. When cells are killed by lysis (in contrast to apoptosis) their membranes abruptly lose their integrity and become permeable and the natural intra-cellular contents of the cells, including the precipitate, is discharged into the extra-cellular fluid. Since Hot-Spots can only be generated around precipitates in the extra-cellular fluid, it follows that Hot-Spots can be generated around cells killed by lysis but are unlikely to be generated around cells that have been killed by apoptosis.

Lytic killing of cancer cells has been achieved by uni-specific antibody (Ball Ed, 1995, European J. of Morphol. 33, 95–100; Phan et al. 1995, Gastroenterology, 108, 495–504; Morgan et al. 1995, Immunology, 86,319–324; Ballare et al. 1995, Cancer Immunol. Immunother. 41, 15–22), bispecific antibody (Karpovsky et al. 1984, J. Experimental Medicine 160, 1686–1701; Wong and Colvin 1987, J. Immunology 139, 1369–1374) and cellular lysis (Sutton et al. 1994, Therapeutic Immunology, 1, 83–93; Kinouchi et al., 1995, J. Urology, 154, 288–292; Parker et al., 1995, J. Infectious Diseases, 171, 186–189). Complement induced lysis is controlled by a number of regulatory factors which can be manipulated to enhance or depress lysis (Bjorge and Matre, 1995, Scand. J. Immunology, 42, 512–516; Brasoveanu et al., 1995, International J. Cancer, 61, 548–556; Azuma et al., 1995, Scand. 'J. Immunology, 42, 202–208).

Figure 42:
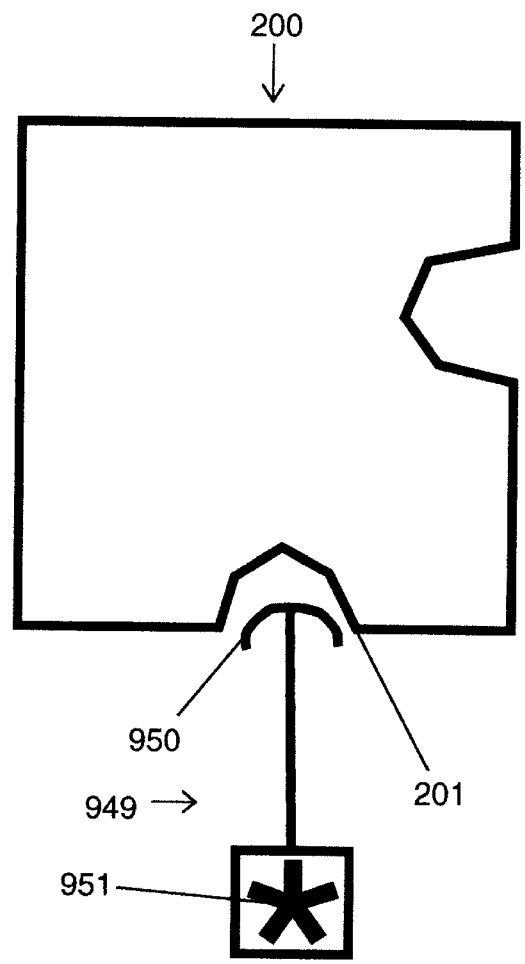
FIG. 42 shows the third binary reagent binding to the first target normal cells to protect first target normal cells from being killed by the first therapeutic agent.

In addition, specificity can be enhanced, as shown in FIG. 42, by administering to the living host a third binary reagent 949 prior to, and during the time of, the administration of the first therapeutic reagent. The third binary reagent 949 including the third targeting agent 950 having a substantially specific affinity for the second antigenic receptor 201 of the first target normal cells 200, the second antigenic receptor 201 being capable of endocytosis. The third binary reagent 949 further including a material attached to the third targeting agent, the material 951, when detached, adapted to protect the first target normal cells from otherwise being killed by the first therapeutic agent. For example, protection of targeted cells from the otherwise cytotoxic effect of methotrexate by an administered binary reagent, comprised of a targeting agent and folinic acid, which is an antidote to the methotrexate has been reported (Wu et al, 1983, Proc. Natl. Acad. Sci. USA, 80,3078–3080). Protection of normal cells from being killed by the first therapeutic agent will increase tumor specificity of Hot-Spot location.

Increasing the tumor specificity beyond that obtained by these two primary characteristics can be achieved during each step of the Hot-Spot generating process by additional reagents and by naturally occurring mechanisms at the cellular and tissue level which operate to retain the first, second, and third extra-cellular precipitates and the soluble new form of the third therapeutic agent in cancer tissue, but not in normal tissue.

Following the administration of the first therapeutic agent, and prior to the delivery of the bispecific reagent and/or the additional administration of the second therapeutic agent, several mechanisms operate to transfer relocated first extra-cellular precipitate in normal tissue (but not cancer tissue) to a location where first extra-cellular precipitate cannot act as a platform from which a Hot-Spot can be generated. Macrophages in the normal tissue can transfer the first extra-cellular precipitate to an intra-cellular location by phagocytosis, thereby preventing Hot-Spots from developing. In contrast, macrophages in cancer tissue are inhibited by the cancer cell driven aberrant environment (Boetcher and Leonard, 1974, J. Nat. Cancer Inst. 52, 1091–1096; Snyderman et al, 1978, J. Nat. Cancer Inst. 60, 737–742; Norman, 1985, in Macrophage Biology, p.285–298, Allan R Liss Inc.; Braun et al, 1993, Cancer Research, 53, 3362–3368) and will not phagocytose the first extra-cellular precipitate as effectively.

In addition, normal epithelial cells that line the boundary between the inner and outer environment of the body exfoliate into the lumen of the organ when they are killed (Ishikawa et al, 1993, 17 suppl. pS 104–110; Montefort et al, 1993, Eur. Respir. J. , 6, 1257–1263; Sisson et al, 1994, Am. J. Respir. Crit. Care Med. 149, 205–213). The exfoliation of these cells effectively transfers their intra-cellular contents, including accumulated precipitate, to a location where the precipitate cannot act as a platform on which Hot-Spots could later be generated. In contrast, cancer cells which arise from these boundary cells only grow inside the body of the host and cannot exfoliate to the external environment Consequently, virtually all cancer epithelial cells (but not normal epithelial cells) that have both accumulated precipitate and which have been killed will be in a correct location to generate Hot-Spots.

Similarly, normal endothelial cells that are damaged or killed become detached and enter the blood stream (Dini et al, 1995, J. Cell. Sci. 108, 967–73) and their intra-cellular contents including accumulated precipitate will be quickly engulfed by the macrophages which line the sinusoids of the liver and spleen, thereby making the precipitate unavailable to generate Hot-Spots.

Particles which are injected into the extra-cellular fluid move by convective flow from the extra-cellular fluid of tissues into the lymph drainage channels which drain into to the regional lymph nodes, where the particles are quickly and effectively engulfed by the very active macrophages which line the lymph flow pathway. Relocated first extra-cellular precipitates and second and third extra-cellular precipitates behave in a similar way and suffer the same fate. The movement of precipitate can occur in normal tissue thereby reducing the number of Hot-Spots which would otherwise have been generated in normal tissue. The movement of the first extra-cellular precipitates in normal tissue which enables the precipitate to be engulfed by macrophages in the regional lymph glands prevents Hot-Spots from developing in normal tissues, whereas movement of radioactive second and third precipitates in normal tissues which enables the radioactive precipitates to be engulfed by macrophages in the regional lymph glands causes Hot-Spots to be generated in the regional lymph glands, which is a much more desirable and clinically safe location for radiation damage to occur, compared to normal parenchymal tissue. In contrast, cancer tissue lacks an effective lymphatic drainage system (Jain, 1987, Cancer Research, 47, 3039–3051; Jain and Baxter, 1988, Cancer Research, 48, 7022–7032; Clauss and Jain, 1990,50,3487–3492) and first, second, and third extra-cellular precipitate movement into the lymphatic system cannot take place from tumor tissue and there will be no reduction in the number of Hot-Spots which will be generated in tumor tissue.

Lymphatic vessels are sometimes present in tumor tissue (reflecting the heterogeneity of non-malignant cells within the tumor tissue) which could lead to movements of the first, second and third extra-mllular precipitate into regional lymph glands. This movement can be prevented by "tethering" the first and second extra-cellular precipitate and the soluble new form of the second therapeutic agent to stable structures which are substantially more present in tumor tissue. Tethering of the first extra-cellular precipitate can be achieved by administering bispecific reagents to the living host prior to the administration of the first therapeutic agent to tether the extra-cellular precipitate to at least one of three different stable structures in the extra-cellular fluid including the third antigenic receptor of the second target cancer cells, the antigenic epitopes of the cancer-altered extra-cellular matrix, and the antigenic epitopes of the relocated natural intra-cellular material. The bispecific reagents being comprised of two moieties, the first moiety having an affinity for one of the first antigenic epitope, second antigenic epitope, and neo-antigenic third epitope of the extra-cellular precipitate. The second moiety having an affinity for at least one of three different stable structures in the extra-cellular fluid including the third antigenic receptor of the second target cancer cells, the antigenic epitopes of the cancer-altered extra-cellular matrix, and the antigenic epitopes of the relocated natural intra-cellular material.

Figure 43:
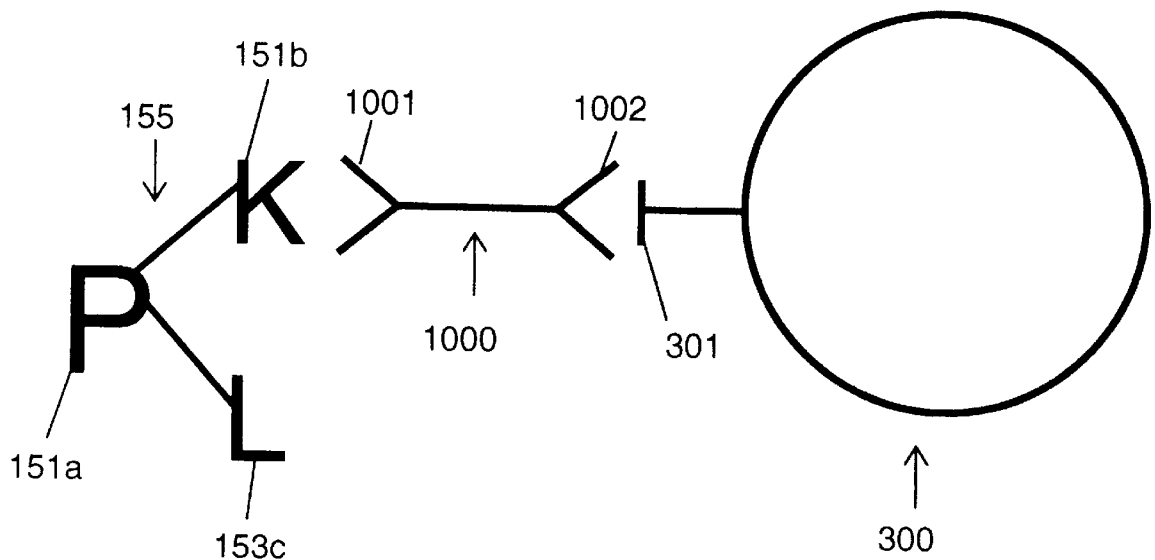
FIG. 43 shows the second bispecific reagent tethering the first extra-cellular precipitate to the second target cancer cells.

FIG. 43 shows the second bispecific reagent 1000 tethering the first extra-cellular precipitate 155 to the third antigenic receptor 301 of the second target cancer cells 300. The second bispecific reagent 1000 being comprised of two moieties, the first moiety 1001 being a targeting agent with an affinity for the second antigenic epitope 151b of the first extra-cellular precipitate 155. The second moiety 1002 of the second bispecific reagent being capable of binding to the third antigenic receptor 301 of the second target cancer cells 300. The second bispecific reagent thereby tethering the first extra-cellular precipitate 155 and retaining it in the extra-cellular fluid of the cancer. Alternatively the first moiety of the second bispecific reagent 1001 could have an affinity for the first antigenic epitope 151a of the first extra-cellular precipitate 155 or could have an affinity for the neo-antigenic third epitope 153c of the first extra-cellular precipitate 155.

Figure 44:
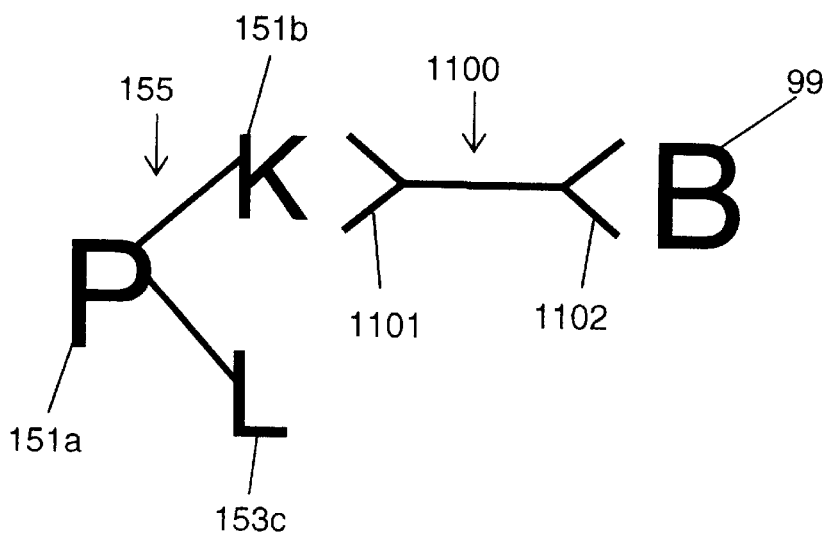
FIG. 44 shows the third bispecific reagent tethering the first extra-cellular precipitate to the cancer-altered extra-cellular matrix.

FIG. 44 shows the third bispecific reagent 1100 tethering the first extra-cellular precipitate 155 to the antigenic epitopes of the cancer-altered extra-cellular matrix 99. The third bispecific reagent 1100 being comprised of two moieties, the first moiety 1101 being a targeting agent with an affinity for the second antigenic epitope 151b of the first extra-cellular precipitate 155. The second moiety 1102 of the third bispecific reagent being capable of binding to the antigenic epitopes of the cancer-altered extra-mllular matrix 99. The third bispecific reagent thereby tethering the first extra-cellular precipitate 155 and retaining it in the extra-cellular fluid of the cancer. Alternatively the first moiety 1101 of the third bispecific reagent could have an affinity for the first antigenic epitope 151a of the first extra-cellular precipitate 155 or could have an affinity for the neo-antigenic third epitope 153c of the first extra-cellular precipitate 155.

Figure 45:
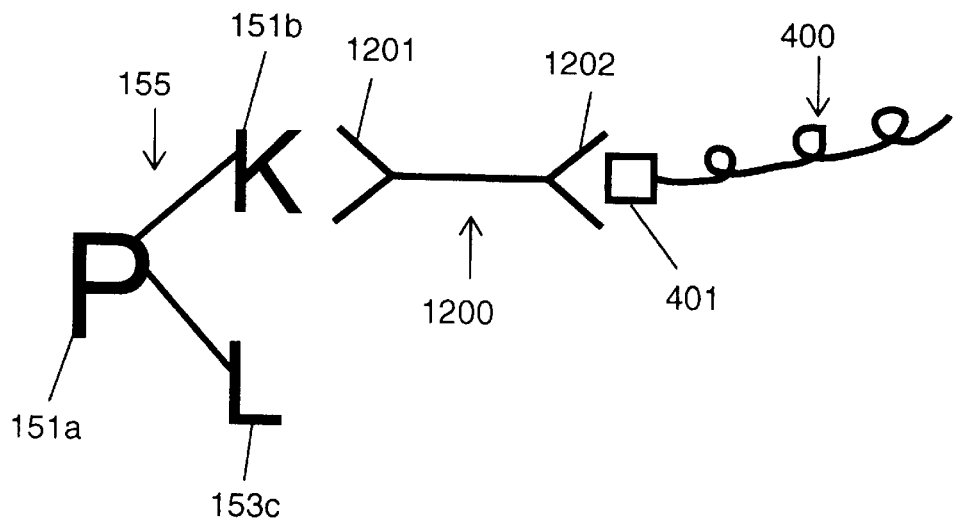
FIG. 45 shows the fourth bispecific reagent tethering the first extra-cellular precipitate to the relocated natural intra-cellular contents of cells.

FIG. 45 shows the fourth bispecific reagent 1200 tethering the first extra-cellular precipitate 155 to the antigenic epitopes of the relocated natural intra-cellular material 401. The fourth bispecific reagent 1200 being comprised of two moieties, the first moiety 1201 being a targeting agent with an affinity for the second antigenic epitope 151b of the first extra-cellular precipitate 155. The second moiety 1202 of the fourth bispecific reagent being capable of binding to the antigenic epitopes of the relocated natural intra-cellular material 401. The fourth bispecific reagent thereby tethering the first extra-cellular precipitate 155 and retaining it in the extra-cellular fluid of the cancer. Alternatively the first moiety 1201 of the fourth bispecific reagent could have an affinity for the first antigenic epitope 151a of the first extra-cellular precipitate 155 or could have an affinity for the neo-antigenic third epitope 153c of the first extra-cellular precipitate 155.

Specificity is also increased because the binding moiety of the bispecific reagent binds to the antigenic epitopes of the first extra-cellular precipitate, and because the first extra-cellular precipitate is a material not naturally present in the body, the binding moiety of the bispecific reagent with its non-mammalian enzyme moiety can have a high and specific affinity for the antigenic epitopes of the first extra-cellular precipitate with little or no cross reaction to natural structures of the living host. For example, the cellulose binding domain peptide, from which the bispecific reagent with its non-mammalian enzyme moiety can be made, binds virtually irreversibly to cellulose, which is one candidate material for the first extra-cellular precipitate.

Increased specificity of "Hot-Spot" location can also be achieved by "tethering" the second extra-cellular precipitate and by tethering the new form of the third therapeutic agent in a manner similar to that employed to tether the first extra-cellular precipitate.

Figure 46:
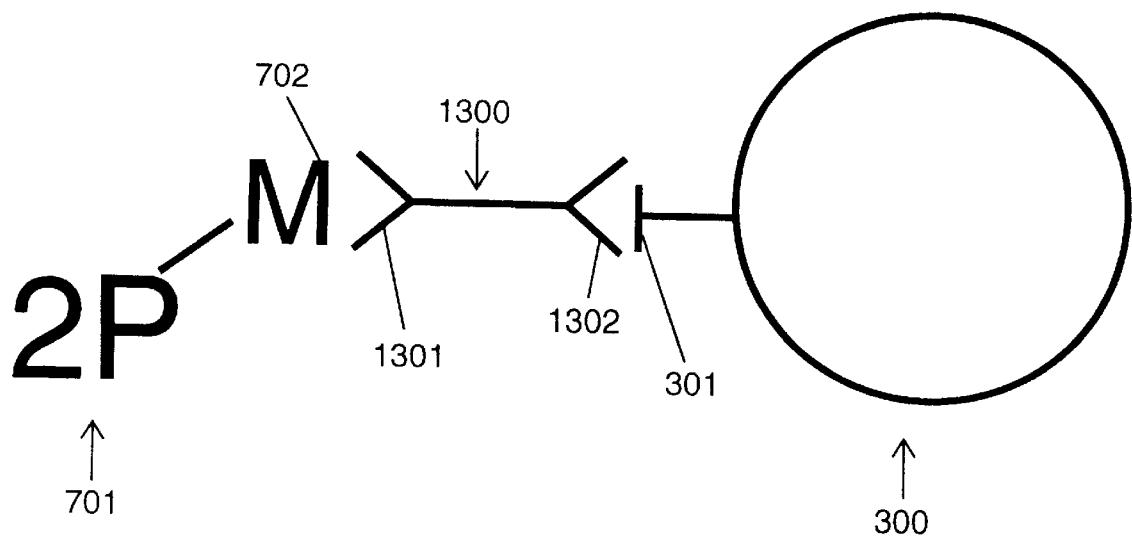
FIG. 46 shows the fifth bispecific reagent tethering the second extra-cellular precipitate to the second target cancer cells.

For example, FIG. 46 shows the shows the fifth bispecific reagent 1300 tethering the second-extra-cellular precipitate 701 to the third antigenic receptor 301 of the second target cancer cells 300. The fifth bispecific reagent 1300 being comprised of two moieties, the first moiety 1301 being a targeting agent with an affinity for the additional antigenic epitope 702 of the second extra-cellular precipitate 701. The second moiety 1302 of the fifth bispecific reagent 1300 being capable of binding to the third antigenic receptor 301 of the second target cancer cells 300. The fifth bispecific reagent thereby tethering the second extra-cellular precipitate 701 and retaining it in the extra-cellular fluid of the cancer.

Figure 47:
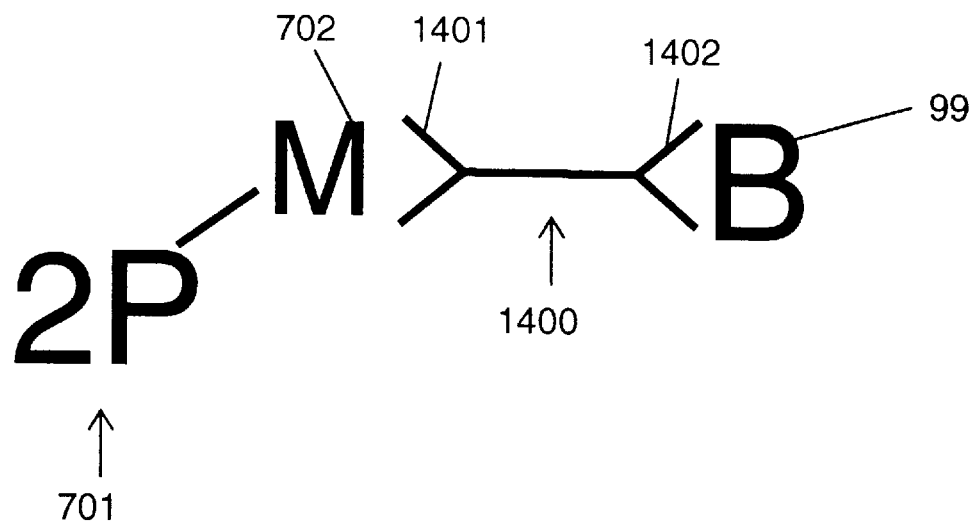
FIG. 47 shows the sixth bispecific reagent tethering the second extra-cellular precipitate to the cancer-altered extra-cellular matrix.

FIG. 47 shows the sixth bispecific reagent 1400 tethering the second extra-cellular precipitate 700 to the antigenic epitopes of the cancer-altered extra-cellular matrix 99. The sixth bispecific reagent 1400 being comprised of two moieties, the first moiety 1401 being a targeting agent with an affinity for the additional antigenic epitope 702 of the second extra-cellular precipitate 701. The second moiety 1402 of the sixth bispecific reagent being capable of binding to the antigenic epitopes of the cancer-altered extra-cellular matrix 99. The sixth bispecific reagent thereby tethering the second extra-cellular precipitate 701 and retaining it in the extra-cellular fluid of the cancer.

Figure 48:
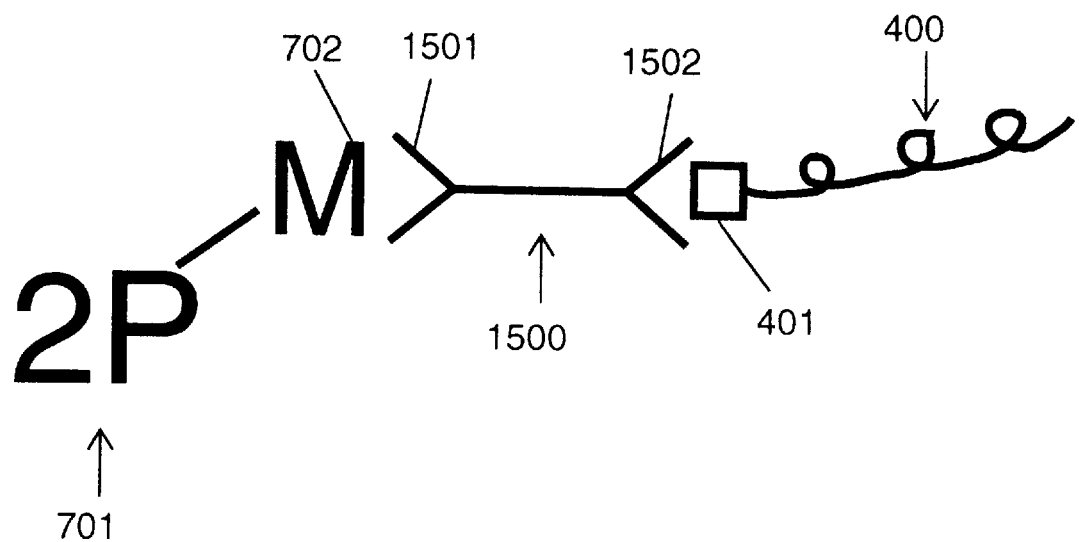
FIG. 48 shows the seventh bispecific reagent tethering the second extra-cellular precipitate to the relocated natural intra-cellular contents of cells.

FIG. 48 shows the seventh bispecific reagent 1500 tethering the second extra-cellular precipitate 701 to the antigenic epitopes of the relocated natural intra-cellular material 401. The seventh bispecific reagent 1500 being comprised of two moieties, the first moiety 1501 being a targeting agent with an affinity for the additional antigenic epitope 702 of the second extra-cellular precipitate 701. The second moiety 1502 of the seventh bispecific reagent being capable of binding to the antigenic epitopes of the relocated natural intra-cellular material 401. The seventh bispecific reagent thereby tethering the second extra-cellular precipitate 701 and retaining it in the extra-cellular fluid of the cancer.

Figure 49:
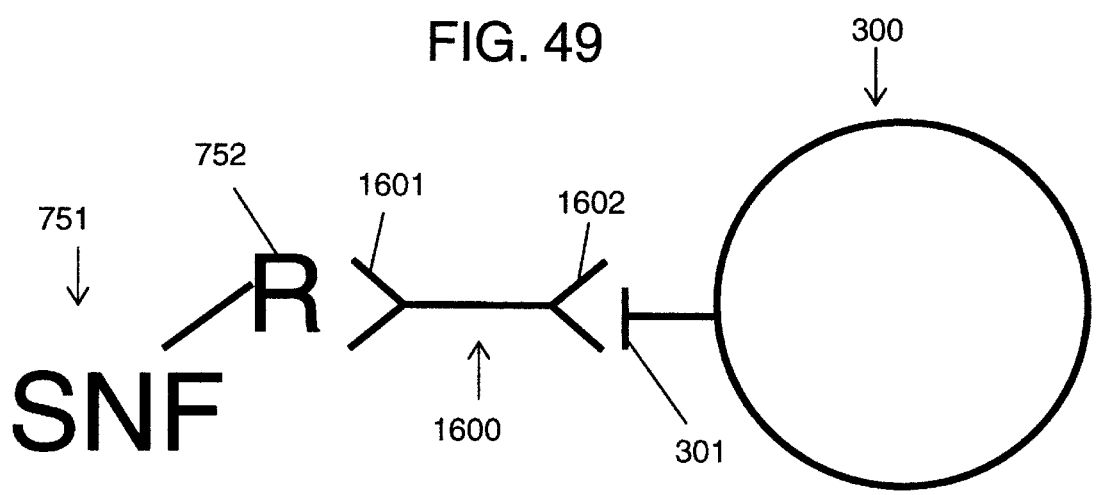
FIG. 49 shows the eighth bispecific reagent tethering the new form of the third therapeutic agent, which is soluble, to the second target cancer cells.

For example, FIG. 49 shows the shows the eighth bispecific reagent 1600 tethering the soluble new form of the third therapeutic agent 751 to the third antigenic receptor 301 of the second target cancer cells 300. The eighth bispecific reagent 1600 being comprised of two moieties, the first moiety 1601 being a targeting agent with an affinity for the additional antigenic epitope 752 of the soluble new form of the third therapeutic agent 751. The second moiety 1602 of the eighth bispecific reagent 1600 being capable of binding to the third antigenic receptor 301 of the second target cancer cells 300. The eighth bispecific reagent thereby tethering the soluble new form of the third therapeutic agent 751 and retaining it in the extra-cellular fluid of the cancer.

Figure 50:
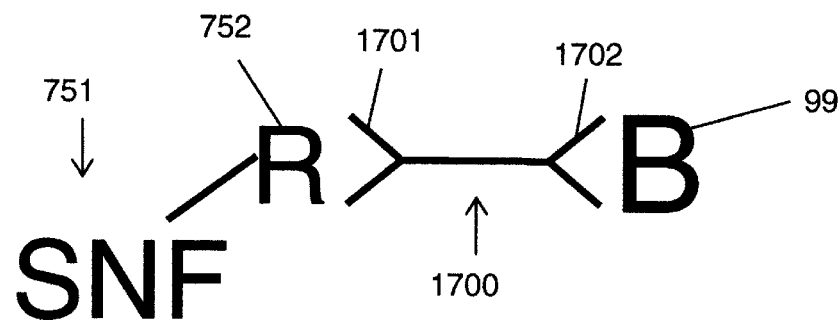
FIG. 50 shows the ninth bispecific reagent tethering the new form of the third therapeutic agent, which is soluble, to the cancer-altered extra-cellular matrix.

FIG. 50 shows the ninth bispecific reagent 1700 tethering the second extra-cellular precipitate 700 to the antigenic epitopes of the cancer-altered extra-cellular matrix 99. The ninth bispecific reagent 1700 being comprised of two moieties, the first moiety 1701 being a targeting agent with an affinity for the additional antigenic epitope 752 of the soluble new form of the third therapeutic agent 751. The second moiety 1752 of the ninth bispecific reagent being capable of binding to the antigenic epitopes of the cancer-altered extra-cellular matrix 99. The ninth bispecific reagent thereby tethering the soluble new form of the third therapeutic agent 751 and retaining it in the extra-cellular fluid of the cancer.

Figure 51:
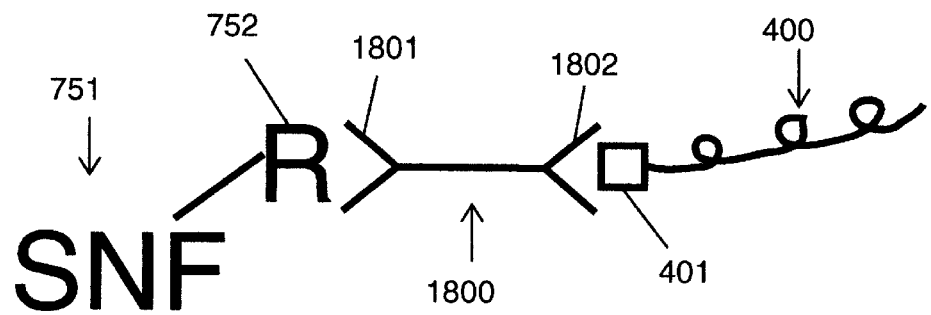
FIG. 51 shows the tenth bispecific reagent tethering the new form of the third therapeutic agent, which is soluble, to the relocated natural intra-cellular contents of cells.

FIG. 51 shows the tenth bispecific reagent 1800 tethering the soluble new form of the third therapeutic agent 751 to the antigenic epitopes of the relocated natural intra-cellular material 401. The tenth bispecific reagent 1800 being comprised of two moieties, the first moiety 1801 being a targeting agent with an affinity for the additional antigenic epitope 752 of the soluble new form of the third therapeutic agent 751. The second moiety 1802 of the tenth bispecific reagent being capable of binding to the antigenic epitopes of the relocated natural intra-cellular material 401. The tenth bispecific reagent thereby tethering the soluble new form of the third therapeutic agent 751 and retaining it in the extra-cellular fluid of the cancer.

What is claimed is:

1. A method for treating a heterogeneous population of cancer cells in a living host by at least a first therapeutic agent and an additional therapeutic agent, the living host being a natural system composed of extra-cellular fluid and normal cells and cancer cells growing in the extra-cellular fluid, the normal cells containing soluble and cellular components which can attack and kill cancer cells, the normal cells growing in a normal extra-cellular matrix, the normal extra-cellular matrix having at least collagen and fibronectin, the heterogenous population of cancer cells growing in a cancer-altered extra-cellular matrix having at least cancer-altered antigenic epitopes, the heterogeneous population of cancer cells endogenously making and containing products selected from the group consisting of sulphated glycosaminoglycans, natural intra-cellular enzymes in the natural enzyme-rich vacuoles contained in the cell which are lysosomes, and natural intra-cellular material selected from the group consisting of DNA, histone and complexes of DNA-histone, the DNA, histone and complexes of DNA-histone having antigenic epitopes, the heterogeneous population of cancer cells selected from the group consisting of least three sub-populations of cancer cells:

a first sub-population of cancer cells being first target cancer cells each having a first antigenic receptor which is substantially specific to a cancer cell and which binds a first targeting agent, the first antigenic receptor inducing endocytosis when the first targeting agent binds to the first antigenic receptor;

the first target cancer cells having a sensitivity to being killed by the natural system of the living host and a sensitivity to being killed by the first therapeutic agent; and a second sub-population of cancer cells being second target cancer cells each having a third antigenic receptor which is substantially specific to a cancer cell and which binds a third targeting agent, the third antigenic receptor being incapable of endocytosis; and a third sub-population of cancer cells being non-target cancer cells which are the remainder of the cancer cells;

the normal cells of the living host endogenously making and containing products selected from the group consisting of sulphated glycosaminoglycans, natural intra-cellular enzymes in their lysosomes, and natural intra-cellular material selected from the group consisting of DNA, histone and complexes of DNA-histone, the DNA, histone and complexes of DNA-histone having antigenic epitopes, the normal cells selected from the group consisting of two sub-populations of normal cells:

a first sub-population of normal cells having first target normal cells which also have the first antigenic receptor and further having a sensitivity to being killed by the natural system of the living host and a sensitivity to being killed by the first therapeutic agent, the first target normal cells further having a second antigenic receptor which is substantially specific to normal cells and which binds a second targeting agent, the second antigenic receptor being induced to endocytose when the second targeting agent binds to the second antigenic receptor; and the second sub-population of normal cells having non-target normal cells which are the remainder of the normal cells;

the method comprising the steps of:

administering to the living host a therapeutic effective amount of a soluble binary reagent including the first targeting agent which has substantial affinity for the first antigenic receptors, the binary reagent further including a soluble precipitable material which is attached to the first targeting agent;

allowing the soluble binary reagent to be endocytosed into the lysosomes of the first target cancer cells and into the lysosomes of the first target normal cells, the endocytosing and the natural intra-cellular enzymes in the lysosomes of the cells causing the soluble precipitable material to detach from the first targeting agent and thereby enabling the soluble precipitable material, upon being detached, to from a precipitate which has at least one of a first antigenic epitope being an epitope which is an integral part of the precipitate, a second antigenic epitope, and a neo-antigenic third epitope, the precipitate accumulating in the lysosomes within the first target cancer cells and within the first target normal cells;

continuing the administering of the soluble binary reagent into the living host to increase the accumulation of the precipitate in the first target cancer cells and in the first target normal cells to form a quantity of antigenic epitopes which is proportional to the amount of accumulation of the precipitate;

administering to the living host a therapeutic effective amount of the first therapeutic agent which causes a cell-killing process which kills the first target cancer cells and the first target normal cells and thereby causing the accumulation of the precipitate having the quantity of antigenic epitopes to be relocated into the extra-cellular fluid adjacent to the first target cancer cells and to the first target normal cells, the relocated precipitate now becoming a first extra-cellular precipitate having the quantity of antigenic epitopes, the cell killing process further causing the relocation of the natural intra-cellular material having antigenic epitopes to the extra-cellular fluid adjacent to the first target cancer cells and the first target normal cells;

administering to the living host a therapeutic effective amount of a bispecific reagent including a non-mammalian enzyme moiety, the bispecific reagent further including a targeting agent moiety having substantial affinity for one of the first antigenic epitope, the second antigenic epitope, and the neo-antigenic third epitope of the first extra-cellular precipitate, the bispecific reagent being received and bound at the first extra-cellular precipitate, the first extra-cellular precipitate being retained in the extra-cellular fluid for a period of time, which enables the non-mammalian enzyme moiety to convert an amount of an additional therapeutic agent into a new form adapted to remain adjacent to the first extra-cellular precipitate for a period of time sufficient to kill non-selectively all cells adjacent to the first extra-cellular precipitate; and administering to a living host a therapeutic effective amount of the additional therapeutic agent which is a soluble radioactive toxic agent to be converted by the non-mammalian enzyme moiety into a new form which remains adjacent to the first extra-cellular precipitate for a period of time sufficient to kill non-selectively all cells adjacent to the first extra-cellular precipitate.

2. A method in accordance with claim 1 in which the soluble precipitable material is an organic chemical comprising at least one member selected from the group consisting of opio-melanins, cellulose, chitosan, chitin, and indoxyl compounds having molecular positions of 1–7.

3. A method according to claim 1 in which the soluble precipitable material is radio-labeled.

4. A method in accordance with claim 1 in which the soluble precipitable material is converted by the natural intra-cellular enzymes into the intra-cellular precipitate, the intra-cellular precipitate when later relocated into the extra-cellular fluid becoming the first extra-cellular precipitate.

5. A method in accordance with claim 1 in which the soluble precipitable material is a soluble material which when detached from the first targeting agent is converted by at least of the natural intra-cellular enzymes into an insoluble intra-cellular precipitate, the insoluble intra-cellular precipitate when later relocated into the extra-cellular fluid becoming the first extra-cellular precipitate.

6. A method in accordance with claim 1 in which the soluble precipitable material which is converted by at least one of the natural intra-cellular enzymes into an insoluble intra-cellular precipitate has a neo-antigenic third epitope the intra-cellular precipitate when later relocated into the extra-cellular fluid becoming the first extra-cellular precipitate and having a neo-antigenic third epitope.

7. A method in accordance with claim 1 in which the soluble precipitable material is converted by at least one of the natural intra-cellular enzymes in the lysosomes into a soluble intermediate molecule, the soluble intermediate molecule being converted in the natural system of the host cells into the intra-cellular precipitate, the intra-cellular precipitate when later relocated into the extra-cellular fluid becoming the first extra-cellular precipitate.

8. A method in accordance with claim 1 in which the soluble precipitable material is converted by at least one of the natural intra-cellular enzymes in the lysosomes into a soluble intermediate molecule, the soluble intermediate molecule being oxidized by the natural environment in the host cell, thereby forming an oxidized soluble intermediate molecule, the oxidized soluble intermediate molecule spontaneously dimerizing and thereby making an insoluble molecule which forms the intra cellular precipitate which has a neo-antigenic third epitope not present on the soluble precipitable material from which the intra-cellular precipitate was formed, the intra-cellular precipitate when later relocated into the extra-cellular fluid becoming the first extra-cellular precipitate having a neo-antigenic third epitope.

9. A method in accordance with claim 2 in which the indoxyl compounds include at least one selected from the group consisting of sulphates, phosphates, glycosides, lipids, peptides, and nucleic acids which when attached to position 3 of the indoxyl compounds are cleavable by the natural intra-cellular enzymes in the lysosomes, the compound remaining after cleaving at position 3 being a soluble reactive intermediate molecule which is oxidized in the natural environment of the host cell thereby forming an oxidized soluble intermediate, the oxidized soluble intermediate spontaneously dimerizing and thereby forming an intra cellular precipitate which has a neo antigenic third epitope not present ran the indoxyl compounds from which the intra-cellular precipitate was formed, the intra-cellular precipitate when later relocated into the extra-cellular fluid becoming the first extra-cellular precipitate having a neo-antigenic third epitope.

10. A method in accordance with claim 2 in which each of the indoxyl compounds includes a substance which when attached to at least one of positions 4, 5, 6, and 7 of the indoxyl compound alters the characteristics of the indoxyl compounds and the intra-cellular precipitate thereof, the intra-cellular precipitate when later relocated into the extra-cellular fluid becoming the first extra-cellular precipitate.

11. A method in accordance with claim 2 in which each of the indoxyl compounds includes phenyl compounds attached at position 5 of the indoxyl compound to alter the characteristics of the indoxyl compounds and the intra cellular precipitate thereof, the intra-cellular precipitate when later relocated into the extra-cellular fluid becoming the first extra-cellular precipitate.

12. A method in accordance with claim 2 in which each of the indoxyl compounds includes benzyloxy compounds attached at position 5 of the indoxyl compounds to alter the characteristics of the indoxyl compounds and the intra-cellular precipitate thereof, the intra-cellular precipitate when later relocated into the extra-cellular fluid becoming the first extra-cellular precipitate.

13. A method in accordance with claim 2 in which each of the indoxyl compounds includes 5,5-bi-indoxyls attached at position 5 of the indoxyl compounds to alter the characteristics of the indoxyl compounds and the intra-cellular precipitate thereof, the intra-cellular precipitate when later relocated into the extra-cellular fluid becoming the first extra-cellular precipitate.

14. A method in accordance with claim 1 in which the soluble precipitable material includes both a third and a fourth soluble chemicals, each of the third and fourth soluble chemicals being attached to the targeting agent, the third and fourth soluble chemicals when detached from the targeting agent, reacting with each other to form the intra-cellular precipitate, the intra-cellular precipitate when later relocated into the extra-cellular fluid becoming the first extra-cellular precipitate.

15. A method in accordance with claim 1 in which the soluble precipitate material is selected from the group consisting of a chemical including dicationic amphiphillic compounds including tilorone and acradine orange, the soluble precipitable material upon being detached from the first targeting agent reacting with the endogenously made products of the cancer cells and of the normal cells thereby forming a complex comprised of the soluble precipitable material and the endogenously made products, the complex precipitating inside the targeted cells and the intra-cellular precipitate so formed becoming relatively non-digestible, the intra-cellular precipitate when later relocated into the extra-cellular fluid becoming the first extra-cellular precipitate.

16. A method in accordance with claim 1 in which the soluble precipitable material is composed of a soluble moiety and insoluble moiety, the soluble precipitable material being converted by the natural intra cellular enzymes into an intra cellular precipitate, the intra-cellular precipitate when later relocated into the extra-cellular fluid becoming the first extra-cellular precipitate.

17. A method in accordance with claim 1 in which the soluble precipitable material is composed of a soluble moiety and insoluble moiety, the soluble precipitable material being converted by the natural intra-cellular enzymes into an intra-cellular precipitate which has a neo-antigenic third epitope, the intra-cellular precipitate when later relocated into the extra-cellular fluid becoming the first extra-cellular preipitate having a neo-antigenic third epitope.

18. A method in accordance with claim 1 in which the soluble precipitable material has a soluble moiety and an insoluble moiety, the soluble moiety having a solubilizing effect on the insoluble moiety and being cleaved by the natural intra-cellular enzymes in the lysosomes from the insoluble moiety, the solubilizing effect or the soluble moiety being thereby dissipated and the remaining material, being insoluble, spontaneously forming an intra-cellular precipitate, the intra-cellular precipitate when later relocated into the extra-cellular fluid becoming the first extra-cellular precipitate.

19. A method in accordance with claim 1 in which the soluble precipitable material has a soluble moiety and an insoluble moiety, the soluble moiety having a solubilizing effect on the insoluble moiety, the soluble moiety being at least partially digested by the natural intra-cellular enzymes in the lysosomes, thereby dissipating the solubilizing effect or the soluble moiety, the insoluble moiety thereby spontaneously forming an intra-cellular precipitate, the intra-cellular precipitate when later relocated into the extra cellular fluid becoming the first extra cellular precipitate.

20. A method in accordance with claim 1 in which the soluble precipitable material has a soluble moiety and an insoluble moiety, the soluble moiety having a peptide moiety with a substantial binding affinity for the insoluble moiety and having a solubilizing effect on the insoluble moiety, the peptide moiety of the soluble moiety being partially digested by the natural intra-cellular enzymes in the lysosomes, the binding affinity of the peptide moiety having dissipated and thereby detaching the soluble moiety and eliminating the solubilizing effect of the soluble moiety, the remaining insoluble moiety spontaneously forming an intra-cellular precipitate, the intra-cellular precipitate when later relocated into the extra-cellular fluid becoming the first extra-cellular precipitate which later binds a peptide which has an affinity for the insoluble moiety.

21. A method in accordance with claim 1 in which the soluble precipitable material has a first chemical attached to reduce the rate of exit from the first target cancer cells and the first target normal cells of the soluble precipitable material prior to the soluble precipitable material forming an intra-cellular precipitate, the intra-cellular precipitate when later relocated into the extra cellular fluid becoming the first extra-cellular precipitate.

22. A method in accordance with claim 2 in which the indoxyl compounds have a first chemical attached to positions 4, 5, 6, and 7 of the indoxyl compounds to reduce substantially the rate of exit from the cells of the soluble indoxyl compound prior to the soluble indoxyl compounds forming an intra-cellular precipitate, the intra-cellular precipitate when later relocated into the extra-cellular fluid becoming the first extra-cellular precipitate.

23. A method in accordance with claim 22 in which the first chemical is attached to the indoxyl compounds by a bond which is incapable of being cleaved by mammalian and non-mammalian enzymes.

24. A method in accordance with claim 1 in which the first antigenic epitope is a portion of the first extra-cellular precipitate and is a portion of the soluble precipitable material from which the first extra-cellular precipitate was formed.

25. A method in accordance with claim 1 in which a second chemical is attached to the soluble precipitable material, the second chemical having an antigenic epitope which is present as the second antigenic epitope on the first extra-cellular precipitate.

26. A method in accordance with claim 2 in which a second chemical is attached to the indoxyl compounds at positions 4, 5, 6, or 7, the second chemical having an antigenic epitope which is present as the second antigenic epitope on the first extra-cellular precipitate.

27. A method in accordance with claim 1 in which the second antigenic epitope on the first extra-cellular precipitate is cleaved by non-mammalian enzymes and incapable of being cleaved by mammalian enzymes and incapable of being cleaved by the non-mammalian enzyme moiety of the bispecific reagent attached to the first extra-cellular precipitate.

28. A method in accordance with claim 1 in which tile first extra-cellular precipitate is at least one of a non metabolizable precipitate and a precipitate metabolizable by at least one of mammalian enzymes and non-mammalian enzymes.

29. A method in accordance with claim 28 in which the first extra-cellular precipitate is metabolizable at a rate which is controlled by the properties of the precipitate.

30. A method in accordance with claim 1 in which the first extra-cellular precipitate has at least one of a non-ordered structure such as one of an agregate and an ordered structure such as one of a linear polymer.

31. A method in accordance with claim 1 in which the first extra-cellular precipitate is insoluble or slightly soluble in the extra-cellular fluid found in the living host.

32. A method in accordance with claim 1 and further comprising the step of additionally administering to the living host a second binary reagent prior to and during the time of the administering of the binary reagent, the second binary reagent including the second targeting agent having a substantially specific binding affinity for the second antigenic receptor, the binding thereby inducing endocytosis, the second binary reagent being attached to the second targeting agent and, when detached, inhibiting the soluble precipitable material from forming an intra-cellular precipitate in the first target normal cells.

33. A method in accordance with claim 1 and further comprising the step of further administering to the living host a third binary reagent prior to and during the time of the administering of the first therapeutic agent, the third binary reagent including a second targeting agent having a substantially specific binding affinity for the second antigenic receptor, the binding thereby inducing endocytosis, the third binary reagent further including a material attached to the second targeting agent and, when detached, protecting the first target normal cells from being killed by the first therapeutic agent.

34. A method in accordance with claim 1 and further comprising the step of further administering a non-mammalian free enzyme to the living host prior to the step of administering the first therapeutic agent, the non mammalian free enzyme altering the precipitate formed in the extra-cellular fluid and resulting in antibodies and peptides which have an affinity for the precipitate to be unable to bind to the precipitate.

35. The method in accordance to claim 31 in which the altering of the precipitate comprising cleaving of the second antigenic epitope of the precipitate.

36. A method in accordance with claim 34 in which the altering of the precipitate comprising digesting of the precipitate.

37. A method in accordance with claim 34 and further comprising the step of still further administering to the living host an agent which causes the elimination of the free non-mammalian enzyme from the extra-cellular fluid.

38. A method in accordance with claim 34 and further comprising the step of still further administering to the living host an agent which inhibits the action of the free non-mammalian enzyme.

39. A method in accordance with claim 1 in which the administering of the first therapeutic agent for causing the cell killing process includes the administering of at least a cytotoxic agent which selectively kills the first target cancer cells.

40. A method in accordance with claim 1 in which the administering of the first therapuetic agent for causing the cell killing process includes the administering of at least a non cytotoxic agent which selectively kills the first target cancer cells.

41. A method in accordance with claim 1 in which the administering of the first therapeutic agent for causing the cell killing proces includes the administering of a procedure which alters hormonal status and which selectively kills the first target cancer cells.

42. A method in accordance with claim 1 in which the administering of the first therapeutic agent for causing the cell killing process includes a cell killing process which induces lysis and thereby selectively kills the first target cancer cells.

43. A method in accordance with claim 1 in which the targeting agent moiety of the bispecific reagent has a substantial affinity for the first antigenic epitope of the first extra-cellular precipitate.

44. A method in accordance with claim 1 in which the targeting agent moiety of the bispecific reagent has a substantial affinity for the second antigenic epitope of the first extra-cellular precipitate.

45. A method in accordance to claim 1 in which the targeting agent moiety of the bispecific reagent has a substantial affinity for the neo-antigenic third epitope of the first extra-cellular precipitate.

46. A method in accordance with claim 1 in which the non-mammalian enzyme moiety of the bispecific reagent is beta lactamase.

47. A method in accordance with claim 1 in which the non-mammalian enzyme moiety of the bispecific reagent is a penicillinase.

48. A method in accordance with claim 1 in which the non-mammalian enzyme moiety of the bispecific reagent is a glycosidase.

49. A method in accordance with claim 1 in which the non-mammalian enzyme moiety of the bispecific reagent is chondroitinase ABC.

50. A method in accordance with claim 1 in which the additional therapeutic agent is a soluble radioactive toxic agent and is an organic chemical selected from the group consisting of opio-melanins, cellulose, chitosan, chitin, proteoglycans, synthetic polymers, and indoxyl compounds having molecular positions 1–7.

51. A method in accordance with claim 1 in which the additional therapeutic agent is cell impermeant.

52. A method in accordance with claim 1 in which a cell-impermeant chemical is attached to the additional therapeutic agent the cell-impermeant chemical causing the additional therapeutic agent to become cell impermeant.

53. A method in accordance with claim 52 in which the cell-impermeant chemical is selected from the group consisting of thiol, anionic materials, and materials having a molecular weight greater than 1000 daltons.

54. A method in accordance with claim 1 in which the additional therapeutic agent is a second therapeutic agent, the second therapeutic agent being a soluble molecule which is converted by the non-mammalian enzyme moiety of the bispecific reagent into a new form which is insoluble and forms the second extra-cellular precipitate.

55. A method in accordance with claim 1 in which the additional therapeutic agent is a second therapeutic agent, the second therapeutic agent being a soluble molecule which is converted by the non-mammalian enzyme moiety of the bispecific reagent into a new form which is insoluble the new form being a second extra-cellular precipitate, the second extra-cellular precipitate having a neo-antigenic epitope not present on the second therapeutic agent from which the second extra-cellular precipitate was formed.

56. A method in accordance with claim 1 in which the additional therapeutic agent is a second therapeutic agent, the second therapeutic agent being converted by the non mammalian enzyme moiety of the bispecific reagent into a soluble intermediate molecule, the soluble intermediate molecule being naturally converted in the extra-cellular fluid into a new form which is insoluble, the new form being the second extra-cellular precipitate.

57. A method in accordance with claim 1 in which the additional therapeutic agent is a second therapeutic agent, the second therapeutic agent being oxidized and thereby forming an oxidized soluble intermediate molecule, the oxidized soluble intermediate molecule spontaneously being dimerized and thereby making a new form which is insoluble, the new form being the second extra-cellular precipitate, the second extra-cellular precipitate having a neo-antigenic epitope not present on the second therapeutic agent from which it was formed.

58. A method in accordance with claim 50 in which the indoxyl compounds are selected from the group consisting of indoxyl-penicillin, indoxyl-cephalosporin, and indoxyl-glycosides which when attached to position 3 of the indoxyl compounds bar cleavable by the non-mammalian enzyme moiety of the bispecific reagent, the compound remaining after cleaving at position 3 being a soluble reactive intermediate molecule which oxidizes and dimerizes to make a new form which is insoluble, the new form being the second extra-cellular precipitate.

59. A method in accordance with claim 50 in which each of the indoxyl compounds includes a substance when attached to at least one of positions 4, 5, 6, and 7 of the indoxyl compound alters the characteristics of the indoxyl compounds and the second extra-cellular precipitate.

60. A method in accordance with claim 50 in which each of the indoxyl compounds includes phenyl compounds attached at position 5 of the indoxyl compound to alter the characteristics of the indoxyl compounds and the second extra-cellular precipitate.

61. A method in accordance with claim 50 in which each of the indoxyl compounds is selected from benzyloxy compounds and attached at position 5 of the indoxyl compounds to alter the characteristics of the indoxyl compounds and of the second extra-cellular precipitate.

62. A method in accordance with claim 50 in which each of the indoxyl compounds includes 5,5-bi-indoxyls attached at position 5 of the indoxyl compounds to alter the characteristics of the indoxyl compounds and of the second extra-cellular precipitate.

63. A method in accordance with claim 1 in which the additional therapeutic agent is a second therapeutic agent, the second therapeutic agent having a soluble moiety and an insoluble moiety, the soluble moiety having a solubilizing effect on the insoluble moiety and being cleaved by the non-mammalian enzyme moiety of the bispecific reagent from the insoluble moiety, the solubilizing effect of the soluble moiety being thereby dissipated and the remaining moiety having been converted into a new form and being insoluble, spontaneously precipitates, and forms the second extra-cellular precipitate.

64. A method in accordance with claim 1 in which the additional therapeutic agent is a third therapeutic agent, the third therapeutic agent being converted by the non-mammalian enzyme moiety of the bispecific reagent into a new form, the new form being a soluble material having a neo-antigenic epitope not present on the third threapeutic agent from which the new form was created.

65. A method in accordance with claim 64 in which the third therapeutic agent is chondroitin sulphate which is converted by the non-mammalian enzyme moiety of the bispecific reagent into a new form, the new form of the third therapeutic agent being a soluble material with a neo-antigenic epitope not present on the chondroitin sulphate from which the new form of the third therapeutic agent was created.

66. The method in accordance with claim 64 and further comprising the step of administering to the living host a precipitating antibody having a specific affinity for the neo antigenic epitope on the new form of the third therapeutic agent the precipitating antibody being administered prior to the step of administering the third therapeutic agent and having the ability to bind to the neo-antigenic epitope of the new form of the third therapeutic agent, the binding causing the new form of the third theapeutic agent to form a third extra-cellular precipitate which remains for a period of time adjacent to the relocated first extra cellular precipitate.

67. A method according to claim 1 and further comprising the step of administering to the living host a second bispecific reagent to tether the first extra-cellular precipitate, the second bispecific reagent having two moieties, a first moiety having an affinity for one of the first antigenic epitope, the second antigenic epitope, and the neo-antigenic third epitope of the first extra-cellular precipitate, a second moiety having an affinity for the third antigenic receptor on the second target cancer cells, the second bispecific reagent being administered prior to the administration of the first therapeutic agent and enabling the fist extra-cellular precipitate to be retained for a period of time adjacent to the third antigenic receptor on the second target cancer cells.

68. A method according to 67 in which the first moiety of the second bispecific reagent has an affinity for the first antigenic epitope of the first extra-cellular precipitate.

69. A method according to 67 in which the first moiety of the second bispecific reagent has an affinity for the second antigenic epitope of the first extra-cellular precipitate.

70. A method according to 67 in which the first moiety of the second bispecific reagent has an affinity for the neo-antigenic third epitope of the first extra-cellular precipitate.

71. A method according to claim 1 and further comprising the step of administering to the living host a third bispecific reagent, the third bispecific reagent having two moieties, a first moiety having an affinity for one of the first antigenic epitope, a second antigenic epitope, and the neo-antigenic third epitope of the first extra-cellular precipitate, the second moiety having an affinity for the cancer-altered antigenic epitopes on the cancer-altered extra-cellular matrix, the third bispecific reagent being administered prior to the administration of the first therapeutic agent and enabling the first extra-cellular precipitate to be retained for a period of time adjacent to the cancer-altered antigenic epitopes on the cancer-altered extra-cellular matrix.

72. A method according to 71 in which the first moiety of the third bispecific reagent has an affinity for the first antigenic epitope of the first extra-cellular precipitate.

73. A method according to 71 in which the first moiety of the third bispecific reagent has an affinity for the second antigenic epitope of the first extra-cellular precipitate.

74. A method according to 71 in which the first moiety of the third bispecific reagent has an affinity for the neo-antigenic third epitope of the first extra-cellular precipitate.

75. A method according to claim 1 and further comprising the step of administering to the living host a fourth bispecific reagent, the fourth bispecific reagent having two moieties, a first moiety having an affinity for one of the first antigenic epitope, the second antigenic epitope, and the neo-antigenic third epitope of the first extra-cellular precipitate, a second moiety having an affinity for the antigenic epitopes on the relocated natural intra-cellular material, the fourth bispecifc reagent being administered prior to the administration of the first therapeutic agent and enabling the first extra-cellular precipitate to be retained for a period of time adjacent to the antigenic epitopes on the relocated natural intra-cellular material.

76. A method according to 75 in which the first moiety of the fourth bispecific reagent has an affinity for the first antigenic epitope of the first extra-cellular precipitate.

77. A method according to 75 in which the first moiety of the fourth bispecific reagent has an affinity for the second antigenic epitope of the first extra-cellular precipitate.

78. A method according to 75 in which the first moiety of the fourth bispecific reagent has an affinity for the neo-antigenic third epitope of the first extra-cellular precipitate.

79. A method according to claim 55 and further comprising the stop of administering to the living host a fifth bispecific reagent comprised of a molecule having a substantial affinity for the neo-antigenic epitope of the second extra-cellular precipitate, the fifth bispecific reagent further having a molecule with a substantial affinity for the third antigenic receptor on the second target cancer cell, the fifth bispecific reagent being administered prior to the step of additionally administering the second therapeutic agent and enabling the second extra-cellular precipitate to be retained for a period of time adjacent to the third antigenic receptor on the second target cancer cells.

80. A method according to claim 55 and further comprising the step of administering to the living host a sixth bispecific reagent comprised of a molecule having a substantial affinity for the neo-antigenic epitope on the second extra-cellular precipitate, the sixth bispecific reagent further having a molecule with a substantial affinity for the cancer-altered antigenic epitopes on the cancer-altered extra-cellular matrix, the sixth bispecific reagent being administered prior to the step of additionally administering the second therapeutic agent and enabling the second extra-cellular precipitate to be retained for a period of time adjacent to cancer-altered antigenic epitopes on the cancer-altered extra-cellular matrix.

81. A method according to claim 55 and further comprising the step of administering to the living host a seventh bispecific reagent comprised of a molecule having a substantial affinity for the neo-antigenic epitope on the second extra-cellular precipitate, the seventh bispecific reagent further having a molecule with a substantial affinity for the antigenic epitopes on the natural intra-cellular material, the seventh bispecific reagent being administered prior to the step of administering the second therapeutic agent and enabling the second extra-cellular precipitate to be retained for a period of time adjacent to the antigenic epitopes on the natural intra-cellular material.

82. A method according to claim 64 and further comprising the step of administering to the living host an eighth bispecific reagent comprised of a molecule having a substantial affinity for the neo-antigenic epitope of the new form of the third therapeutic agent, the eighth bispecific reagent further having a molecule with a substantial affinity for the third antigenic receptor on the second target cancer cells, the eighth bispecific reagent to be administered prior to the step of administering the third therapeutic agent and enabling the new form of the third therapeutic agent to be retained for a period of time adjacent to the third antigenic receptor on the second target cancer cells.

83. A method according to claim 64 and further comprising the step of administering to the living host a ninth bispecific reagent comprised of a molecule having a substantial affinity for the neo antigenic epitope on the new form of the third therapeutic agent, the ninth bispecific reagent further having a molecule with a substantial affinity for the cancer-altered antigenic epitopes on the cancer-altered extra-cellular matrix, the ninth bispecifc reagent being administered prior to the step of administering the third therapeutic agent and enabling the new form of the third therapeutic agent to be retained for a period of time adjacent to the cancer altered antigenic epitopes on the cancer-altered extra-cellular matrix.

84. A method according to claim 64 and further comprising the step of administering to the living host a tenth bispecific reagent comprised of a molecule having a substantial affinity for the neo-antigenic epitope on the new form of the third therapeutic agent, the tenth bispecific reagent further having a molecule with a substantial affinity for the antigenic epitopes on the natural intra-cellular material, the tenth bispecific reagent being administered prior to the step of administering the third therapeutic agent and enabling the new form of the third therapeutic agent to be retained for a period of time adjacent to the antigenic epitopes on the natural intra-cellular material.

85. A method in accordance with claim 13 in which two indoxyl compounds are attached via a spacer molecule.

86. A method in accordance with claim 62 in which two indoxyl compounds are attached via a spacer molecule.

* * * * *